United States Patent
Grady et al.

(10) Patent No.: US 8,828,695 B2
(45) Date of Patent: *Sep. 9, 2014

(54) METHOD FOR PRODUCING BUTANOL USING TWO-PHASE EXTRACTIVE FERMENTATION

(75) Inventors: Michael Charles Grady, Oaklyn, NJ (US); Mehmedalija Jahic, Wilmington, DE (US); Ranjan Patnaik, Newark, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 174 days.

This patent is subject to a terminal disclaimer.

(21) Appl. No.: 12/759,283

(22) Filed: Apr. 13, 2010

(65) Prior Publication Data

US 2010/0221802 A1 Sep. 2, 2010

Related U.S. Application Data

(63) Continuation-in-part of application No. 12/478,389, filed on Jun. 4, 2009.

(60) Provisional application No. 61/058,567, filed on Jun. 4, 2008.

(51) Int. Cl.
*C12P 7/16* (2006.01)
*C12P 1/00* (2006.01)

(52) U.S. Cl.
CPC ... *C12P 7/16* (2013.01); *Y02E 50/10* (2013.01)
USPC ............................................. 435/160; 435/41

(58) Field of Classification Search
None
See application file for complete search history.

(56) References Cited

U.S. PATENT DOCUMENTS

| | | |
|---|---|---|
| 2,374,379 A | 4/1945 | Rittmeister |
| 3,193,586 A | 7/1965 | Rittmeister |
| 3,394,990 A | 7/1968 | Weingaertner |
| 4,865,973 A | 9/1989 | Kollerup et al. |
| 5,110,319 A | 5/1992 | Turpin et al. |
| 7,541,173 B2 | 6/2009 | Bramucci et al. |
| 2007/0092957 A1 | 4/2007 | Donaldson et al. |
| 2007/0259410 A1 | 11/2007 | Donaldson et al. |
| 2007/0292927 A1 | 12/2007 | Donaldson et al. |
| 2008/0182308 A1 | 7/2008 | Donaldson et al. |

(Continued)

FOREIGN PATENT DOCUMENTS

| | | |
|---|---|---|
| FR | 1061101 | 4/1954 |
| FR | 1061102 | 4/1954 |

(Continued)

OTHER PUBLICATIONS

Ramey et al., Production of Butyric Acid and Butanol from Biomass, Final Report, 2004, pp. 1-103.*
Ward et al. see p. V of, n-Propanol and iso-butanol from *Clostridium acetobutylicum.*, The Society for general Microbiology; Journal of General Microbiology, 1970, vol. 61, pp. i-x.*
Yoshimoto et al., Pyruvate Decarboxylase Encoded by the PDC1 Gene Contributes, at Least Partially, to the Decarboyxlation of α-Ketoisocaproate for Isoamyl Alcohol Formation in *Saccharomyces cerevisiae.*, Journal of Bioscience and Bioengineering, 2001, vol. 92, pp. 83-85.*

(Continued)

*Primary Examiner* — Alexander Kim

(57) ABSTRACT

A method of making butanol from at least one fermentable carbon source that overcomes the issues of toxicity resulting in an increase in the effective titer, the effective rate, and the effective yield of butanol production by fermentation utilizing a recombinant microbial host wherein the butanol is extracted into specific organic extractants during fermentation.

18 Claims, 9 Drawing Sheets

(56) References Cited

U.S. PATENT DOCUMENTS

Figure 1:
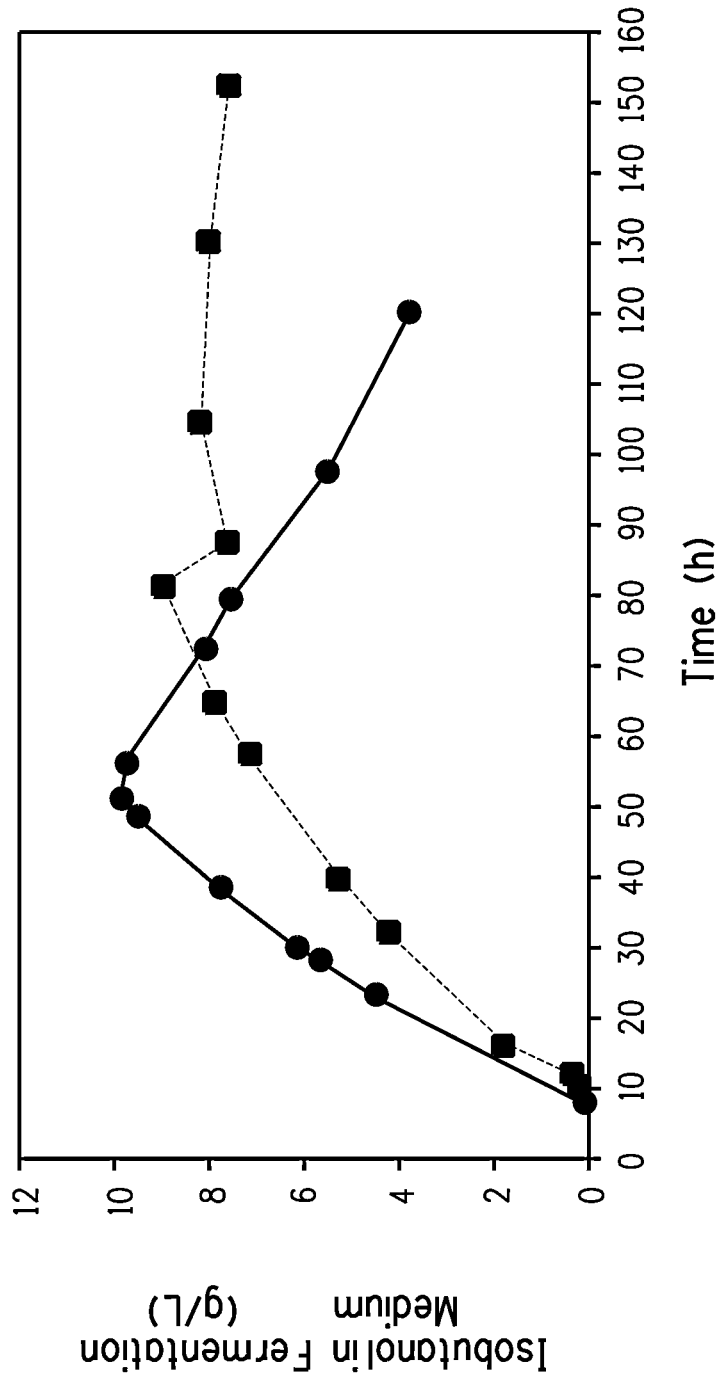

| | | | |
|---|---|---|---|
| 2008/0274526 A1* | 11/2008 | Bramucci et al. | 435/160 |
| 2009/0163376 A1 | 6/2009 | Li et al. | |
| 2009/0171129 A1 | 7/2009 | Evanko et al. | |
| 2010/0062505 A1* | 3/2010 | Gunawardena et al. | 435/160 |
| 2010/0143992 A1 | 6/2010 | Erdner-Tindall et al. | |
| 2010/0143993 A1 | 6/2010 | Erdner-Tindall et al. | |
| 2010/0143994 A1 | 6/2010 | Erdner-Tindall et al. | |
| 2010/0143995 A1 | 6/2010 | Erdner-Tindall et al. | |

FOREIGN PATENT DOCUMENTS

| | | | |
|---|---|---|---|
| GB | 1064317 | 4/1967 | |
| JP | 61192291 | 8/1986 | |
| JP | 62022593 | 1/1987 | |
| WO | 2007041269 | 4/2007 | |
| WO | 2007050671 | 5/2007 | |
| WO | 2007130518 | 11/2007 | |
| WO | 2007130521 | 11/2007 | |
| WO | 2007146377 | 12/2007 | |
| WO | 2008024292 | 2/2008 | |
| WO | 2008024293 | 2/2008 | |
| WO | 2008024294 | 2/2008 | |
| WO | WO/2008/121701 | * 10/2008 | C12N 1/19 |
| WO | 2008143704 | 11/2008 | |
| WO | 2009086391 | 7/2009 | |

OTHER PUBLICATIONS

Liu et al., High-Oleic and High-Stearic Cottonseed Oils: Nutritionally Improved Cooking Oils Developed Using Gene Silencing., Journal of the American College of Nutrition (2002), vol. 21, pp. 205S-211S.*
Amann et al., Gene 69: 301-315, 1988.
Horton et al. (1989) Gene 77:61-68.
Roffler et al., Biotechnol. Bioeng. 31:135-143, 1988.
Roffler et al., Bioprocess Engineering 2:1-12, 1987.
Evans et al., Appl. Environ. Microbiol. 54:1662-1667, 1988.
De Cavalho et al., Microsc. Res. Tech. 64:215-22 (2004).
Kabelitz et al., Fems Microbiol. Lett. 220:223-227 (2003).
Tomas et al., J. Bacteriol. 186:2006-2018 (2004).
Hermann et al., Appl. Environ. Microbiol. 50:1238-1243 (1985).
U.S. Appl. No. 61/058,970 now filed as U.S. Appl. No. 12/477,942 on Jun. 4, 2009.
U.S. Appl. No. 61/048,291 now filed as U.S. Appl. No. 12/430,356 on Apr. 27, 2009.
Shi, Z. et al., Bioprocess. Biosyst. Eng. 27(3):175-83, 2005.
Bruce, Lynda J. et al., Biotechnology Prog., 7, pp. 116-124, 1991.
Evans, P.J., et al., Journal Applied Biochemistry and Biotechnology, Issue vol. 17, Nos. 1-3, pp. 175-192, Apr. 1988.
Ishii, Shigeo et al., Journal of Chemical Engineering of Japan, 18(2), 125-30, 1985.
Ishizaki, A. et al., J. Biosc.i Bioeng. 87(3):352-6, 1999.
Jeon, Y. J. et al., Ann NY Acad. Sci. 506:536-42, 1987.
Largier, S. T. et al., Appl. Environ. Microbiol. 50(2):477-481, 1985.
Monot, F. et al., Appl. Environ. Microbial. 44(6):1318-1324, 1982.
U.S. Appl. No. 61/100,792, filed Sep. 29, 2008 now U.S. Appl. No. 12/569,636, filed Sep. 29, 2009.
Methods in Yeast Genetics, 2005, pp. 201-202, Cold Spring Harbor Laboratory Press, Cold Spring Harbor, NY.
Mutschlechner, O. et al., J. Mol. Microbiol. Biotechnol. 2(1):101-5, 2000.
Wang HY, Robinson FM, Lee SS (1981) Biotechnol Bioeng Symp 11:555.
Minier M, Goma G (1982) Biotechnol Bioeng 24:1565.
Matsumura M, Markl H (1984) Appl Microbiolo Biotechnol 20:371.
Taya M et al, (1985) J Ferment Technol 63:181.
Honda H et al (1986) J Chem Eng Jpn 19:268.
Wayman M, Parekh R (1987) J Ferment Technol 65:295.
Eckert G, Schugerl K (1987) Appl Microbiol Biotechnol 27:221.
Tanaka et al (1987) Biotechnol Bioeng 30:22.
Bar R (1988) J Chem Tech Biotechnol 43:49.
Roffler et al (1988) Biotechnol Bioeng 32:192.
Eiterman MA et al, (1989) Appl Microbiol Biotechnol 30:614.
Weilnhammer et al (1992) inL Kreysa G and Driesel AJ (eds) 10th Dechema Annual Meeting of Biotechnologists (Dechema biotechnology conferences), VCH, Karlsuhe, p. 197.
Bruce LJ and Daugulis AJ (1992) Biotechnol Lett 14:71.
Mitchell et al., Biotech. and Bioeng., vol. 30, pp. 348-351 (1987).
Jones TD et al (1993) Biotechnol Lett 15:871.
Daugulis et al (1994) Biotechnol Lett 16:637.
Weilnhammer C and Blass E (1994) Chem Eng Technol 17:365.
Qureshi N and Maddox IS (1995) J Ferment Bioeng 80:185.
Maddox IS and Qureshi N (1995) Process Biochem 30:209.
Gyamerah M and Glover J (1996) J Chem Tech Biotechnol 66:145.
Moritz JW and Duff SJB (1996) Biotechnol Bioeng 49:504.
Kapucu H and Mehmetoglu U (1998) Appl Biochem Biotechnol 75:205.
Roffler et al in Extractive Bioconversions ed by Bo Mattiasson and Olle Holst (Marcel Dekker, NY, 1991) pp. 133-172.
International Search Report and Written Opinion in copending PCT/US2009/046278 mailed Mar. 3, 2010.
Offeman et al., Separation and Purification Technology, vol. 63, pp. 444-451 (2008).
Roffler, Steve Ronald, Ph. D., "Extractive fermentation-lactic acid and acetone/butanol production", University of California, Berkeley 1986, pp. 1-289.
Munson et al., Ind. Eng. Chem. Proc. Dev. (1984) 23(1) pp. 109-115.
Davison, Brian H., et al., Applied Biochemistry and Biotechnology, 39-40, pp. 415-26, 1993.
Daugulis A. J., Curr. Opin. Biotechnol. 5(2):192-5 1994.
Ezeji, T. C. et al., Curr. Opin. Biotechnol. 18(3):220-7, 2007.
Q97ED7_CLOAB (last viewed on May 11, 2011).
EC 2.2.1.6 from Brenda (last viewed on May 11, 2011), pp. 1, 66-67.
Aristidou et al. Modification of central metabolic pathway in *Escherichia coli* to reduce acetate accumulation by heterologous expression of the *Bacillus subtillis* acetolactate synthase gene., Biotechnol. Bioeng, 1994, vol. 44, pp. 944-951.
Steen et al., Metabolic engineering of *Saccharomyces cerevisiae* for the production of n-butanol., Microb Cell Fact., Dec. 3, 2008, vol. 7:36, pp. 1-8.
Hohmann, Characterization of PDC6, a third structural gene for pyruvate decarboxylase in *Saccharomyces cerevisiae*, J Bacteriol. Dec. 1991, vol. 173(24), pp. 7963-7969.
Ward et al., see p.V of, n-Propanol and iso-butanol from *Clostridium acetobutylicum*., The Society for General Microbiology; Journal of General Microbiology, 1970,vol. 61, pp. i-x.
Nair, et al., "Molecular Characterization of an Aldehyde/Alcohol Dehydrogenase Gene from *Clostridium acetobutylicum* ATCC 824", Journal of Bacteriology, Feb. 1994, p. 871-885.
Nair, et al., "Regulation of the sol Locus Genes for Butanol and Acetone Formation in *Clostridium acetobutylicum* ATCC 824 by a Putative Transcriptional Repressor", Journal of Bacteriology, Jan. 1999, p. 319-330.
Qureshi et al., Production of Acetone Butanol Ethanol (ABE) by a Hyper-Producing Mutant Strain of *Clostridium beijerinckii* BA101 and Recovery by Pervaporation, Biotechnol. Prog., vol. 15 (1999) pp. 594-602.
Bailey, et al. Biochemical Engineering Fundamentals, second edition, McGraw Hill, New York (1986) pp. 280-285; 383-388; and 620-622.
Miller, J.H., A Short Course in Bacterial Genetics, Cold Spring Harbor Laboratory, Cold Spring Harbor, N.Y. (1992) Experiment 19, pp. 263-274.
Ausubel, F. M. et al. Current Protocols in Molecular Biology (1997); Unit 1.8.
Grady et al., U.S. Appl. No. 12/758,870, filed Apr. 13, 2010.
Atsumi et al. Nature 451(3):86-90, 2008.
Baba et al., Mol. Syst. Biol., 2:1-11, 2006.
Datsenko, et al., Proc. Natl. Acad. Sci., U.S.A. 97 6640-6645, 2000.
Cherepanov, et al., Gene, 158: 9-14, 1995.

* cited by examiner

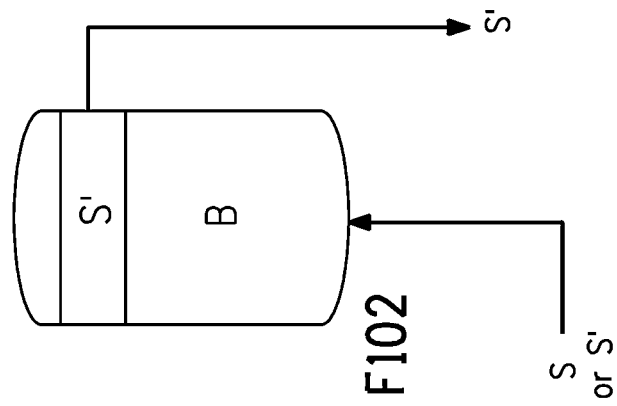
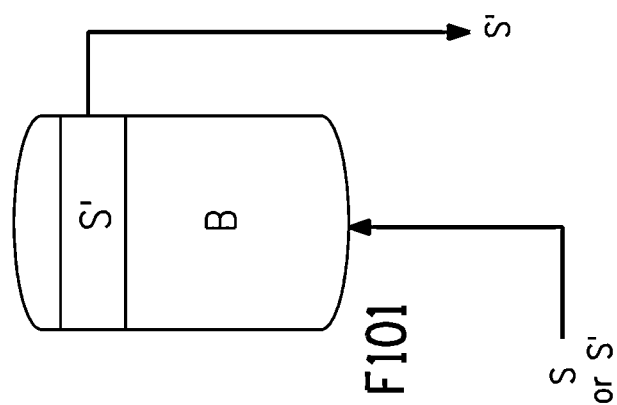
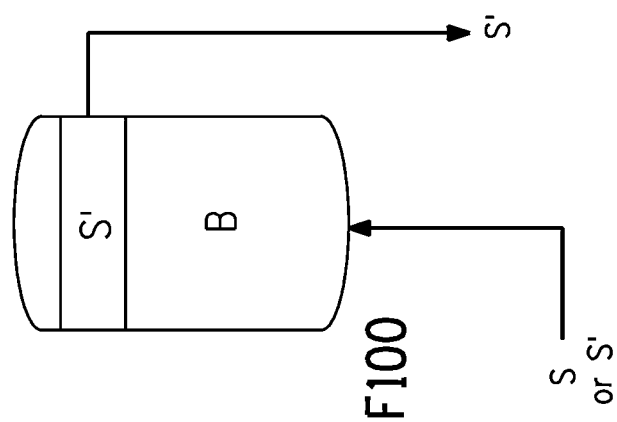
FIG. 9

```
                              SEQUENCE LISTING

<160> NUMBER OF SEQ ID NOS: 86

<210> SEQ ID NO 1
<211> LENGTH: 1680
<212> TYPE: DNA
<213> ORGANISM: Klebsiella pneumoniae

<400> SEQUENCE: 1
atggacaaac agtatccggt acgccagtgg gcgcacggcg ccgatctcgt cgtcagtcag      60
ctggaagctc agggagtacg ccaggtgttc ggcatccccg gcgccaaaat cgacaaggtc     120
tttgattcac tgctggattc ctccattcgc attattccgg tacgccacga agccaacgcc     180
gcatttatgg ccgccgccgt cggacgcatt accggcaaag cgggcgtggc gctggtcacc     240
tccggtccgg gctgttccaa cctgatcacc ggcatggcca ccgcgaacag cgaaggcgac     300
ccggtggtgg ccctgggcgg cgcggtaaaa cgcgccgata aagcgaagca ggtccaccag     360
agtatggata cggtggcgat gttcagcccg gtcaccaaat acgccatcga ggtgacggcg     420
ccggatgcgc tggcggaagt ggtctccaac gccttccgcg ccgccgagca gggccggccg     480
ggcagcgcgt tcgttagcct gccgcaggat gtggtcgatg gccgtcag cggcaaagtg      540 ctgccggcca gcggggcccc gcagatgggc gccgcgccgg atgatgccat cgaccaggtg     600
gcgaagctta tcgcccaggc gaagaacccg atcttcctgc tcggcctgat ggccagccag     660
ccggaaaaca gcaaggcgct cgccgtttg ctggagacca gccatattcc agtcaccagc      720
acctatcagg ccgccggagc ggtgaatcag gataacttct ctcgcttcgc cggccgggtt     780
gggctgttta caaccaggc cggggaccgt ctgctgcagc tcgccgacct ggtgatctgc      840
atcggctaca gcccggtgga atacgaaccg gcgatgtgga acagcggcaa cgcgacgctg     900
gtgcacatcg acgtgctgcc cgcctatgaa gagcgcaact acaccccgga tgtcgagctg     960
gtgggcgata tcgccggcac tctcaacaag ctggcgcaaa atatcgatca tcggctggtg    1020 ctctcccgc aggcggcgga gatcctccgc gaccgccagc accagcgcga gctgctggac       1080
cgccgcggcg cgcagctcaa ccagtttgcc ctgcatcccc tgcgcatcgt tcgcgccatg    1140
caggatatcg tcaacagcga cgtcacgttg accgtggaca tgggcagctt ccatatctgg    1200
attgcccgct acctgtacac gttccgcgcc cgtcaggtga tgatctccaa cggccagcag    1260
accatgggcg tcgccctgcc ctgggctatc ggcgcctggc tggtcaatcc tgagcgcaaa    1320
gtggtctccg tctccggcga cggcggcttc ctgcagtcga gcatggagct ggagaccgcc    1380
gtccgcctga agccaacgt gctgcatctt atctgggtcg ataacggcta caacatggtc      1440
gctatccagg aagagaaaaa atatcagcgc ctgtccggcg tcgagtttgg gccgatggat    1500
tttaaagcct atgccgaatc cttcggcgcg aaagggtttg ccgtggaaag cgccgaggcg    1560
ctggagccga ccctgcgcgc ggcgatggac gtcgacggcc cggcggtagt ggccatcccg    1620
gtggattatc gcgataaccc gctgctgatg gccagctgc atctgagtca gattctgtaa     1680

<210> SEQ ID NO 2
<211> LENGTH: 559
<212> TYPE: PRT
<213> ORGANISM: Klebsiella pneumoniae

<400> SEQUENCE: 2
```

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
            35                  40                  45

Ile Arg Ile Ile Pro Val Arg His Glu Ala Asn Ala Ala Phe Met Ala
50                  55                  60

Ala Ala Val Gly Arg Ile Thr Gly Lys Ala Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
            115                 120                 125

Ser Pro Val Thr Lys Tyr Ala Ile Glu Val Thr Ala Pro Asp Ala Leu
            130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
            195                 200                 205

Asn Pro Ile Phe Leu Leu Gly Leu Met Ala Ser Gln Pro Glu Asn Ser
210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
            275                 280                 285

Glu Pro Ala Met Trp Asn Ser Gly Asn Ala Thr Leu Val His Ile Asp
            290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
            355                 360                 365

Phe Ala Leu His Pro Leu Arg Ile Val Arg Ala Met Gln Asp Ile Val
            370                 375                 380

Asn Ser Asp Val Thr Leu Thr Val Asp Met Gly Ser Phe His Ile Trp
385                 390                 395                 400

Ile Ala Arg Tyr Leu Tyr Thr Phe Arg Ala Arg Gln Val Met Ile Ser
                405                 410                 415
```

```
Asn Gly Gln Gln Thr Met Gly Val Ala Leu Pro Trp Ala Ile Gly Ala
            420                 425                 430

Trp Leu Val Asn Pro Glu Arg Lys Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu Arg Ala Ala
            515                 520                 525

Met Asp Val Asp Gly Pro Ala Val Ala Ile Pro Val Asp Tyr Arg
            530                 535                 540

Asp Asn Pro Leu Leu Met Gly Gln Leu His Leu Ser Gln Ile Leu
545                 550                 555
```

<210> SEQ ID NO 3
<211> LENGTH: 1476
<212> TYPE: DNA
<213> ORGANISM: Escherichia coli

<400> SEQUENCE: 3

```
atggctaact acttcaatac actgaatctg cgccagcagc tggcacagct gggcaaatgt     60
cgctttatgg ccgcgatga attcgccgat ggcgcgagct accttcaggg taaaaaagta    120
gtcatcgtcg gctgtggcgc acagggtctg aaccagggcc tgaacatgcg tgattctggt    180
ctcgatatct cctacgctct gcgtaaagaa gcgattgccg agaagcgcgc gtcctggcgt    240
aaagcgaccg aaaatggttt taaagtgggt acttacgaag aactgatccc acaggcggat    300
ctggtgatta acctgacgcc ggacaagcag cactctgatg tagtgcgcac cgtacagcca    360
ctgatgaaag acggcgcggc gctgggctac tcgcacggtt tcaacatcgt cgaagtgggc    420
gagcagatcc gtaaagatat caccgtagtg atggttgcgc gaaatgccc aggcaccgaa    480
gtgcgtgaag agtacaaacg tgggttcggc gtaccgacgc tgattgccgt tcacccggaa    540
aacgatccga aggcgaagg catggcgatt gccaaagcct gggcggctgc aaccggtggt    600
caccgtgcgg gtgtgctgga atcgtccttc gttgcggaag tgaaatctga cctgatgggc    660
gagcaaacca tcctgtgcgg tatgttgcag gctggctctc tgctgtgctt cgacaagctg    720
gtggaagaag gtaccgatcc agcatacgca gaaaaactga ttcagttcgg ttgggaaacc    780
atcaccgaag cactgaaaca gggcggcatc accctgatga tggaccgtct ctctaacccg    840
gcgaaactgc gtgcttatgc gctttctgaa cagctgaaag atcatggc accctgttc    900
cagaaacata tggacgacat catctccggc gaattctctt ccggtatgat ggcggactgg    960
gccaacgatg ataagaaact gctgacctgg cgtgaagaga ccggcaaaac cgcgtttgaa   1020
accgcgccgc agtatgaagg caaaatcggc gagcaggagt acttcgataa aggcgtactg   1080
atgattgcga tggtgaaagc gggcgttgaa ctggcgttcg aaaccatggt cgattccggc   1140
atcattgaag agtctgcata ttatgaatca ctgcacgagc tgccgctgat gccaacacc   1200
atcgcccgta gcgtctgta cgaaatgaac gtggttatct ctgataccgc tgagtacggt   1260
aactatctgt tctcttacgc ttgtgtgccg ttgctgaaac cgtttatggc agagctgcaa   1320
```

-continued

```
ccgggcgacc tgggtaaagc tattccggaa ggcgcggtag ataacgggca actgcgtgat      1380
gtgaacgaag cgattcgcag ccatgcgatt gagcaggtag gtaagaaact gcgcggctat      1440
atgacagata tgaaacgtat tgctgttgcg ggttaa                               1476
```

<210> SEQ ID NO 4
<211> LENGTH: 491
<212> TYPE: PRT
<213> ORGANISM: Escherichia coli

<400> SEQUENCE: 4

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350
```

```
        Glu Tyr Phe Asp Lys Gly Val Leu Met Ile Ala Met Val Lys Ala Gly
                    355                 360                 365

Val Glu Leu Ala Phe Glu Thr Met Val Asp Ser Gly Ile Ile Glu Glu
            370                 375                 380

Ser Ala Tyr Tyr Glu Ser Leu His Glu Leu Pro Leu Ile Ala Asn Thr
        385                 390                 395                 400

Ile Ala Arg Lys Arg Leu Tyr Glu Met Asn Val Val Ile Ser Asp Thr
                        405                 410                 415

Ala Glu Tyr Gly Asn Tyr Leu Phe Ser Tyr Ala Cys Val Pro Leu Leu
                    420                 425                 430

Lys Pro Phe Met Ala Glu Leu Gln Pro Gly Asp Leu Gly Lys Ala Ile
                435                 440                 445

Pro Glu Gly Ala Val Asp Asn Gly Gln Leu Arg Asp Val Asn Glu Ala
            450                 455                 460

Ile Arg Ser His Ala Ile Glu Gln Val Gly Lys Lys Leu Arg Gly Tyr
        465                 470                 475                 480

Met Thr Asp Met Lys Arg Ile Ala Val Ala Gly
                        485                 490

<210> SEQ ID NO 5
<211> LENGTH: 1851
<212> TYPE: DNA
<213> ORGANISM: Escherichia coli

<400> SEQUENCE: 5
atgcctaagt accgttccgc caccaccact catggtcgta atatggcggg tgctcgtgcg      60
ctgtggcgcg ccaccggaat gaccgacgcc gatttcggta agccgattat cgcggttgtg     120
aactcgttca cccaatttgt accgggtcac gtccatctgc gcgatctcgg taaactggtc     180
gccgaacaaa ttgaagcggc tggcggcgtt gccaaagagt caacaccat tgcggtggat      240 gatgggattg ccatgggcca cggggggatg ctttattcac tgccatctcg cgaactgatc     300
gctgattccg ttgagtatat ggtcaacgcc cactcgccg acgccatggt ctgcatctct      360
aactgcgaca aaatcacccc ggggatgctg atggcttccc tgcgcctgaa tattccggtg     420
atctttgttt ccggcggccc gatggaggcc gggaaaacca actttccga tcagatcatc      480 aagctcgatc tggttgatgc gatgatccag ggcgcagacc cgaaagtatc tgactcccag     540
agcgatcagg ttgaacgttc gcgtgtccg acctgcggtt cctgctccgg atgtttacc      600 gctaactcaa tgaactgcct gaccgaagcg ctgggcctgt cgcagccggg caacggctcg     660
ctgctggcaa cccacgccga ccgtaagcag ctgttcctta tgctggtaa acgcattgtt      720 gaattgacca acgttatta cgagcaaaac gacgaaagtg cactgccgcg taatatcgcc      780
agtaaggcgg cgtttgaaaa cgccatgacg ctggatatcg cgatgggtgg atcgactaac     840
accgtacttc acctgctggc ggcggcgcag gaagcggaaa tcgacttcac catgagtgat     900
atcgataagc tttccgcaa ggttccacag ctgtgtaaag ttgcgccgag cacccagaaa      960
taccatatgg aagatgttca ccgtgctggt ggtgttatcg gtattctcgg cgaactggat    1020
cgcgcggggt tactgaaccg tgatgtgaaa aacgtacttg gcctgacgtt gccgcaaacg     1080
ctggaacaat acgacgttat gctgacccag gatgacgcgg taaaaatat gttccgcgca    1140 ggtcctgcag gcattcgtac cacacaggca ttctcgcaag attgccgttg ggatacgctg    1200
gacgacgatc gcgccaatgg ctgtatccgc tcgctggaac acgcctacag caaagacggc    1260
ggcctggcgg tgctctacgg taactttgcg gaaaacggct gcatcgtgaa aacggcaggc    1320
```

-continued

```
gtcgatgaca gcatcctcaa attcaccggc ccggcgaaag tgtacgaaag ccaggacgat    1380
gcggtagaag cgattctcgg cggtaaagtt gtcgccggag atgtggtagt aattcgctat    1440
gaaggcccga aaggcggtcc ggggatgcag gaaatgctct acccaaccag cttcctgaaa    1500
tcaatgggtc tcggcaaagc ctgtgcgctg atcaccgacg tcgtttctc tggtggcacc     1560 tctggtcttt ccatcggcca cgtctcaccg gaagcggcaa gcggcggcag cattggcctg    1620
attgaagatg tgaccctgat cgctatcgac atcccgaacc gtggcattca gttacaggta    1680
agcgatgccg aactggcggc gcgtcgtgaa gcgcaggacg ctcgaggtga caaagcctgg    1740
acgccgaaaa atcgtgaacg tcaggtctcc tttgccctgc gtgcttatgc cagcctggca    1800
accagcgccg acaaaggcgc ggtgcgcgat aaatcgaaac tgggggggtta a            1851
```

<210> SEQ ID NO 6
<211> LENGTH: 616
<212> TYPE: PRT
<213> ORGANISM: Escherichia coli

<400> SEQUENCE: 6

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270
```

Ile Ala Met Gly Gly Ser Thr Asn Thr Val Leu His Leu Leu Ala Ala
                275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Val Ile Gly Ile Leu
                325                 330                 335

Gly Glu Leu Asp Arg Ala Gly Leu Leu Asn Arg Asp Val Lys Asn Val
                340                 345                 350

Leu Gly Leu Thr Leu Pro Gln Thr Leu Glu Gln Tyr Asp Val Met Leu
                355                 360                 365

Thr Gln Asp Asp Ala Val Lys Asn Met Phe Arg Ala Gly Pro Ala Gly
                370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
                420                 425                 430

Gly Cys Ile Val Lys Thr Ala Gly Val Asp Asp Ser Ile Leu Lys Phe
            435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
                500                 505                 510

Asp Gly Arg Phe Ser Gly Gly Thr Ser Gly Leu Ser Ile Gly His Val
            515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
    595                 600                 605

Arg Asp Lys Ser Lys Leu Gly Gly
            610                 615

<210> SEQ ID NO 7
<211> LENGTH: 1662
<212> TYPE: DNA
<213> ORGANISM: Artificial Sequence
<220> FEATURE:
<223> OTHER INFORMATION: Codon optimized kivD gene from Lactococcus
      lactis

<400> SEQUENCE: 7
tctagacata tgtatactgt gggggattac ctgctggatc gcctgcacga actggggatt      60

-continued

| | |
|---|---|
| gaagaaattt tcggtgtgcc aggcgattat aacctgcagt tcctggacca gattatctcg | 120 |
| cacaaagata tgaagtgggt cggtaacgcc aacgaactga acgcgagcta tatggcagat | 180 |
| ggttatgccc gtaccaaaaa agctgctgcg tttctgacga cctttggcgt tggcgaactg | 240 |
| agcgccgtca acggactggc aggaagctac gccgagaacc tgccagttgt cgaaattgtt | 300 |
| gggtcgccta cttctaaggt tcagaatgaa ggcaaatttg tgcaccatac tctggctgat | 360 |
| ggggattttta acatttttat gaaaatgcat gaaccggtta ctgcggcccg cacgctgctg | 420 |
| acagcagaga atgctacggt tgagatcgac cgcgtcctgt ctgcgctgct gaaagagcgc | 480 |
| aagccggtat atatcaatct gcctgtcgat gttgccgcag cgaaagccga aaagccgtcg | 540 |
| ctgccactga aaaagaaaa cagcacctcc aatacatcgg accaggaaat tctgaataaa | 600 |
| atccaggaat cactgaagaa tgcgaagaaa ccgatcgtca tcaccggaca tgagatcatc | 660 |
| tcttttggcc tggaaaaaac ggtcacgcag ttcatttcta agaccaaact gcctatcacc | 720 |
| accctgaact tcggcaaatc tagcgtcgat gaagcgctgc cgagttttct gggtatctat | 780 |
| aatggtaccc tgtccgaacc gaacctgaaa gaattcgtcg aaagcgcgga ctttatcctg | 840 |
| atgctgggcg tgaaactgac ggatagctcc acaggcgcat ttacccacca tctgaacgag | 900 |
| aataaaatga tttccctgaa tatcgacgaa ggcaaaatct taacgagcg catccagaac | 960 |
| ttcgattttg aatctctgat tagttcgctg ctggatctgt ccgaaattga gtataaaggt | 1020 |
| aaatatattg ataaaaaaca ggaggatttt gtgccgtcta atgcgctgct gagtcaggat | 1080 |
| cgtctgtggc aagccgtaga aaacctgaca cagtctaatg aaacgattgt tgcggaacag | 1140 |
| ggaacttcat ttttcggcgc ctcatccatt tttctgaaat ccaaaagcca tttcattggc | 1200 |
| caaccgctgt gggggagtat tggttatacc tttccggcgg cgctgggttc acagattgca | 1260 |
| gataaggaat cacgccatct gctgtttatt ggtgacggca gcctgcagct gactgtccag | 1320 |
| gaactggggc tggcgatccg tgaaaaaatc aatccgattt gctttatcat caataacgac | 1380 |
| ggctacaccg tcgaacgcga aattcatgga ccgaatcaaa gttacaatga catcccgatg | 1440 |
| tggaactata gcaaactgcc ggaatccttt ggcgcgacag aggatcgcgt ggtgagtaaa | 1500 |
| attgtgcgta cggaaaacga atttgtgtcg gttatgaaag aagcgcaggc tgacccgaat | 1560 |
| cgcatgtatt ggattgaact gatcctggca aaagaaggcg caccgaaagt tctgaaaaag | 1620 |
| atggggaaac tgtttgcgga gcaaaataaa agctaaggat cc | 1662 |

<210> SEQ ID NO 8
<211> LENGTH: 548
<212> TYPE: PRT
<213> ORGANISM: Lactococcus lactis

<400> SEQUENCE: 8

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

-continued

```
Val Gly Ser Pro Thr Ser Lys Val Gln Asn Glu Gly Lys Phe Val His
            100                 105                 110
His Thr Leu Ala Asp Gly Asp Phe Lys His Phe Met Lys Met His Glu
            115                 120                 125
Pro Val Thr Ala Ala Arg Thr Leu Leu Thr Ala Glu Asn Ala Thr Val
130                 135                 140
Glu Ile Asp Arg Val Leu Ser Ala Leu Leu Lys Glu Arg Lys Pro Val
145                 150                 155                 160
Tyr Ile Asn Leu Pro Val Asp Val Ala Ala Lys Ala Glu Lys Pro
            165                 170                 175
Ser Leu Pro Leu Lys Lys Glu Asn Ser Thr Ser Asn Thr Ser Asp Gln
            180                 185                 190
Glu Ile Leu Asn Lys Ile Gln Glu Ser Leu Lys Asn Ala Lys Lys Pro
            195                 200                 205
Ile Val Ile Thr Gly His Glu Ile Ile Ser Phe Gly Leu Glu Lys Thr
            210                 215                 220
Val Thr Gln Phe Ile Ser Lys Thr Lys Leu Pro Ile Thr Thr Leu Asn
225                 230                 235                 240
Phe Gly Lys Ser Ser Val Asp Glu Ala Leu Pro Ser Phe Leu Gly Ile
            245                 250                 255
Tyr Asn Gly Thr Leu Ser Glu Pro Asn Leu Lys Glu Phe Val Glu Ser
            260                 265                 270
Ala Asp Phe Ile Leu Met Leu Gly Val Lys Leu Thr Asp Ser Ser Thr
            275                 280                 285
Gly Ala Phe Thr His His Leu Asn Glu Asn Lys Met Ile Ser Leu Asn
            290                 295                 300
Ile Asp Glu Gly Lys Ile Phe Asn Glu Arg Ile Gln Asn Phe Asp Phe
305                 310                 315                 320
Glu Ser Leu Ile Ser Ser Leu Leu Asp Leu Ser Glu Ile Glu Tyr Lys
            325                 330                 335
Gly Lys Tyr Ile Asp Lys Lys Gln Glu Asp Phe Val Pro Ser Asn Ala
            340                 345                 350
Leu Leu Ser Gln Asp Arg Leu Trp Gln Ala Val Glu Asn Leu Thr Gln
            355                 360                 365
Ser Asn Glu Thr Ile Val Ala Glu Gln Gly Thr Ser Phe Phe Gly Ala
            370                 375                 380
Ser Ser Ile Phe Leu Lys Ser Lys Ser His Phe Ile Gly Gln Pro Leu
385                 390                 395                 400
Trp Gly Ser Ile Gly Tyr Thr Phe Pro Ala Ala Leu Gly Ser Gln Ile
            405                 410                 415
Ala Asp Lys Glu Ser Arg His Leu Leu Phe Ile Gly Asp Gly Ser Leu
            420                 425                 430
Gln Leu Thr Val Gln Glu Leu Gly Leu Ala Ile Arg Glu Lys Ile Asn
            435                 440                 445
Pro Ile Cys Phe Ile Ile Asn Asn Asp Gly Tyr Thr Val Glu Arg Glu
            450                 455                 460
Ile His Gly Pro Asn Gln Ser Tyr Asn Asp Ile Pro Met Trp Asn Tyr
465                 470                 475                 480
Ser Lys Leu Pro Glu Ser Phe Gly Ala Thr Glu Asp Arg Val Val Ser
            485                 490                 495
Lys Ile Val Arg Thr Glu Asn Glu Phe Val Ser Val Met Lys Glu Ala
            500                 505                 510
```

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
        530                 535                 540

Gln Asn Lys Ser
545

<210> SEQ ID NO 9
<211> LENGTH: 1047
<212> TYPE: DNA
<213> ORGANISM: Achromobacter xylosoxidans

<400> SEQUENCE: 9

```
atgaaagctc tggtttatca cggtgaccac aagatctcgc ttgaagacaa gcccaagccc      60
acccttcaaa agcccacgga tgtagtagta cgggttttga agaccacgat ctgcggcacg     120
gatctcggca tctacaaagg caagaatcca gaggtcgccg acgggcgcat cctgggccat     180
gaagggtag cgtcatcga ggaagtgggc gagagtgtca cgcagttcaa gaaaggcgac      240
aaggtcctga tttcctgcgt cacttcttgc ggctcgtgcg actactgcaa gaagcagctt     300
tactcccatt gccgcgacgg cggtggatc ctgggttaca tgatcgatgg cgtgcaggcc      360
gaatacgtcc gcatcccgca tgccgacaac agcctctaca agatccccca gacaattgac     420
gacgaaatcg ccgtcctgct gagcgacatc ctgcccaccg ccacgaaaat cggcgtccag     480
tatgggaatg tccagccggg cgatgcggtg gctattgtcg gcgcgggccc cgtcggcatg     540
tccgtactgt tgaccgccca gttctactcc ccctcgacca tcatcgtgat cgacatggac     600
gagaatcgcc tccagctcgc caaggagctc ggggcaacgc acaccatcaa ctccggcacg     660
gagaacgttg tcgaagccgt gcataggatt gcggcagagg gagtcgatgt tgcgatcgag     720
gcggtgggca taccggcgac ttgggacatc tgccaggaga tcgtcaagcc cggcgcgcac     780
atcgccaacg tcggcgtgca tggcgtcaag gttgacttcg agattcagaa gctctggatc     840
aagaacctga cgatcaccac gggactggtg aacacgaaca cgacgcccat gctgatgaag     900
gtcgcctcga ccgacaagct tccgttgaag aagatgatta cccatcgctt cgagctggcc     960
gagatcgagc acgccatca ggtattcctc aatggcgcca aggagaaggc gatgaagatc     1020
atcctctcga acgcaggcgc tgcctga                                         1047
```

<210> SEQ ID NO 10
<211> LENGTH: 348
<212> TYPE: PRT
<213> ORGANISM: Achromobacter xylosoxidans

<400> SEQUENCE: 10

Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345

<210> SEQ ID NO 11
<211> LENGTH: 24
<212> TYPE: DNA
<213> ORGANISM: artificial sequence
<220> FEATURE:
<223> OTHER INFORMATION: primer

<400> SEQUENCE: 11
tcatcactga taacctgatt ccgg                                          24

<210> SEQ ID NO 12
<211> LENGTH: 26
<212> TYPE: DNA
<213> ORGANISM: artificial sequence
<220> FEATURE:
<223> OTHER INFORMATION: primer

<400> SEQUENCE: 12
cgagtctgtt ttggcagtca ccttaa                                        26

<210> SEQ ID NO 13
<211> LENGTH: 23
<212> TYPE: DNA
<213> ORGANISM: artificial sequence
<220> FEATURE:
<223> OTHER INFORMATION: primer

<400> SEQUENCE: 13
gagcgtgacg acgtcaactt cct                                    23

<210> SEQ ID NO 14
<211> LENGTH: 23
<212> TYPE: DNA
<213> ORGANISM: artificial sequence
<220> FEATURE:
<223> OTHER INFORMATION: primer

<400> SEQUENCE: 14
cagttcaatg ctgaaccaca cag                                    23

<210> SEQ ID NO 15
<211> LENGTH: 23
<212> TYPE: DNA
<213> ORGANISM: artificial sequence
<220> FEATURE:
<223> OTHER INFORMATION: primer

<400> SEQUENCE: 15
gaaggttgcg cctacactaa gca                                    23

<210> SEQ ID NO 16
<211> LENGTH: 23
<212> TYPE: DNA
<213> ORGANISM: artificial sequence
<220> FEATURE:
<223> OTHER INFORMATION: primer

<400> SEQUENCE: 16
gggagcggca agattaaacc agt                                    23

<210> SEQ ID NO 17
<211> LENGTH: 23
<212> TYPE: DNA
<213> ORGANISM: artificial sequence
<220> FEATURE:
<223> OTHER INFORMATION: primer

<400> SEQUENCE: 17
tggatcacgt aatcagtacc cag                                    23

<210> SEQ ID NO 18
<211> LENGTH: 23
<212> TYPE: DNA
<213> ORGANISM: artificial sequence
<220> FEATURE:
<223> OTHER INFORMATION: primer

<400> SEQUENCE: 18
atccttaact gatcggcatt gcc                                    23

<210> SEQ ID NO 19
<211> LENGTH: 30
<212> TYPE: DNA
<213> ORGANISM: artificial sequence
<220> FEATURE:
<223> OTHER INFORMATION: primer

<400> SEQUENCE: 19
ggaattcaca catgaaagct ctggtttatc                             30

<210> SEQ ID NO 20

```
<211> LENGTH: 28
<212> TYPE: DNA
<213> ORGANISM: artificial sequence
<220> FEATURE:
<223> OTHER INFORMATION: primer

<400> SEQUENCE: 20
gcgtccaggg cgtcaaagat caggcagc                                            28

<210> SEQ ID NO 21
<211> LENGTH: 30
<212> TYPE: DNA
<213> ORGANISM: artificial sequence
<220> FEATURE:
<223> OTHER INFORMATION: primer

<400> SEQUENCE: 21
gacctaggag gtcacacatg aaagctctgg                                          30

<210> SEQ ID NO 22
<211> LENGTH: 25
<212> TYPE: DNA
<213> ORGANISM: artificial sequence
<220> FEATURE:
<223> OTHER INFORMATION: primer

<400> SEQUENCE: 22
cgactctaga ggatccccgg gtacc                                               25

<210> SEQ ID NO 23
<211> LENGTH: 2283
<212> TYPE: DNA
<213> ORGANISM: Escherichia coli

<400> SEQUENCE: 23
atgtccgagc ttaatgaaaa gttagccaca gcctgggaag gttttaccaa aggtgactgg         60
cagaatgaag taaacgtccg tgacttcatt cagaaaaact acactccgta cgagggtgac        120
gagtccttcc tggctggcgc tactgaagcg accaccaccc tgtgggacaa agtaatggaa        180
ggcgttaaac tggaaaaccg cactcacgcg ccagttgact ttgacaccgc tgttgcttcc        240
accatcacct ctcacgacgc tggctacatc aacaagcagc ttgagaaaat cgttggtctg        300
cagactgaag ctccgctgaa acgtgctctt atcccgttcg gtggtatcaa aatgatcgaa        360
ggttcctgca aagcgtacaa ccgcgaactg gatccgatga tcaaaaaaat cttcactgaa        420
taccgtaaaa ctcacaacca gggcgtgttc gacgtttaca ctccggacat cctgcgttgc        480
cgtaaatctg gtgttctgac cggtctgcca gatgcatatg ccgtggccg tatcatcggt        540 gactaccgtc gcgttgcgct gtacggtatc gactacctga tgaaagacaa actggcacag        600
ttcacttctc tgcaggctga tctggaaaac ggcgtaaacc tggaacagac tatccgtctg        660
cgcgaagaaa tcgctgaaca gcaccgcgct ctgggtcaga tgaaagaaat ggctgcgaaa        720
tacggctacg acatctctgg tccggctacc aacgctcagg aagctatcca gtggacttac        780
ttcggctacc tggctgctgt taagtctcag aacggtgctg caatgtcctt cggtcgtacc        840
tccaccttcc tggatgtgta catcgaacgt gacctgaaag ctgcaagat caccgaacaa        900 gaagcgcagg aaatggttga ccacctggtc atgaaactgc gtatggttcg cttcctgcgt        960
actccggaat acgatgaact gttctctggc gacccgatct gggcaaccga atctatcggt       1020
ggtatgggcc tcgacggtcg taccctggtt accaaaaaca gcttccgttt cctgaacacc       1080
ctgtacacca tgggtccgtc tccggaaccg aacatgacca ttctgtggtc tgaaaaactg       1140
```

```
ccgctgaact tcaagaaatt cgccgctaaa gtgtccatcg acacctcttc tctgcagtat      1200
gagaacgatg acctgatgcg tccggacttc aacaacgatg actacgctat tgcttgctgc      1260
gtaagcccga tgatcgttgg taaacaaatg cagttcttcg gtgcgcgtgc aaacctggcg      1320
aaaaccatgc tgtacgcaat caacggcggc gttgacgaaa aactgaaaat gcaggttggt      1380
ccgaagtctg aaccgatcaa aggcgatgtc ctgaactatg atgaagtgat ggagcgcatg      1440
gatcacttca tggactggct ggctaaacag tacatcactg cactgaacat catccactac      1500
atgcacgaca gtacagcta cgaagcctct ctgatggcgc tgcacgaccg tgacgttatc      1560
cgcaccatgg cgtgtggtat cgctggtctg tccgttgctg ctgactccct gtctgcaatc      1620
aaatatgcga agttaaaacc gattcgtgac gaagacggtc tggctatcga cttcgaaatc      1680
gaaggcgaat acccgcagtt tggtaacaat gatccgcgtg tagatgacct ggctgttgac      1740
ctggtagaac gtttcatgaa gaaaattcag aaactgcaca cctaccgtga cgctatcccg      1800
actcagtctg ttctgaccat cacttctaac gttgtgtatg gtaagaaaac gggtaacacc      1860
ccagacggtc gtcgtgctgg cgcgccgttc ggaccgggtg ctaacccgat gcacggtcgt      1920
gaccagaaag gtgcagtagc ctctctgact tccgttgcta aactgccgtt tgcttacgct      1980
aaagatggta tctcctacac cttctctatc gttccgaacg cactgggtaa agacgacgaa      2040
gttcgtaaga ccaacctggc tggtctgatg gatggttact ccaccacga agcatccatc      2100 gaaggtggtc agcacctgaa cgttaacgtg atgaaccgtg aaatgctgct cgacgcgatg      2160
gaaaacccgg aaaaatatcc gcagctgacc atccgtgtat ctggctacgc agtacgtttc      2220
aactcgctga ctaaagaaca gcagcaggac gttattactc gtaccttcac tcaatctatg      2280
taa                                                                    2283

<210> SEQ ID NO 24
<211> LENGTH: 990
<212> TYPE: DNA
<213> ORGANISM: Escherichia coli

<400> SEQUENCE: 24
atgaaactcg ccgtttatag cacaaaacag tacgacaaga agtacctgca acaggtgaac        60
gagtcctttg gctttgagct ggaatttttt gactttctgc tgacggaaaa aaccgctaaa       120
actgccaatg gctgcgaagc ggtatgtatt ttcgtaaacg atgacggcag ccgcccggtg       180
ctggaagagc tgaaaaagca cggcgttaaa tatatcgccc tgcgctgtgc cggtttcaat       240
aacgtcgacc ttgacgcggc aaaagaactg gggctgaaag tagtccgtgt tccagcctat       300
gatccagagg ccgttgctga acacgccatc ggtatgatga tgacgctgaa ccgccgtatt       360
caccgcgcgt atcagcgtac ccgtgatgct aacttctctc tggaaggtct gaccggcttt       420
actatgtatg gcaaaacggc aggcgttatc ggtaccggta aaatcggtgt ggcgatgctg       480
cgcattctga aggttttggg tatgcgtctg ctggcgttcg atccgtatcc aagtgcagcg       540
gcgctggaac tcggtgtgga gtatgtcgat ctgccaaccc tgttctctga atcagacgtt       600
atctctctgc actgcccgct gacaccggaa actatcatcc tgttgaacga agccgccttc       660
gaacagatga aaaatggcgt gatgatcgtc aataccagtc gcggtgcatt gattgattct       720
caggcagcaa ttgaagcgct gaaaaatcag aaaattggtt cgttgggtat ggacgtgtat       780
gagaacgaac gcgatctatt ctttgaagat aaatccaacg acgtgatcca ggatgacgta       840
ttccgtcgcc tgtctgcctg ccacaacgtg ctgtttaccg gcaccaggc attcctgaca       900
```

| gcagaagctc tgaccagtat ttctcagact acgctgcaaa acttaagcaa tctggaaaaa | 960 |
| ggcgaaacct gcccgaacga actggtttaa | 990 |

<210> SEQ ID NO 25
<211> LENGTH: 2676
<212> TYPE: DNA
<213> ORGANISM: Escherichia coli

<400> SEQUENCE: 25

| atggctgtta ctaatgtcgc tgaacttaac gcactcgtag agcgtgtaaa aaaagcccag | 60 |
| cgtgaatatg ccagtttcac tcaagagcaa gtagacaaaa tcttccgcgc cgccgctctg | 120 |
| gctgctgcag atgctcgaat cccactcgcg aaaatggccg ttgccgaatc cggcatgggt | 180 |
| atcgtcgaag ataaagtgat caaaaaccac tttgcttctg aatatatcta caacgcctat | 240 |
| aaagatgaaa aacctgtggt gttctgtctg aagacgaca cttttggtac catcactatc | 300 |
| gctgaaccaa tcggtattat ttgcggtatc gttccgacca ctaacccgac ttcaactgct | 360 |
| atcttcaaat cgctgatcag tctgaagacc cgtaacgcca ttatcttctc cccgcacccg | 420 |
| cgtgcaaaag atgccaccaa caaagcggct gatatcgttc tgcaggctgc tatcgctgcc | 480 |
| ggtgctccga agatctgat cggctggatc gatcaacctt ctgttgaact gtctaacgca | 540 |
| ctgatgcacc acccagacat caacctgatc ctcgcgactg gtggtccggg catggttaaa | 600 |
| gccgcataca gctccggtaa accagctatc ggtgtaggcg cgggcaacac tccagttgtt | 660 |
| atcgatgaaa ctgctgatat caaacgtgca gttgcatctg tactgatgtc caaaaccttc | 720 |
| gacaacggcg taatctgtgc ttctgaacag tctgttgttg ttgttgactc tgtttatgac | 780 |
| gctgtacgtg aacgttttgc aacccacggc ggctatctgt tgcagggtaa agagctgaaa | 840 |
| gctgttcagg atgttatcct gaaaaacggt gcgctgaacg cggctatcgt tggtcagcca | 900 |
| gcctataaaa ttgctgaact ggcaggcttc tctgtaccag aaaacaccaa gattctgatc | 960 |
| ggtgaagtga ccgttgttga tgaaagcgaa ccgttcgcac atgaaaaact gtccccgact | 1020 |
| ctggcaatgt accgcgctaa agatttcgaa gacgcggtag aaaaagcaga gaaactggtt | 1080 |
| gctatgggcg gtatcggtca tacctcttgc ctgtacactg accaggataa ccaaccggct | 1140 |
| cgcgtttctt acttcggtca gaaaatgaaa acggcgcgta tcctgattaa cacccccagcg | 1200 |
| tctcagggtg gtatcggtga cctgtataac ttcaaactcg caccttccct gactctgggt | 1260 |
| tgtggttctt ggggtggtaa ctccatctct gaaaacgttg gtccgaaaca cctgatcaac | 1320 |
| aagaaaaccg ttgctaagcg agctgaaaac atgttgtggc acaaacttcc gaaatctatc | 1380 |
| tacttccgcc gtgggctccct gccaatcgcg ctggatgaag tgattactga tggccacaaa | 1440 |
| cgtgcgctca tcgtgactga ccgcttcctg ttcaacaatg ttatgctga tcagatcact | 1500 |
| tccgtactga aagcagcagg cgttgaaact gaagtcttct tcgaagtaga agcggaccccg | 1560 |
| acccctgagca tcgttcgtaa aggtgcagaa ctggcaaact ccttcaaacc agacgtgatt | 1620 |
| atcgcgctgg gtggtggttc cccgatggac gccgcgaaga tcatgtgggt tatgtacgaa | 1680 |
| catccggaaa ctcacttcga agagctggcg ctgcgcttta tggatatccg taacgtatc | 1740 |
| tacaagttcc cgaaaatggg cgtgaaagcg aaaatgatcg ctgtcaccac cacttctggt | 1800 |
| acaggttctg aagtcactcc gtttgcggtt gtaactgacg acgctactgg tcagaaatat | 1860 |
| ccgctggcag actatgcgct gactccggat atggcgattg tcgacgccaa cctggttatg | 1920 |
| gacatgccga gtccctgtg tgctttcggt ggtctgacg cagtaactca cgccatggaa | 1980 |
| gcttatgttt ctgtactggc atctgagttc tctgatggtc aggctctgca ggcactgaaa | 2040 |

```
ctgctgaaag aatatctgcc agcgtcctac cacgaagggt ctaaaaatcc ggtagcgcgt    2100
gaacgtgttc acagtgcagc gactatcgcg ggtatcgcgt ttgcgaacgc cttcctgggt    2160
gtatgtcact caatggcgca caaactgggt tcccagttcc atattccgca cggtctggca    2220
aacgccctgc tgatttgtaa cgttattcgc tacaatgcga acgacaaccc gaccaagcag    2280
actgcattca gccagtatga ccgtccgcag gctcgccgtc gttatgctga aattgccgac    2340
cacttgggtc tgagcgcacc gggcgaccgt actgctgcta agatcgagaa actgctggca    2400
tggctggaaa cgctgaaagc tgaactgggt attccgaaat ctatccgtga agctggcgtt    2460
caggaagcag acttcctggc gaacgtggat aaactgtctg aagatgcatt cgatgaccag    2520
tgcaccggcg ctaacccgcg ttacccgctg atctccgagc tgaaacagat tctgctggat    2580
acctactacg gtcgtgatta tgtagaaggt gaaactgcag cgaagaaaga agctgctccg    2640
gctaaagctg agaaaaaagc gaaaaaatcc gcttaa                              2676
```

<210> SEQ ID NO 26
<211> LENGTH: 1809
<212> TYPE: DNA
<213> ORGANISM: Escherichia coli

<400> SEQUENCE: 26

```
gtgcaaacct ttcaagccga tcttgccatt gtaggcgccg gtggcgcggg attacgtgct      60
gcaattgctg ccgcgcaggc aaatccgaat gcaaaaatcg cactaatctc aaaagtatac     120
ccgatgcgta gccataccgt tgctgcagaa ggggctccg ccgctgtcgc gcaggatcat      180
gacagcttcg aatatcactt tcacgataca gtagcgggtg gcgactggtt gtgtgagcag     240
gatgtcgtgg attatttcgt ccaccactgc ccaaccgaaa tgacccaact ggaactgtgg     300 ggatgccat ggagccgtcg cccggatggt agcgtcaacg tacgtcgctt cggcggcatg      360
aaaatcgagc gcacctggtt cgccgccgat aagaccggct tccatatgct gcacacgctg     420
ttccagacct ctctgcaatt cccgcagatc cagcgttttg acgaacattt cgtgctggat     480
attctggttg atgatggtca tgttcgcggc ctggtagcaa tgaacatgat ggaaggcacg     540
ctggtgcaga tccgtgctaa cgcggtcgtt atggctactg gcgtgcggg tcgcgtttat      600 cgttacaaca ccaacggcgg catcgttacc ggtgacggta tgggtatggc gctaagccac     660
ggcgttccgc tgcgtgacat ggaattcgtt cagtatcacc caaccggtct gccaggttcc     720
ggtatcctga tgaccgaagg ttgccgcggt gaaggcggta ttctggtcaa caaaaatggc     780
taccgttatc tgcaagatta cggcatgggc cggaaactc gctgggcga ccgaaaaac       840 aaatatatgg aactgggtcc acgcgacaaa gtctctcagg ccttctggca cgaatggcgt     900
aaaggcaaca ccatctccac gccgcgtggc gatgtggttt atctcgactt cgtcacctc     960 ggcgagaaaa aactgcatga acgtctgccg ttcatctgcg aactggcgaa agcgtacgtt    1020
ggcgtcgatc cggttaaaga accgattccg gtacgtccga ccgcacacta ccatgggc     1080 ggtatcgaaa ccgatcagaa ctgtgaaacc cgcattaaag gtctgttcgc cgtgggtgaa    1140
tgttcctctg ttggtctgca cggtgcaaac cgtctgggtt ctaactccct ggcggaactg    1200
gtggtcttcg gccgtctggc cggtgaacaa gcgacagagc gtgcagcaac tgccggtaat    1260
ggcaacgaag cggcaattga agcgcaggca gctggcgttg aacaacgtct gaaagatctg    1320 gttaaccagat ggcggcga aaactggcg aagatccgcg acgaaatggg cctggctatg     1380
gaagaaggct gcggtatcta ccgtacgccg gaactgatgc agaaaaccat cgacaagctg    1440
```

-continued

```
gcagagctgc aggaacgctt caagcgcgtg cgcatcaccg acacttccag cgtgttcaac      1500
accgacctgc tctacaccat tgaactgggc cacggtctga acgttgctga atgtatggcg      1560
cactccgcaa tggcacgtaa agagtcccgc ggcgcgcacc agcgtctgga cgaaggttgc      1620
accgagcgtg acgacgtcaa cttcctcaaa cacaccctcg ccttccgcga tgctgatggc      1680
acgactcgcc tggagtacag cgacgtgaag attactacgc tgccgccagc taaacgcgtt      1740
tacggtggcg aagcggatgc agccgataag gcggaagcag ccaataagaa ggagaaggcg      1800
aatggctga                                                             1809
```

<210> SEQ ID NO 27
<211> LENGTH: 735
<212> TYPE: DNA
<213> ORGANISM: Escherichia coli

<400> SEQUENCE: 27

```
atggctgaga tgaaaaacct gaaaattgag gtggtgcgct ataacccgga agtcgatacc       60
gcaccgcata gcgcattcta tgaagtgcct tatgacgcaa ctacctcatt actgatgcg      120 ctgggctaca tcaaagacaa cctggcaccg gacctgagct accgctggtc ctgccgtatg      180
gcgatttgtg gttcctgcgg catgatggtt aacaacgtgc aaaaactggc atgtaaaacc      240
ttcctgcgtg attacaccga cggtatgaag gttgaagcgt tagctaactt cccgattgaa      300
cgcgatctgg tggtcgatat gacccacttc atcgaaagtc tggaagcgat caaaccgtac      360
atcatcggca actcccgcac cgcggatcag ggtactaaca tccagacccc ggcgcagatg      420
gcgaagtatc accagttctc cggttgcatc aactgtggtt tgtgctacgc cgcgtgcccg      480
cagtttggcc tgaacccaga gttcatcggt ccggctgcca ttacgctggc catcgttat      540 aacgaagata gccgcgacca cggtaagaag gagcgtatgg cgcagttgaa cagccagaac      600
ggcgtatgga gctgtacttt cgtgggctac tgctccgaag tctgcccgaa acacgtcgat      660
ccggctgcgg ccattcagca gggcaaagta gaaagttcga agactttcct tatcgcgacc      720
ctgaaaccac gctaa                                                      735
```

<210> SEQ ID NO 28
<211> LENGTH: 396
<212> TYPE: DNA
<213> ORGANISM: Escherichia coli

<400> SEQUENCE: 28

```
atgacgacta aacgtaaacc gtatgtacgg ccaatgacgt ccacctggtg gaaaaaattg       60 ccgtttttatc gcttttacat gctgcgcgaa ggcacggcgg ttccggctgt gtggttcagc      120
attgaactga ttttcgggct gtttgccctg aaaaatggcc cggaagcctg gcgggattc       180 gtcgactttt tacaaaaccc ggttatcgtg atcattaacc tgatcactct ggcggcagct      240
ctgctgcaca ccaaaacctg gtttgaactg gcaccgaaag cggccaatat cattgtaaaa      300
gacgaaaaaa tgggaccaga gccaattatc aaaagtctct gggcggtaac tgtggttgcc      360
accatcgtaa tcctgtttgt tgccctgtac tggtaa                               396
```

<210> SEQ ID NO 29
<211> LENGTH: 360
<212> TYPE: DNA
<213> ORGANISM: Escherichia coli

<400> SEQUENCE: 29

```
atgattaatc caaatccaaa gcgttctgac gaaccggtat tctgggggcct cttcggggcc       60
```

```
ggtggtatgt ggagcgccat cattgcgccg gtgatgatcc tgctggtggg tattctgctg      120
ccactggggt tgtttccggg tgatgcgctg agctacgagc gcgttctggc gttcgcgcag      180
agcttcattg gtcgcgtatt cctgttcctg atgatcgttc tgccgctgtg gtgtggttta      240
caccgtatgc accacgcgat gcacgatctg aaaatccacg tacctgcggg caaatgggtt      300
ttctacggtc tggctgctat cctgacagtt gtcacgctga ttggtgtcgt tacaatctaa      360

<210> SEQ ID NO 30
<211> LENGTH: 16387
<212> TYPE: DNA
<213> ORGANISM: artificial sequence
<220> FEATURE:
<223> OTHER INFORMATION: plasmid construct

<400> SEQUENCE: 30
tcccattacc gacatttggg cgctatacgt gcatatgttc atgtatgtat ctgtatttaa       60 aacactttg tattattttt cctcatatat gtgtataggt ttatacggat gatttaatta      120
ttacttcacc accctttatt tcaggctgat atcttagcct tgttactagt tagaaaaaga      180
catttttgct gtcagtcact gtcaagagat tcttttgctg gcatttcttc tagaagcaaa      240
aagagcgatg cgtctttttcc gctgaaccgt tccagcaaaa aagactacca acgcaatatg      300
gattgtcaga atcatataaa agagaagcaa ataactcctt gtcttgtatc aattgcatta      360
taatatcttc ttgttagtgc aatatcatat agaagtcatc gaaatagata ttaagaaaaa      420
caaactgtac aatcaatcaa tcaatcatcg ctgaggatgt tgacaaaagc aacaaaagaa      480
caaaaatccc ttgtgaaaaa cagaggggcg agcttgttg ttgattgctt agtggagcaa      540
ggtgtcacac atgtatttgg cattccaggt gcaaaaattg atgcggtatt tgacgcttta      600
caagataaag gacctgaaat tatcgttgcc cggcacgaac aaaacgcagc attcatggcc      660
caagcagtcg gccgttaac tggaaaaccg ggagtcgtgt tagtcacatc aggacccggt      720
gcctctaact tggcaacagg cctgctgaca gcgaacactg aaggagaccc tgtcgttgcg      780
cttgctggaa acgtgatccg tgcagatcgt ttaaaacgga cacatcaatc tttggataat      840
gcggcgctat tccagccgat tacaaaatac agtgtagaag ttcaagatgt aaaaaatata      900
ccggaagctg ttacaaatgc atttaggata gcgtcagcag gcaggctgg ggccgctttt      960 gtgagctttc gcaagatgt tgtgaatgaa gtcacaaata cgaaaaacgt gcgtgctgtt     1020
gcagcgccaa aactcggtcc tgcagcagat gatgcaatca gtgcggccat agcaaaaatc     1080
caaacagcaa aacttcctgt cgttttggtc ggcatgaaag gcggaagacc ggaagcaatt     1140
aaagcggttc gcaagctttt gaaaaaggtt cagcttccat tgttgaaac atatcaagct     1200 gccggtaccc tttctagaga tttagaggat caatattttg gccgtatcgg tttgttccgc     1260
aaccagcctg gcgatttact gctagagcag gcagatgttg ttctgacgat cggctatgac     1320
ccgattgaat atgatccgaa attctggaat atcaatggag accggacaat tatccattta     1380
gacgagatta tcgctgacat tgatcatgct taccagcctg atcttgaatt gatcggtgac     1440
attccgtcca cgatcaatca tatcgaacac gatgctgtga agtggaatt tgcagagcgt     1500 gagcagaaaa tccttctga tttaaaacaa tatatgcatg aaggtgagca ggtgcctgca     1560
gattggaaat cagacagagc gcaccctctt gaaatcgtta agagttgcg taatgcagtc     1620 gatgatcatg ttacagtaac ttgcgatatc ggttcgcacg ccatttggat gtcacgttat     1680
ttccgcagct acgagccgtt aacattaatg atcagtaacg gtatgcaaac actcggcgtt     1740
```

```
gcgcttcctt gggcaatcgg cgcttcattg gtgaaaccgg gagaaaaagt ggtttctgtc    1800
tctggtgacg gcggtttctt attctcagca atggaattag agacagcagt tcgactaaaa    1860
gcaccaattg tacacattgt atggaacgac agcacatatg acatggttgc attccagcaa    1920
ttgaaaaaat ataaccgtac atctgcggtc gatttcggaa atatcgatat cgtgaaatat    1980
gcggaaagct tcggagcaac tggcttgcgc gtagaatcac cagaccagct ggcagatgtt    2040
ctgcgtcaag gcatgaacgc tgaaggtcct gtcatcatcg atgtcccggt tgactacagt    2100
gataacatta atttagcaag tgacaagctt ccgaaagaat tcggggaact catgaaaacg    2160
aaagctctct agttaattaa tcatgtaatt agttatgtca cgcttacatt cacgccctcc    2220
ccccacatcc gctctaaccg aaaaggaagg agttagacaa cctgaagtct aggtccctat    2280
ttattttttt atagttatgt tagtattaag aacgttattt atatttcaaa tttttcttt    2340 ttttctgtac agacgcgtgt acgcatgtaa cattatactg aaaaccttgc ttgagaaggt    2400
tttgggacgc tcgaaggctt taatttgcgg gcggccgctc tagaactagt accacaggtg    2460
ttgtcctctg aggacataaa atacacaccg agattcatca actcattgct ggagttagca    2520
tatctacaat tgggtgaaat ggggagcgat ttgcaggcat ttgctcggca tgccggtaga    2580
ggtgtggtca ataagagcga cctcatgcta tacctgagaa agcaacctga cctacaggaa    2640
agagttactc aagaataaga atttttcgttt taaaacctaa gagtcacttt aaaatttgta    2700
tacacttatt ttttttataa cttatttaat aataaaaatc ataaatcata agaaattcgc    2760
ttactcttaa ttaatcaagc atctaaaaca caaccgttgg aagcgttgga aaccaactta    2820
gcatacttgg atagagtacc tcttgtgtaa cgaggtggag gtgcaaccca actttgttta    2880
cgttgagcca tttccttatc agagactaat aggtcaatct tgttattatc agcatcaatg    2940
ataatctcat cgccgtctct gaccaacccg ataggaccac cttcagcggc ttcgggaaca    3000
atgtggccga ttaagaaccc gtgagaacca ccagagaatc taccatcagt caacaatgca    3060
acatctttac ccaaaccgta acccatcaga gcagaggaag gctttagcat ttcaggcata    3120
cctggtgcac ctcttggacc ttcatatctg ataacaacaa cggttttttc acccttcttg    3180
atttcacctc tttccaaggc ttcaataaag gcaccttcct cttcgaacac acgtgctcta    3240
cccttgaagt aagtaccttc cttaccggta atttacccca cagctccacc tggtgccaat    3300
gaaccgtaca gaatttgcaa gtgaccgttg gccttgattg ggtgggagag tggcttaata    3360
atctcttgtc cttcaggtag gcttggtgct ttctttgcac gttctgccaa agtgtcaccg    3420
gtaacagtca ttgtgttacc gtgcaacatg ttgttttcat atagatactt aatcacagat    3480
tgggtaccac caacgttaat caaatcggcc atgacgtatt taccagaagg tttgaagtca    3540
ccgatcaatg gtgtagtatc actgattctt tggaaatcat ctggtgacaa cttgacaccc    3600
gcagagtgag caacagccac caaatgcaaa acagcattag tggacccacc ggttgcaacg    3660
acataagtaa tggcgttttc aaaagcctct tttgtgagga tatcacgagg taaaataccc    3720
aattccattg tcttcttgat gtattcacca atgttgtcac actcagctaa cttctcccttg   3780 gaaacggctg ggaaggaaga ggagtttgga atggtcaaac ctagcacttc agcggcagaa    3840
gccattgtgt tggcagtata cataccacca caagaaccag gacctgggca tgcatgttcc    3900
acaacatctt ctcttcttc ttcagtgaat tgcttggaaa tatattcacc gtaggattgg    3960
aacgcagaga cgatatcgat gttttttagag atcctgttaa aacctctagt ggagtagtag    4020
atgtaatcaa tgaagcggaa gccaaaagac cagagtagag gcctatagaa gaaactgcga    4080
taccttttgt gatggctaaa caaacagaca tctttttata tgttttact tctgtatatc    4140
```

```
gtgaagtagt aagtgataag cgaatttggc taagaacgtt gtaagtgaac aagggacctc    4200
ttttgccttt caaaaaagga ttaaatggag ttaatcattg agatttagtt ttcgttagat    4260
tctgtatccc taaataactc ccttacccga cgggaaggca caaaagactt gaataatagc    4320
aaacggccag tagccaagac caaataatac tagagttaac tgatggtctt aaacaggcat    4380
tacgtggtga actccaagac caatatacaa aatatcgata agttattctt gcccaccaat    4440
ttaaggagcc tacatcagga cagtagtacc attcctcaga gaagaggtat acataacaag    4500
aaaatcgcgt gaacacctta tataacttag cccgttattg agctaaaaaa ccttgcaaaa    4560
tttcctatga ataagaatac ttcagacgtg ataaaaattt actttctaac tcttctcacg    4620
ctgcccctat ctgttcttcc gctctaccgt gagaaataaa gcatcgagta cggcagttcg    4680
ctgtcactga actaaaacaa taaggctagt tcgaatgatg aacttgcttg ctgtcaaact    4740
tctgagttgc cgctgatgtg acactgtgac aataaattca aaccggttat agcggtctcc    4800
tccggtaccg gttctgccac ctccaataga gctcagtagg agtcagaacc tctgcggtgg    4860
ctgtcagtga ctcatccgcg tttcgtaagt tgtgcgcgtg cacatttcgc ccgttcccgc    4920
tcatcttgca gcaggcggaa attttcatca cgctgtagga cgcaaaaaaa aaataattaa    4980
tcgtacaaga atcttggaaa aaaaattgaa aaattttgta taaagggat gacctaactt    5040 gactcaatgg cttttacacc cagtattttc cctttccttg tttgttacaa ttatagaagc    5100
aagacaaaaa catatagaca acctattcct aggagttata ttttttttacc ctaccagcaa    5160 tataagtaaa aaactagtat gaaggtgttt tacgataaag actgcgatct gagcatcatc    5220
cagggaaaga aggttgctat tataggatat ggttcccaag gacacgcaca agccttgaac    5280
ttgaaagatt ctggggtcga cgtgacagta ggtctgtata aggtgctgc tgatgcagca    5340 aaggctgaag cacatggctt taaagtcaca gatgttgcag cggctgttgc tggcgctgat    5400
ttagtcatga tttaattcc agatgaattt caatcgcaat tgtacaaaaa tgaaatagaa    5460
ccaaacatta agaagggcgc taccttggcc ttcagtcatg gatttgccat tcattacaat    5520
caagtagtcc ccagggcaga tttggacgtt attatgattg cacctaaggc tccggggcat    5580
actgttagga gcgaatttgt taagggtggt ggtattccag atttgatcgc tatataccaa    5640
gacgttagcg gaaacgctaa gaatgtagct ttaagctacg cagcaggagt tggtggcggg    5700
agaacgggta atatagaaac cacttttaaa gacgagactg agacagattt atttggagaa    5760
caagcggttc tgtgcggagg aactgttgaa ttggttaaag caggctttga gacgcttgtc    5820
gaagcagggt acgctcccga aatggcatac ttcgaatgtc tacatgaatt gaagttgata    5880
gtagacttaa tgtatgaagg tggtatagct aatatgaact attccatttc aaataatgca    5940
gaatatggtg agtatgtcac cggacctgaa gtcattaacg cagaatcaag acaagccatg    6000
agaaatgcct tgaaacgtat ccaggacggt gaatacgcta agatgttcat aagtgaaggc    6060
gctacgggtt acccgagtat gactgctaaa agaagaaaca atgcagcaca tggtatcgaa    6120
attattggtg aacagttaag gtctatgatg ccctggatcg gtgctaataa gatcgtagac    6180
aaggcgaaaa attaaggccc tgcaggccta tcagtgctg gaaactttt ctcttggaat    6240 ttttgcaaca tcagtcata gtcaattgaa ttgacccaat ttcacattta agatttttt    6300 tttttcatcc gacatacatc tgtacactag gaagccctgt ttttctgaag cagcttcaaa    6360
tatatatatt ttttacatat ttattatgat tcaatgaaca atctaattaa atcgaaaaca    6420
agaaccgaaa cgcgaataaa taatttattt agatggtgac aagtgtataa gtcctcatcg    6480
```

```
ggacagctac gatttctctt tcggttttgg ctgagctact ggttgctgtg acgcagcggc    6540
attagcgcgg cgttatgagc taccctcgtg gcctgaaaga tggcgggaat aaagcggaac    6600
taaaaattac tgactgagcc atattgaggt caatttgtca actcgtcaag tcacgtttgg    6660
tggacggccc ctttccaacg aatcgtatat actaacatgc gcgcgcttcc tatatacaca    6720
tatacatata tatatatata tatatgtgtg cgtgtatgtg tacacctgta tttaatttcc    6780
ttactcgcgg gttttctttt tttctcaatt cttggcttcc tctttctcga gtatataatt    6840
tttcaggtaa aatttagtac gatagtaaaa tacttctcga actcgtcaca tatacgtgta    6900
cataatgtct gaaccagctc aaaagaaaca aaaggttgct aacaactctc tagagcggcc    6960
gcccgcaaat taaagccttc gagcgtccca aaaccttctc aagcaaggtt ttcagtataa    7020
tgttacatgc gtacacgcgt ctgtacagaa aaaaagaaa aatttgaaat ataaataacg    7080
ttcttaatac taacataact ataaaaaaat aaatagggac ctagacttca ggttgtctaa    7140
ctccttcctt ttcggttaga gcggatgtgg ggggagggcg tgaatgtaag cgtgacataa    7200 ctaattcat gattaattaa ttattggttt tctggtctca actttctgac ttccttacca     7260
accttccaga tttccatgtt tctgatggtg tctaattcct tttctagctt ttctctgtag    7320
tcaggttgag agttgaattc caaagatctc ttggtttcgg taccgttctt ggtagattcg    7380
tacaagtctt ggaaaacagg cttcaaagca ttcttgaaga ttgggtacca gtccaaagca    7440
cctcttctgg cggtggtgga acaagcatcg tacatgtaat ccataccgta cttaccgatc    7500
aatgggtata gagattgggt agcttcttcg acggtttcgt tgaaagcttc agatggggag    7560
tgaccgtttt ctctcaagac gtcgtattga gccaagaaca taccgtggat accacccatt    7620
aaacaacctc tttcaccgta caagtcagag ttgacttctc tttcgaaagt ggtttggtaa    7680
acgtaaccga aaccaatggc aacggccaaa gcttgggcct tttcgtgagc cttaccggtg    7740
acatcgttcc agacggcgta agaagagtta ataccacgac cttccttgaa caaagatctg    7800
acagttctac cggaacccct tggagcaacc aagataacat ctaagtcctt tggtggttca    7860
acgtgagtca agtccttgaa gactggggag aaaccgtggg agaagtacaa agtcttaccc    7920
ttggtcaaca atggcttgat agcaggccag gtttctgatt gagcggcatc ggacaacaag    7980
ttcataacgt aactacctct cttgatagca tcttcaacag tgaacaagtt cttgcctgga    8040
acccaaccgt cttcgatggc agccttccaa gaagcaccat cttttacggac accaatgata    8100 acgttcaaac cgttgtctct caagttcaaa ccttgaccgt aaccttggga accgtaaccg    8160
atcaaagcaa aagtgtcgtt cttgaagtag tccaacaact tttctcttgg ccagtcagct    8220 cttttcgtaga cggtttcaac agtaccaccg aagttgattt gcttcaacat cctcagctct    8280
agatttgaat atgtattact tggttatggt tatatatgac aaaagaaaaa gaagaacaga    8340
agaataacgc aaggaagaac aataactgaa attgatagag aagtattatg tctttgtctt    8400
tttataataa atcaagtgca gaaatccgtt agacaacatg agggataaaa tttaacgtgg    8460
gcgaagaaga aggaaaaaag ttttgtgag ggcgtaattg aagcgatctg ttgattgtag    8520 atttttttttt tttgaggagt caaagtcaga agagaacaga caaatggtat taaccatcca    8580
atactttttt ggagcaacgc taagctcatg cttttccatt ggttacgtgc tcagttgtta    8640
gatatggaaa gagaggatgc tcacggcagc gtgactccaa ttgagcccga aagagaggat    8700
gccacgtttt cccgacggct gctagaatgg aaaaaggaaa aatagaagaa tcccattcct    8760
atcattattt acgtaatgac ccacacattt ttgagatttt caactattac gtattacgat    8820
aatcctgctg tcattatcat tattatctat atcgacgtat gcaacgtatg tgaagccaag    8880
```

```
taggcaatta tttagtactg tcagtattgt tattcatttc agatctatcc gcggtggagc   8940
tcgaattcac tggccgtcgt tttacaacgt cgtgactggg aaaaccctgg cgttacccaa   9000
cttaatcgcc ttgcagcaca tccccctttc gccagctggc gtaatagcga agaggcccgc   9060
accgatcgcc cttcccaaca gttgcgcagc ctgaatggcg aatggcgcct gatgcggtat   9120
tttctcctta cgcatctgtg cggtatttca caccgcatac gtcaaagcaa ccatagtacg   9180
cgccctgtag cggcgcatta agcgcggcgg gtgtggtggt tacgcgcagc gtgaccgcta   9240
cacttgccag cgccttagcg cccgctcctt tcgctttctt cccttccttt ctcgccacgt   9300
tcgccggctt tccccgtcaa gctctaaatc ggggggctccc tttagggttc cgatttagtg   9360
ctttacggca cctcgacccc aaaaaacttg atttgggtga tggttcacgt agtgggccat   9420
cgccctgata cacggttttt cgccctttga cgttggagtc cacgttcttt aatagtggac   9480
tcttgttcca aactggaaca acactcaact ctatctcggg ctattctttt gatttataag   9540
ggattttgcc gatttcggtc tattggttaa aaaatgagct gatttaacaa aaatttaacg   9600
cgaattttaa caaaatatta cgtttacaa ttttatggtg cactctcagt acaatctgct   9660
ctgatgccgc atagttaagc cagccccgac acccgccaac accgctgac gcgccctgac    9720 gggcttgtct gctcccggca tccgcttaca gacaagctgt gaccgtctcc gggagctgca   9780
tgtgtcagag gttttcaccg tcatcaccga acgcgcgag acgaaagggc ctcgtgatac    9840
gcctattttt ataggttaat gtcatgataa taatggtttc ttagacgtca ggtggcactt   9900
ttcggggaaa tgtgcgcgga accccctattt gtttattttt ctaaatacat tcaaatatgt   9960
atccgctcat gagacaataa ccctgataaa tgcttcaata atattgaaaa aggaagagta  10020
tgagtattca acatttccgt gtcgccctta ttccctttt tgcggcattt tgccttcctg   10080 ttttttgctca cccagaaacg ctggtgaaag taaaagatgc tgaagatcag ttgggtgcac   10140
gagtgggtta catcgaactg gatctcaaca gcggtaagat ccttgagagt tttcgccccg   10200
aagaacgttt tccaatgatg agcactttta aagttctgct atgtggcgcg gtattatccc   10260
gtattgacgc cgggcaagag caactcggtc gccgcataca ctattctcag aatgacttgg   10320
ttgagtactc accagtcaca gaaaagcatc ttacggatgg catgacagta agagaattat   10380
gcagtgctgc cataaccatg agtgataaca ctgcggccaa cttacttctg acaacgatcg   10440
gaggaccgaa ggagctaacc gcttttttgc acaacatggg ggatcatgta actcgccttg   10500
atcgttggga accggagctg aatgaagcca taccaaacga cgagcgtgac accacgatgc   10560
ctgtagcaat ggcaacaacg ttgcgcaaac tattaactgg cgaactactt actctagctt   10620
cccggcaaca attaatagac tggatggagg cggataaagt tgcaggacca cttctgcgct   10680
cggcccttcc ggctggctgg tttattgctg ataaatctgg agccggtgag cgtgggtctc   10740
gcggtatcat tgcagcactg gggccagatg gtaagccctc ccgtatcgta gttatctaca   10800
cgacggggag tcaggcaact atggatgaac gaaatagaca gatcgctgag ataggtgcct   10860
cactgattaa gcattggtaa ctgtcagacc aagtttactc atatatactt tagattgatt   10920
taaaacttca ttttaatttt aaaaggatct aggtgaagat cctttttgat aatctcatga   10980
ccaaaatccc ttaacgtgag ttttcgttcc actgagcgtc agaccccgta gaaaagatca  11040
aaggatcttc ttgagatcct ttttttctgc gcgtaatctg ctgcttgcaa acaaaaaaac  11100
caccgctacc agcggtggtt tgtttgccgg atcaagagct accaactctt tttccgaagg  11160
taactggctt cagcagagcg cagataccaa atactgttct tctagtgtag ccgtagttag  11220
```

```
gccaccactt caagaactct gtagcaccgc ctacatacct cgctctgcta atcctgttac   11280
cagtggctgc tgccagtggc gataagtcgt gtcttaccgg gttggactca agacgatagt   11340
taccggataa ggcgcagcgg tcgggctgaa cgggggggttc gtgcacacag cccagcttgg   11400
agcgaacgac ctacaccgaa ctgagatacc tacagcgtga gctatgagaa agcgccacgc   11460
ttcccgaagg gagaaaggcg gacaggtatc cggtaagcgg cagggtcgga acaggagagc   11520
gcacgaggga gcttccaggg ggaaacgcct ggtatcttta tagtcctgtc gggtttcgcc   11580
acctctgact tgagcgtcga ttttttgtgat gctcgtcagg ggggcggagc ctatggaaaa   11640
acgccagcaa cgcggccttt ttacggttcc tggccttttg ctggcctttt gctcacatgt   11700
tctttcctgc gttatcccct gattctgtgg ataaccgtat taccgccttt gagtgagctg   11760
ataccgctcg ccgcagccga acgaccgagc gcagcgagtc agtgagcgag gaagcggaag   11820
agcgcccaat acgcaaaccg cctctccccg cgcgttggcc gattcattaa tgcagctggc   11880
acgacaggtt tcccgactgg aaagcgggca gtgagcgcaa cgcaattaat gtgagttagc   11940
tcactcatta ggcaccccag gctttacact ttatgcttcc ggctcgtatg ttgtgtggaa   12000
ttgtgagcgg ataacaattt cacacaggaa acagctatga ccatgattac gccaagcttt   12060 ttcttttccaa ttttttttttt ttcgtcatta taaaaatcat tacgaccgag attcccgggt   12120
aataactgat ataattaaat tgaagctcta atttgtgagt ttagtataca tgcatttact   12180
tataatacag tttttttagtt ttgctggccg catcttctca aatatgcttc ccagcctgct   12240
tttctgtaac gttcaccctc taccttagca tcccttccct ttgcaaatag tcctcttcca   12300
acaataataa tgtcagatcc tgtagagacc acatcatcca cggttctata ctgttgaccc   12360
aatgcgtctc ccttgtcatc taaacccaca ccgggtgtca taatcaacca atcgtaacct   12420
tcatctcttc cacccatgtc tctttgagca ataaagccga taacaaaatc tttgtcgctc   12480
ttcgcaatgt caacagtacc cttagtatat tctccagtag atagggagcc cttgcatgac   12540
aattctgcta acatcaaaag gcctctaggt tcctttgtta cttcttctgc cgcctgcttc   12600
aaaccgctaa caatacctgg gcccaccaca ccgtgtgcat tcgtaatgtc tgcccattct   12660
gctattctgt atacacccgc agagtactgc aatttgactg tattaccaat gtcagcaaat   12720
tttctgtctt cgaagagtaa aaaattgtac ttggcggata atgcctttag cggcttaact   12780
gtgccctcca tggaaaaatc agtcaagata tccacatgtg ttttttagtaa acaaattttg   12840 ggacctaatg cttcaactaa ctccagtaat tccttggtgg tacgaacatc caatgaagca   12900
cacaagtttg tttgcttttc gtgcatgata ttaaatagct tggcagcaac aggactagga   12960
tgagtagcag cacgttcctt atatgtagct ttcgacatga tttatcttcg tttcctgcag   13020 gttttttgttc tgtgcagttg ggttaagaat actgggcaat ttcatgtttc ttcaacacta   13080
catatgcgta tatataccaa tctaagtctg tgctccttcc ttcgttcttc cttctgttcg   13140
gagattaccg aatcaaaaaa atttcaagga aaccgaaatc aaaaaaaaga ataaaaaaaa   13200
aatgatgaat tgaaaagctt gcatgcctgc aggtcgactc tagtatactc cgtctactgt   13260
acgatacact tccgctcagg tccttgtcct ttaacgaggc cttaccactc ttttgttact   13320
ctattgatcc agctcagcaa aggcagtgtg atctaagatt ctatcttcgc gatgtagtaa   13380
aactagctag accgagaaag agactagaaa tgcaaaaggc acttctacaa tggctgccat   13440
cattattatc cgatgtgacg ctgcattttt tttttttttt tttttttttt tttttttttt   13500
tttttttttt ttttttgta caaatatcat aaaaaaagag aatcttttta agcaaggatt   13560
ttcttaactt cttcggcgac agcatcaccg acttcggtgg tactgttgga accacctaaa   13620
```

```
tcaccagttc tgatacctgc atccaaaacc tttttaactg catcttcaat ggctttacct   13680
tcttcaggca agttcaatga caatttcaac atcattgcag cagacaagat agtggcgata   13740
gggttgacct tattctttgg caaatctgga gcggaaccat ggcatggttc gtacaaacca   13800
aatgcggtgt tcttgtctgg caaagaggcc aaggacgcag atggcaacaa acccaaggag   13860
cctgggataa cggaggcttc atcggagatg atatcaccaa acatgttgct ggtgattata   13920
ataccattta ggtgggttgg gttcttaact aggatcatgg cggcagaatc aatcaattga   13980
tgttgaactt tcaatgtagg gaattcgttc ttgatggttt cctccacagt ttttctccat   14040
aatcttgaag aggccaaaac attagcttta tccaaggacc aaataggcaa tggtggctca   14100
tgttgtaggg ccatgaaagc ggccattctt gtgattcttt gcacttctgg aacggtgtat   14160
tgttcactat cccaagcgac accatcacca tcgtcttcct ttctcttacc aaagtaaata   14220
cctcccacta attctctaac aacaacgaag tcagtacctt tagcaaattg tggcttgatt   14280
ggagataagt ctaaaagaga gtcggatgca aagttacatg gtcttaagtt ggcgtacaat   14340
tgaagttctt tacggatttt tagtaaacct tgttcaggtc taacactacc ggtacccat    14400 ttaggaccac ccacagcacc taacaaaacg gcatcagcct tcttggaggc ttccagcgcc   14460
tcatctggaa gtggaacacc tgtagcatcg atagcagcac caccaattaa atgattttcg   14520
aaatcgaact tgacattgga acgaacatca gaaatagctt taagaaccct aatggcttcg   14580
gctgtgattt cttgaccaac gtggtcacct ggcaaaacga cgatcttctt aggggcagac   14640
attacaatgg tatatccttg aaatatatat aaaaaaaaaa aaaaaaaaaa aaaaaaaaaa   14700
tgcagcttct caatgatatt cgaatacgct ttgaggagat acagcctaat atccgacaaa   14760
ctgttttaca gatttacgat cgtacttgtt acccatcatt gaattttgaa catccgaacc   14820
tgggagtttt ccctgaaaca gatagtatat ttgaacctgt ataataatat atagtctagc   14880
gctttacgga agacaatgta tgtatttcgg ttcctggaga aactattgca tctattgcat   14940
aggtaatctt gcacgtcgca tccccggttc attttctgcg tttccatctt gcacttcaat   15000
agcatatctt tgttaacgaa gcatctgtgc ttcattttgt agaacaaaaa tgcaacgcga   15060
gagcgctaat ttttcaaaca aagaatctga gctgcatttt tacagaacag aaatgcaacg   15120
cgaaagcgct atttaccaa cgaagaatct gtgcttcatt tttgtaaaac aaaaatgcaa   15180
cgcgagagcg ctaattttc aaacaaagaa tctgagctgc attttacag aacagaaatg   15240 caacgcgaga gcgctatttt accaacaaag aatctatact tcttttttgt tctacaaaaa   15300
tgcatcccga gagcgctatt tttctaacaa agcatcttag attactttt ttctcctttg    15360 tgcgctctat aatgcagtct cttgataact ttttgcactg taggtccgtt aaggttagaa   15420
gaaggctact ttggtgtcta ttttctcttc cataaaaaaa gcctgactcc acttcccgcg   15480
tttactgatt actagcgaag ctgcgggtgc attttttcaa gataaaggca tccccgatta   15540
tattctatac cgatgtggat tgcgcatact tgtgaacag aaagtgatag cgttgatgat    15600
tcttcattgg tcagaaaatt atgaacggtt tcttctattt tgtctctata tactacgtat   15660
aggaaatgtt tacattttcg tattgttttc gattcactct atgaatagtt cttactacaa   15720 ttttttgtc taaagagtaa tactagagat aaacataaaa aatgtagagg tcgagtttag   15780
atgcaagttc aaggagcgaa aggtggatgg gtaggttata tagggatata gcacagagat   15840
atatagcaaa gagatacttt tgagcaatgt ttgtggaagc ggtattcgca atattttagt   15900
agctcgttac agtccggtgc gttttggtt ttttgaaagt gcgtcttcag agcgcttttg    15960
```

-continued

```
gttttcaaaa gcgctctgaa gttcctatac tttctagaga ataggaactt cggaatagga      16020
acttcaaagc gtttccgaaa acgagcgctt ccgaaaatgc aacgcgagct gcgcacatac      16080
agctcactgt tcacgtcgca cctatatctg cgtgttgcct gtatatatat atacatgaga      16140
agaacggcat agtgcgtgtt tatgcttaaa tgcgtactta tatgcgtcta tttatgtagg      16200
atgaaaggta gtctagtacc tcctgtgata ttatcccatt ccatgcgggg tatcgtatgc      16260
ttccttcagc actacccttt agctgttcta tatgctgcca ctcctcaatt ggattagtct      16320
catccttcaa tgctatcatt tcctttgata ttggatcata tgcatagtac cgagaaacta      16380
gaggatc                                                               16387
```

<210> SEQ ID NO 31
<211> LENGTH: 448
<212> TYPE: DNA
<213> ORGANISM: Saccharomyces cerevisiae

<400> SEQUENCE: 31

```
cccattaccg acatttgggc gctatacgtg catatgttca tgtatgtatc tgtatttaaa       60
acacttttgt attattttc ctcatatatg tgtataggtt tatacggatg atttaattat      120
tacttcacca cccttattt caggctgata tcttagcctt gttactagtt agaaaaagac      180
atttttgctg tcagtcactg tcaagagatt cttttgctgg catttcttct agaagcaaaa      240
agagcgatgc gtcttttccg ctgaaccgtt ccagcaaaaa agactaccaa cgcaatatgg      300
attgtcagaa tcatataaaa gagaagcaaa taactccttg tcttgtatca attgcattat      360
aatatcttct tgttagtgca atatcatata gaagtcatcg aaatagatat taagaaaaac      420
aaactgtaca atcaatcaat caatcatc                                        448
```

<210> SEQ ID NO 32
<211> LENGTH: 1716
<212> TYPE: DNA
<213> ORGANISM: Bacillus subtilis

<400> SEQUENCE: 32

```
atgttgacaa aagcaacaaa agaacaaaaa tcccttgtga aaaacagagg ggcggagctt       60
gttgttgatt gcttagtgga gcaaggtgtc acacatgtat ttggcattcc aggtgcaaaa      120
attgatgcgg tatttgacgc tttacaagat aaaggacctg aaattatcgt tgcccggcac      180
gaacaaaacg cagcattcat ggcccaagca gtcggccgtt taactggaaa accgggagtc      240
gtgttagtca tcaggacc gggtgcctct aacttggcaa caggcctgct gacagcgaac      300
actgaaggag accctgtcgt tgcgcttgct ggaaacgtga tccgtgcaga tcgtttaaaa      360
cggacacatc aatctttgga taatgcggcg ctattccagc cgattacaaa atacagtgta      420
gaagttcaag atgtaaaaaa tataccggaa gctgttacaa atgcatttag gatagcgtca      480
gcagggcagg ctgggccgc ttttgtgagc tttccgcaag atgttgtgaa tgaagtcaca      540
aatacgaaaa acgtgcgtgc tgttcagcg ccaaaactcg gtcctgcagc agatgatgca      600
atcagtgcgg ccatagcaaa aatccaaaca gcaaaacttc ctgtcgtttt ggtcggcatg      660
aaaggcggaa gaccggaagc aattaaagcg gttcgcaagc ttttgaaaaa ggttcagctt      720
ccatttgttg aaacatatca agctgccggt accctttcta gagatttaga ggatcaatat      780
tttggccgta tcggttttgtt ccgcaaccag cctggcgatt tactgctaga gcaggcagat      840
gttgttctga cgatcggcta tgacccgatt gaatatgatc cgaaattctg gaatatcaat      900
ggagaccgga caattatcca tttagacgag attatcgctg acattgatca tgcttaccag      960
```

```
cctgatcttg aattgatcgg tgacattccg tccacgatca atcatatcga acacgatgct      1020
gtgaaagtgg aatttgcaga gcgtgagcag aaaatccttt ctgatttaaa acaatatatg      1080
catgaaggtg agcaggtgcc tgcagattgg aaatcagaca gagcgcaccc tcttgaaatc      1140
gttaaagagt tgcgtaatgc agtcgatgat catgttacag taacttgcga tatcggttcg      1200
cacgccattt ggatgtcacg ttatttccgc agctacgagc cgttaacatt aatgatcagt      1260
aacggtatgc aaacactcgg cgttgcgctt ccttgggcaa tcggcgcttc attggtgaaa      1320
ccgggagaaa aagtggtttc tgtctctggt gacggcggtt tcttattctc agcaatggaa      1380
ttagagacag cagttcgact aaaagcacca attgtacaca ttgtatggaa cgacagcaca      1440
tatgacatgg ttgcattcca gcaattgaaa aaatataacc gtacatctgc ggtcgatttc      1500
ggaaatatcg atatcgtgaa atatgcggaa agcttcggag caactggctt gcgcgtagaa      1560
tcaccagacc agctggcaga tgttctgcgt caaggcatga acgctgaagg tcctgtcatc      1620
atcgatgtcc cggttgacta cagtgataac attaatttag caagtgacaa gcttccgaaa      1680
gaattcgggg aactcatgaa aacgaaagct ctctag                               1716

<210> SEQ ID NO 33
<211> LENGTH: 571
<212> TYPE: PRT
<213> ORGANISM: Bacillus subtilis

<400> SEQUENCE: 33

Met Leu Thr Lys Ala Thr Lys Glu Gln Lys Ser Leu Val Lys Asn Arg
 1               5                  10                  15

Gly Ala Glu Leu Val Val Asp Cys Leu Val Glu Gln Gly Val Thr His
                20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
        50                  55                  60

Ala Phe Met Ala Gln Ala Val Gly Arg Leu Thr Gly Lys Pro Gly Val
 65                  70                  75                  80

Val Leu Val Thr Ser Gly Pro Gly Ala Ser Asn Leu Ala Thr Gly Leu
                 85                  90                  95

Leu Thr Ala Asn Thr Glu Gly Asp Pro Val Val Ala Leu Ala Gly Asn
                100                 105                 110

Val Ile Arg Ala Asp Arg Leu Lys Arg Thr His Gln Ser Leu Asp Asn
            115                 120                 125

Ala Ala Leu Phe Gln Pro Ile Thr Lys Tyr Ser Val Glu Val Gln Asp
        130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240
```

```
Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 34
<211> LENGTH: 250
<212> TYPE: DNA
<213> ORGANISM: Saccharymyces cerevisiae

<400> SEQUENCE: 34
ccgcaaatta aagccttcga gcgtcccaaa accttctcaa gcaaggtttt cagtataatg      60
ttacatgcgt acacgcgtct gtacagaaaa aaagaaaaa tttgaaatat aaataacgtt     120
cttaatacta acataactat aaaaaaataa atagggacct agacttcagg ttgtctaact    180
ccttcctttt cggttagagc ggatgtgggg ggagggcgtg aatgtaagcg tgacataact    240
```
aattacatga                                                            250

<210> SEQ ID NO 35
<211> LENGTH: 1181
<212> TYPE: DNA
<213> ORGANISM: Saccharomyces cerevisiae

<400> SEQUENCE: 35
taaaacctct agtggagtag tagatgtaat caatgaagcg gaagccaaaa gaccagagta      60
gaggcctata gaagaaactg cgatacccttt tgtgatggct aaacaaacag acatcttttt    120
atatgttttt acttctgtat atcgtgaagt agtaagtgat aagcgaattt ggctaagaac    180
gttgtaagtg aacaagggac ctcttttgcc tttcaaaaaa ggattaaatg gagttaatca    240
ttgagattta gttttcgtta gattctgtat ccctaaataa ctcccttacc cgacgggaag    300
gcacaaaaga cttgaataat agcaaacggc cagtagccaa gaccaaataa tactagagtt    360
aactgatggt cttaaacagg cattacgtgg tgaactccaa gaccaatata caaaatatcg    420
ataagttatt cttgcccacc aatttaagga gcctacatca ggacagtagt accattcctc    480
agagaagagg tatacataac aagaaaatcg cgtgaacacc ttatataact tagcccgtta    540
ttgagctaaa aaaccttgca aaatttccta tgaataagaa tacttcagac gtgataaaaa    600
tttactttct aactcttctc acgctgcccc tatctgttct tccgctctac cgtgagaaat    660
aaagcatcga gtacggcagt tcgctgtcac tgaactaaaa caataaggct agttcgaatg    720
atgaacttgc ttgctgtcaa acttctgagt tgccgctgat gtgacactgt gacaataaat    780
tcaaaccggt tatagcggtc tcctccggta ccggttctgc cacctccaat agagctcagt    840
aggagtcaga acctctgcgg tggctgtcag tgactcatcc gcgtttcgta agttgtgcgc    900
gtgcacattt cgcccgttcc cgctcatctt gcagcaggcg gaaattttca tcacgctgta    960
ggacgcaaaa aaaaaataat taatcgtaca agaatcttgg aaaaaaaatt gaaaatttt   1020 gtataaaagg gatgacctaa cttgactcaa tggcttttac acccagtatt ttcccttcc    1080 ttgtttgtta caattataga agcaagacaa aaacatatag acaacctatt cctaggagtt   1140
atattttttt accctaccag caatataagt aaaaaactag t                       1181

<210> SEQ ID NO 36
<211> LENGTH: 1014
<212> TYPE: DNA
<213> ORGANISM: artificial sequence
<220> FEATURE:
<223> OTHER INFORMATION: mutant of ilvC from Pseudomonas fluorescens

<400> SEQUENCE: 36
atgaaggtgt tttacgataa agactgcgat ctgagcatca tccagggaaa gaaggttgct     60
attataggat atggttccca aggacacgca caagccttga acttgaaaga ttctggggtc    120
gacgtgacag taggtctgta taaaggtgct gctgatgcag caaaggctga agcacatggc    180
tttaaagtca cagatgttgc agcggctgtt gctggcgctg atttagtcat gattttaatt    240
ccagatgaat tcaatcgca attgtacaaa aatgaaatag aaccaaacat taagaagggc    300
gctaccttgg ccttcagtca tggatttgcc attcattaca atcaagtagt ccccagggca    360
gatttggacg ttattatgat tgcacctaag gctccggggc atactgttag gagcgaattt    420
gttaagggtg gtggtattcc agatttgatc gctatatacc aagacgttag cggaaacgct    480
aagaatgtag ctttaagcta cgcagcagga gttggtggcg ggagaacggg tataatagaa    540

-continued

```
accactttta aagacgagac tgagacagat ttatttggag aacaagcggt tctgtgcgga    600
ggaactgttg aattggttaa agcaggcttt gagacgcttg tcgaagcagg gtacgctccc    660
gaaatggcat acttcgaatg tctacatgaa ttgaagttga tagtagactt aatgtatgaa    720
ggtggtatag ctaatatgaa ctattccatt tcaataatg cagaatatgg tgagtatgtc     780
accggacctg aagtcattaa cgcagaatca agacaagcca tgagaaatgc cttgaaacgt    840
atccaggacg gtaatacgc taagatgttc ataagtgaag gcgctacggg ttacccgagt     900
atgactgcta aaagaagaaa caatgcagca catggtatcg aaattattgg tgaacagtta    960
aggtctatga tgccctggat cggtgctaat aagatcgtag acaaggcgaa aaat         1014
```

<210> SEQ ID NO 37
<211> LENGTH: 338
<212> TYPE: PRT
<213> ORGANISM: Artificial sequence
<220> FEATURE:
<223> OTHER INFORMATION: synthetic construct mutant ilcV

<400> SEQUENCE: 37

```
Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Ala Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285
```

```
Met Phe Ile Ser Glu Gly Ala Thr Gly Tyr Pro Ser Met Thr Ala Lys
    290                 295                 300
Arg Arg Asn Asn Ala Ala His Gly Ile Glu Ile Gly Glu Gln Leu
305                 310                 315                 320
Arg Ser Met Met Pro Trp Ile Gly Ala Asn Lys Ile Val Asp Lys Ala
                325                 330                 335
Lys Asn

<210> SEQ ID NO 38
<211> LENGTH: 759
<212> TYPE: DNA
<213> ORGANISM: Saccharomyces cerevisiae

<400> SEQUENCE: 38
ggccctgcag gcctatcaag tgctggaaac ttttctctt ggaattttg caacatcaag       60 tcatagtcaa ttgaattgac ccaatttcac atttaagatt ttttttttt catccgacat     120 acatctgtac actaggaagc cctgttttc tgaagcagct tcaaatatat atattttta     180 catatttatt atgattcaat gaacaatcta attaaatcga aacaagaac cgaaacgcga     240 ataaataatt tatttagatg gtgacaagtg tataagtcct catcgggaca gctacgattt     300
ctctttcggt tttggctgag ctactggttg ctgtgacgca gcggcattag cgcggcgtta     360
tgagctaccc tcgtggcctg aaagatggcg ggaataaagc ggaactaaaa attactgact     420
gagccatatt gaggtcaatt tgtcaactcg tcaagtcacg tttggtggac ggcccctttc     480
caacgaatcg tatatactaa catgcgcgcg cttcctatat acacatatac atatatatat     540
atatatatat gtgtgcgtgt atgtgtacac ctgtatttaa tttccttact cgcgggtttt     600
tcttttttct caattcttgg cttcctcttt ctcgagtata taattttca ggtaaaattt     660 agtacgatag taaatactt ctcgaactcg tcacatatac gtgtacataa tgtctgaacc     720
agctcaaaag aaacaaaagg ttgctaacaa ctctctaga                           759

<210> SEQ ID NO 39
<211> LENGTH: 643
<212> TYPE: DNA
<213> ORGANISM: Saccharomyces cerevisiae

<400> SEQUENCE: 39
gaaatgaata acaatactga cagtactaaa taattgccta cttggcttca catacgttgc       60
atacgtcgat atagataata atgataatga cagcaggatt atcgtaatac gtaatagttg     120
aaaatctcaa aaatgtgtgg gtcattacgt aaataatgat aggaatggga ttcttctatt     180 tttcctttt ccattctagc agccgtcggg aaaacgtggc atcctctctt tcgggctcaa     240
ttggagtcac gctgccgtga gcatcctctc tttccatatc taacaactga gcacgtaacc     300
aatggaaaag catgagctta gcgttgctcc aaaaaagtat tggatggtta ataccatttg     360
tctgttctct tctgactttg actcctcaaa aaaaaaaat ctacaatcaa cagatcgctt     420
caattacgcc ctcacaaaaa cttttttcct tcttcttcgc ccacgttaaa ttttatccct     480
catgttgtct aacggatttc tgcacttgat ttattataaa aagacaaaga cataatactt     540
ctctatcaat ttcagttatt gttcttcctt gcgttattct tctgttcttc tttttctttt     600
gtcatatata accataacca agtaatacat attcaaatct aga                       643

<210> SEQ ID NO 40
<211> LENGTH: 1188
```

<212> TYPE: DNA
<213> ORGANISM: Saccharomyces cerevisiae

<400> SEQUENCE: 40

```
atgttgagaa ctcaagccgc cagattgatc tgcaactccc gtgtcatcac tgctaagaga      60
acctttgctt tggccacccg tgctgctgct tacagcagac cagctgcccg tttcgttaag     120
ccaatgatca ctacccgtgg tttgaagcaa atcaacttcg gtggtactgt tgaaaccgtc     180
tacgaaagag ctgactggcc aagagaaaag ttgttggact acttcaagaa cgacactttt     240
gctttgatcg gttacggttc ccaaggttac ggtcaaggtt tgaacttgag agacaacggt     300
ttgaacgtta tcattggtgt ccgtaaagat ggtgcttctt ggaaggctgc catcgaagac     360
ggttgggttc caggcaagaa cttgttcact gttgaagatg ctatcaagag aggtagttac     420
gttatgaact tgttgtccga tgccgctcaa tcagaaacct ggcctgctat caagccattg     480
ttgaccaagg gtaagacttt gtacttctcc cacggtttct ccccagtctt caaggacttg     540
actcacgttg aaccaccaaa ggacttagat gttatcttgg ttgctccaaa gggttccggt     600
agaactgtca gatctttgtt caaggaaggt cgtggtatta actcttctta cgccgtctgg     660
aacgatgtca ccggtaaggc tcacgaaaag gcccaagctt tggccgttgc cattggttcc     720
ggttacgttt accaaaccac tttcgaaaga gaagtcaact ctgacttgta cggtgaaaga     780
ggttgtttaa tgggtggtat ccacggtatg ttcttggctc aatacgacgt cttgagagaa     840
aacggtcact cccccatctga agctttcaac gaaaccgtcg aagaagctac ccaatctcta     900
tacccattga tcggtaagta cggtatggat tacatgtacg atgcttgttc caccaccgcc     960
agaagaggtg ctttggactg gtacccaatc ttcaagaatg ctttgaagcc tgttttccaa    1020
gacttgtacg aatctaccaa gaacggtacc gaaaccaaga gatctttgga attcaactct    1080
caacctgact acagagaaaa gctagaaaag gaattagaca ccatcagaaa catggaaatc    1140
tggaaggttg gtaaggaagt cagaaagttg agaccagaaa accaataa                 1188
```

<210> SEQ ID NO 41
<211> LENGTH: 395
<212> TYPE: PRT
<213> ORGANISM: Saccharomyces cerevisiae

<400> SEQUENCE: 41

```
Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140
```

```
Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
            165                 170                 175

Phe Lys Asp Leu Thr His Val Glu Pro Pro Lys Asp Leu Asp Val Ile
        180                 185                 190

Leu Val Ala Pro Lys Gly Ser Gly Arg Thr Val Arg Ser Leu Phe Lys
    195                 200                 205

Glu Gly Arg Gly Ile Asn Ser Ser Tyr Ala Val Trp Asn Asp Val Thr
210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
            245                 250                 255

Tyr Gly Glu Arg Gly Cys Leu Met Gly Gly Ile His Gly Met Phe Leu
        260                 265                 270

Ala Gln Tyr Asp Val Leu Arg Glu Asn Gly His Ser Pro Ser Glu Ala
    275                 280                 285

Phe Asn Glu Thr Val Glu Glu Ala Thr Gln Ser Leu Tyr Pro Leu Ile
290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
            325                 330                 335

Pro Val Phe Gln Asp Leu Tyr Glu Ser Thr Lys Asn Gly Thr Glu Thr
        340                 345                 350

Lys Arg Ser Leu Glu Phe Asn Ser Gln Pro Asp Tyr Arg Glu Lys Leu
    355                 360                 365

Glu Lys Glu Leu Asp Thr Ile Arg Asn Met Glu Ile Trp Lys Val Gly
370                 375                 380

Lys Glu Val Arg Lys Leu Arg Pro Glu Asn Gln
385                 390                 395

<210> SEQ ID NO 42
<211> LENGTH: 15539
<212> TYPE: DNA
<213> ORGANISM: artificial sequence
<220> FEATURE:
<223> OTHER INFORMATION: constructed plasmid

<400> SEQUENCE: 42
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta     300
ttactcttgg cctcctctag tacactctat attttttat gcctcggtaa tgattttcat     360
tttttttttt ccacctagcg gatgactctt ttttttctt agcgattggc attatcacat     420
aatgaattat acattatata agtaatgtg atttcttcga agaatatact aaaaaatgag     480
caggcaagat aaacgaaggc aaagatgaca gagcagaaag ccctagtaaa gcgtattaca     540
aatgaaacca agattcagat tgcgatctct ttaaagggtg gtcccctagc gatagagcac     600
```

```
tcgatcttcc cagaaaaaga ggcagaagca gtagcagaac aggccacaca atcgcaagtg    660
attaacgtcc acacaggtat agggtttctg gaccatatga tacatgctct ggccaagcat    720
tccggctggt cgctaatcgt tgagtgcatt ggtgacttac acatagacga ccatcacacc    780
actgaagact gcgggattgc tctcggtcaa gcttttaaag aggccctagg ggccgtgcgt    840
ggagtaaaaa ggtttggatc aggatttgcg cctttggatg aggcactttc cagagcggtg    900
gtagatcttt cgaacaggcc gtacgcagtt gtcgaacttg gtttgcaaag ggagaaagta    960
ggagatctct cttgcgagat gatcccgcat tttcttgaaa gctttgcaga ggctagcaga   1020
attaccctcc acgttgattg tctgcgaggc aagaatgatc atcaccgtag tgagagtgcg   1080
ttcaaggctc ttgcggttgc cataagagaa gccacctcgc ccaatggtac caacgatgtt   1140
ccctccacca aggtgttct tatgtagtga caccgattat ttaaagctgc agcatacgat   1200
atatatacat gtgtatatat gtataccat gaatgtcagt aagtatgtat acgaacagta   1260
tgatactgaa gatgacaagg taatgcatca ttctatacgt gtcattctga acgaggcgcg   1320 cttcctttt ttcttttgc ttttctttt ttttctctt gaactcgacg gatctatgcg   1380
gtgtgaaata ccgcacagat gcgtaaggag aaaataccgc atcaggaaat tgtaagcgtt   1440
aatattttgt taaaattcgc gttaaatttt tgttaaatca gctcattttt taaccaatag   1500
gccgaaatcg gcaaaatccc ttataaatca aagaataga ccgagatagg gttgagtgtt   1560
gttccagttt ggaacaagag tccactatta agaacgtgg actccaacgt caagggcga   1620 aaaccgtct atcagggcga tggcccacta cgtgaaccat caccctaatc aagttttttg   1680
gggtcgaggt gccgtaaagc actaaatcgg aaccctaaag ggagccccg atttagagct   1740 tgacggggaa agccggcgaa cgtggcgaga aggaaggga agaaagcgaa aggagcgggc   1800
gctagggcgc tggcaagtgt agcggtcacg ctgcgcgtaa ccaccacacc cgccgcgctt   1860
aatgcgccgc tacagggcgc gtccattcgc cattcaggct gcgcaactgt tgggaagggc   1920
gcggtgcggg cctcttcgct attacgccag ctggcgaaag ggggatgtgc tgcaaggcga   1980
ttaagttggg taacgccagg gttttcccag tcacgacgtt gtaaaacgac ggccagtgag   2040
cgcgcgtaat acgactcact ataggggcgaa ttgggtaccg gccccccct cgaggtcgac   2100 ggcgcgccac tggtagagag cgactttgta tgccccaatt gcgaaacccg cgatatcctt   2160
ctcgattctt tagtacccga ccaggacaag gaaaaggagg tcgaaacgtt tttgaagaaa   2220
caagaggaac tacacggaag ctctaaagat ggcaaccagc cagaaactaa gaaaatgaag   2280
ttgatggatc caactggcac cgctggcttg aacaacaata ccagccttcc aacttctgta   2340
aataacggcg gtacgccagt gccaccagta ccgttacctt tcggtatacc tccttttccc   2400
atgtttccaa tgcccttcat gcctccaacg gctactatca caaatcctca tcaagctgac   2460
gcaagcccta agaaatgaat aacaatactg acagtactaa ataattgcct acttggcttc   2520
acatacgttg catacgtcga tatagataat aatgataatg acagcaggat tatcgtaata   2580
cgtaatagct gaaaatctca aaaatgtgtg ggtcattacg taaataatga taggaatggg   2640
attcttctat ttttccttt tccattctag cagccgtcgg gaaaacgtgg catcctctct   2700
ttcgggctca attggagtca cgctgccgtg agcatcctct ctttccatat ctaacaactg   2760
agcacgtaac caatggaaaa gcatgagctt agcgttgctc caaaaaagta ttggatggtt   2820
aataccattt gtctgttctc ttctgacttt gactcctcaa aaaaaaaaat ctacaatcaa   2880
cagatcgctt caattacgcc ctcacaaaaa cttttttcct tcttcttcgc ccacgttaaa   2940
ttttatccct catgttgtct aacggatttc tgcacttgat ttattataaa aagacaaaga   3000
```

```
cataatactt ctctatcaat ttcagttatt gttcttcctt gcgttattct tctgttcttc   3060 ttttctttt gtcatatata accataacca agtaatacat attcaaacta gtatgactga    3120
caaaaaaact cttaaagact taagaaatcg tagttctgtt tacgattcaa tggttaaatc   3180
acctaatcgt gctatgttgc gtgcaactgg tatgcaagat gaagactttg aaaaacctat   3240
cgtcggtgtc atttcaactt gggctgaaaa cacaccttgt aatatccact tacatgactt   3300 tggtaaaacta gccaaagtcg gtgttaagga agctggtgct tggccagttc agttcggaac  3360
aatcacggtt tctgatggaa tcgccatggg aacccaagga atgcgtttct ccttgacatc   3420
tcgtgatatt attgcagatt ctattgaagc agccatggga ggtcataatg cggatgcttt   3480
tgtagccatt ggcggttgtg ataaaaacat gcccggttct gttatcgcta tggctaacat   3540
ggatatccca gccattttg cttacggcgg aacaattgca cctggtaatt tagacggcaa    3600
agatatcgat ttagtctctg tctttgaagg tgtcggccat tggaaccacg gcgatatgac   3660
caaagaagaa gttaaagctt tggaatgtaa tgcttgtccc ggtcctggag ctgcggtgg    3720 tatgtatact gctaacacaa tggcgacagc tattgaagtt ttgggactta gccttccggg   3780
ttcatcttct cacccggctg aatccgcaga aagaaagca gatattgaag aagctggtcg    3840
cgctgttgtc aaaatgctcg aaatgggctt aaaaccttct gacattttaa cgcgtgaagc   3900
ttttgaagat gctattactg taactatggc tctgggaggt tcaaccaact caaccttca    3960 cctcttagct attgcccatg ctgctaatgt ggaattgaca cttgatgatt tcaatacttt   4020
ccaagaaaaa gttcctcatt tggctgattt gaaaccttct ggtcaatatg tattccaaga   4080
cctttacaag gtcggagggg taccagcagt tatgaaatat ctccttaaaa atggcttcct   4140
tcatggtgac cgtatcactt gtactggcaa aacagtcgct gaaaatttga aggcttttga   4200
tgatttaaca cctggtcaaa aggttattat gccgcttgaa aatcctaaac gtgaagatgg   4260
tccgctcatt attctccatg gtaacttggc tccagacggt gccgttgcca agtttctgg    4320 tgtaaaagtg cgtcgtcatg tcggtcctgc taaggtcttt aattctgaag aagaagccat   4380
tgaagctgtc ttgaatgatg atattgttga tggtgatgtt gttgtcgtac gttttgtagg   4440
accaaagggc ggtcctggta tgcctgaaat gctttcccctt tcatcaatga ttgttggtaa  4500
agggcaaggt gaaaaagttg cccttctgac agatggccgc ttctcaggtg gtacttatgg   4560
tcttgtcgtg ggtcatatcg ctcctgaagc acaagatggc ggtccaatcg cctacctgca   4620
aacaggagac atagtcacta ttgaccaaga cactaaggaa ttacactttg atatctccga   4680
tgaagagtta aaacatcgtc aagagaccat tgaattgcca ccgctctatt cacgcggtat   4740
ccttggtaaa tatgctcaca tcgtttcgtc tgcttctagg ggagccgtaa cagactttg   4800 gaagcctgaa gaaactggca aaaaatgttg tcctggttgc tgtggttaag cggccgcgtt   4860
aattcaaatt aattgatata gttttttaat gagtattgaa tctgtttaga aataatggaa   4920 tattatttt atttatttat ttatattatt ggtcggctct tttcttctga aggtcaatga   4980
caaaatgata tgaaggaaat aatgatttct aaaattttac aacgtaagat attttacaa   5040 aagcctagct catcttttgt catgcactat tttactcacg cttgaaatta acggccagtc   5100
cactgcggag tcatttcaaa gtcatcctaa tcgatctatc gttttgata gctcattttg    5160 gagttcgcga ttgtcttctg ttattcacaa ctgtttaat ttttatttca ttctggaact    5220
cttcgagttc tttgtaaagt ctttcatagt agcttacttt atcctccaac atatttaact   5280
tcatgtcaat ttcggctctt aaattttcca catcatcaag ttcaacatca tcttttaact   5340
```

```
tgaatttatt ctctagctct tccaaccaag cctcattgct ccttgattta ctggtgaaaa    5400
gtgatacact ttgcgcgcaa tccaggtcaa aactttcctg caaagaattc accaatttct    5460
cgacatcata gtacaatttg ttttgttctc ccatcacaat ttaatatacc tgatggattc    5520
ttatgaagcg ctgggtaatg acgtgtcac tctacttcgc cttttccct actccttta      5580 gtacggaaga caatgctaat aaataagagg gtaataataa tattattaat cggcaaaaaa    5640
gattaaacgc caagcgttta attatcagaa agcaaacgtc gtaccaatcc ttgaatgctt    5700
cccaattgta tattaagagt catcacagca acatattctt gttattaaat taattattat    5760 tgattttga tattgtataa aaaaaccaaa tatgtataaa aaaagtgaat aaaaaatacc     5820
aagtatggag aaatatatta gaagtctata cgttaaacca cccgggcccc ccctcgaggt    5880
cgacggtatc gataagcttg atatcgaatt cctgcagccc ggggatcca ctagttctag     5940 agcggccgct ctagaactag taccacaggt gttgtcctct gaggacataa aatacacacc    6000
gagattcatc aactcattgc tggagttagc atatctacaa ttgggtgaaa tggggagcga    6060
tttgcaggca tttgctcggc atgccggtag aggtgtggtc aataagagcg acctcatgct    6120
atacctgaga aagcaacctg acctacagga aagagttact caagaataag aattttcgtt    6180
ttaaaaccta agagtcactt taaaatttgt atacacttat ttttttata acttatttaa     6240 taataaaaat cataaatcat aagaaattcg cttactctta attaatcaaa aagttaaaat    6300
tgtacgaata gattcaccac ttcttaacaa atcaaaccct tcattgattt tctcgaatgg    6360
caatacatgt gtaattaaag gatcaagagc aaacttcttc gccataaagt cggcaacaag    6420
ttttggaaca ctatccttgc tcttaaaacc gccaaatata gctcccttcc atgtacgacc    6480
gcttagcaac agcataggat tcatcgacaa attttgtgaa tcaggaggaa cacctacgat    6540
cacactgact ccatatgcct cttgacagca ggacaacgca gttaccatag tatcaagacg    6600
gcctataact tcaaaagaga aatcaactcc accgtttgac atttcagtaa ggacttcttg    6660
tattggtttc ttataatctt gagggttaac acattcagta gccccgacct ccttagcttt    6720
tgcaaatttg tccttattga tgtctacacc tataatcctc gctgcgcctg cagctttaca    6780
ccccataata acgcttagtc ctactcctcc taaaccgaat actgcacaag tcgaaccctg    6840
tgtaaccttt gcaactttaa ctgcggaacc gtaaccggtg gaaaatccgc accctatcaa    6900
gcaaactttt tccagtggtg aagctgcatc gattttagcg acagatatct cgtccaccac    6960
tgtgtattgg gaaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140
gatcacttta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc     7380
tttacactta ataactttac cggctgttga catcctcagc tagctattgt aatatgtgtg    7440
tttgtttgga ttattaagaa gaataattac aaaaaaaatt acaaggaag gtaattacaa     7500 cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc tttttattct tcatcgttcc actaacccttt ttccatcagc    7740
```

| | |
|---|---|
| tggcagggaa cggaaagtgg aatcccattt agcgagcttc ctcttttctt caagaaaaga | 7800 |
| cgaagcttgt gtgtgggtgc gcgcgctagt atctttccac attaagaaat ataccataaa | 7860 |
| ggttacttag acatcactat ggctatatat atatatatat atatatgtaa cttagcacca | 7920 |
| tcgcgcgtgc atcactgcat gtgttaaccg aaaagtttgg cgaacacttc accgacacgg | 7980 |
| tcatttagat ctgtcgtctg cattgcacgt cccttagcct taaatcctag gcgggagcat | 8040 |
| tctcgtgtaa ttgtgcagcc tgcgtagcaa ctcaacatag cgtagtctac ccagtttttc | 8100 |
| aagggtttat cgttagaaga ttctcccttt tcttcctgct cacaaatctt aaagtcatac | 8160 |
| attgcacgac taaatgcaag catgcggatc ccccgggctg caggaattcg atatcaagct | 8220 |
| tatcgatacc gtcgactggc cattaatctt cccatatta gatttcgcca agccatgaaa | 8280 |
| gttcaagaaa ggtctttaga cgaattaccc ttcatttctc aaactggcgt caagggatcc | 8340 |
| tggtatggtt ttatcgtttt atttctggtt cttatagcat cgttttggac ttctctgttc | 8400 |
| ccattaggcg gttcaggagc cagcgcagaa tcattctttg aaggatactt atcctttcca | 8460 |
| attttgattg tctgttacgt tggacataaa ctgtatacta gaaattggac tttgatggtg | 8520 |
| aaactagaag atatggatct tgataccggc agaaaacaag tagatttgac tcttcgtagg | 8580 |
| gaagaaatga ggattgagcg agaaacatta gcaaaagat ccttcgtaac aagatttta | 8640 |
| catttctggt gttgaaggga agatatgag ctatacagcg gaattccat atcactcaga | 8700 |
| ttttgttatc taatttttc cttcccacgt ccgcgggaat ctgtgtatat tactgcatct | 8760 |
| agatatatgt tatcttatct tggcgcgtac atttaatttt caacgtattc tataagaaat | 8820 |
| tgcgggagtt tttttcatgt agatgatact gactgcacgc aaatataggc atgatttata | 8880 |
| ggcatgattt gatggctgta ccgataggaa cgctaagagt aacttcagaa tcgttatcct | 8940 |
| ggcggaaaaa attcatttgt aaactttaaa aaaaaagcc aatatcccca aaattattaa | 9000 |
| gagcgcctcc attattaact aaaatttcac tcagcatcca caatgtatca ggtatctact | 9060 |
| acagatatta catgtggcga aaaagacaag aacaatgcaa tagcgcatca agaaaaaaca | 9120 |
| caaagctttc aatcaatgaa tcgaaaatgt cattaaaata gtatataaat tgaaactaag | 9180 |
| tcataaagct ataaaaagaa aatttattta aatgcaagat ttaaagtaaa ttcacggccc | 9240 |
| tgcaggcctc agctcttgtt ttgttctgca aataacttac ccatcttttt caaaacttta | 9300 |
| ggtgcaccct cctttgctag aataagttct atccaataca tcctatttgg atctgcttga | 9360 |
| gcttctttca tcacggatac gaattcattt tctgttctca caattttgga cacaactctg | 9420 |
| tcttccgttg ccccgaaact ttctggcagt tttgagtaat tccacatagg aatgtcatta | 9480 |
| taactctggt tcggaccatg aatttccctc tcaaccgtgt aaccatcgtt attaatgata | 9540 |
| aagcagattg ggtttatctt ctctctaatg gctagtccta attcttggac agtcagttgc | 9600 |
| aatgatccat ctccgataaa caataaatgt ctagattctt tatctgcaat ttggctgcct | 9660 |
| agagctgcgg ggaaagtgta tcctatagat ccccacaagg gttgaccaat aaaatgtgat | 9720 |
| ttcgatttca gaaatataga tgaggcaccg aagaagaag tgccttgttc agccacgatc | 9780 |
| gtctcattac tttgggtcaa attttcgaca gcttgccaca gtctatcttg tgacaacagc | 9840 |
| gcgttagaag gtacaaaatc ttcttgcttt ttatctatgt acttgccttt atattcaatt | 9900 |
| tcggacaagt caagaagaga tgatatcagg gattcgaagt cgaaattttg gattctttcg | 9960 |
| ttgaaaattt taccttcatc gatattcaag gaaatcattt tattttcatt aagatggtga | 10020 |
| gtaaatgcac ccgtactaga atcggtaagc tttacaccca acataagaat aaaatcagca | 10080 |

```
gattccacaa attccttcaa gtttggctct gacagagtac cgttgtaaat ccccaaaaat   10140
gagggcaatg cttcatcaac agatgattta ccaaagttca aagtagtaat aggtaactta   10200
gtctttgaaa taaactgagt aacagtcttc tctaggccga acgatataat ttcatggcct   10260
gtgattacaa ttggtttctt ggcattcttc agactttcct gtattttgtt cagaatctct   10320
tgatcagatg tattcgacgt ggaattttcc ttcttaagag gcaaggatgg ttttttcagcc  10380 ttagcggcag ctacatctac aggtaaattg atgtaaaccg gctttctttc ctttagtaag   10440
gcagacaaca ctctatcaat ttcaacagtt gcattctcgg ctgtcaataa agtcctggca   10500
gcagtaaccg gttcgtgcat cttcataaag tgcttgaaat caccatcagc caacgtatgg   10560
tgaacaaact taccttcgtt ctgcactttc gaggtaggag atcccacgat ctcaacaaca   10620
ggcaggttct cagcatagga gcccgctaag ccattaactg cggataattc gccaacacca   10680
aatgtagtca agaatgccgc agccttttc gttcttgcgt acccgtcggc catataggag   10740
gcatttaact cattagcatt tcccacccat ttcatatctt tgtgtgaaat aatttgatct   10800
agaaattgca aattgtagtc acctggtact ccgaatattt cttctatacc taattcgtgt   10860
aatctgtcca acagatagtc acctactgta tacattttgt ttactagttt atgtgtgttt   10920
attcgaaact aagttcttgg tgttttaaaa ctaaaaaaaa gactaactat aaaagtagaa   10980
tttaagaagt ttaagaaata gatttacaga attacaatca ataccaccg tctttatata    11040 cttattagtc aagtagggga ataatttcag ggaactggtt tcaacctttt ttttcagctt   11100
tttccaaatc agagagagca gaaggtaata gaaggtgtaa gaaaatgaga tagatacatg   11160
cgtgggtcaa ttgccttgtg tcatcattta ctccaggcag gttgcatcac tccattgagg   11220
ttgtgcccgt tttttgcctg tttgtgcccc tgttctctgt agttgcgcta agagaatgga   11280
cctatgaact gatggttggt gaagaaaaca atattttggt gctgggattc ttttttttc    11340 tggatgccag cttaaaaagc gggctccatt atatttagtg gatgccagga ataaactgtt   11400
cacccagaca cctacgatgt tatatattct gtgtaacccg cccctatt tgggcatgta    11460 cgggttacag cagaattaaa aggctaattt tttgactaaa taaagttagg aaaatcacta   11520
ctattaatta tttacgtatt ctttgaaatg gcagtattga taatgataaa ctcgaactga   11580
aaaagcgtgt ttttattca aaatgattct aactccctta cgtaatcaag gaatcttttt    11640
gccttggcct ccgcgtcatt aaacttcttg ttgttgacgc taacattcaa cgctagtata   11700
tattcgtttt tttcaggtaa gttcttttca acgggtctta ctgatgaggc agtcgcgtct   11760
gaacctgtta agaggtcaaa tatgtcttct tgaccgtacg tgtcttgcat gttattagct   11820
ttgggaattt gcatcaagtc ataggaaaat ttaaatcttg gctctcttgg gctcaaggtg   11880
acaaggtcct cgaaaatagg gcgcgcccca ccgcggtgga gctccagctt tgttcccctt   11940
tagtgagggt taattgcgcg cttggcgtaa tcatggtcat agctgtttcc tgtgtgaaat   12000
tgttatccgc tcacaattcc acacaacata cgagccggaa gcataaagtg taaagcctgg   12060
ggtgcctaat gagtgagcta actcacatta attgcgttgc gctcactgcc cgctttccag   12120
tcgggaaacc tgtcgtgcca gctgcattaa tgaatcggcc aacgcgcggg gagaggcggt   12180
ttgcgtattg ggcgctcttc cgcttcctcg ctcactgact cgctgcgctc ggtcgttcgg   12240
ctgcggcgag cggtatcagc tcactcaaag gcggtaatac ggttatccac agaatcaggg   12300
gataacgcag gaaagaacat gtgagcaaaa ggccagcaaa aggccaggaa ccgtaaaaag   12360
gccgcgttgc tggcgttttt ccataggctc cgccccctg acgagcatca caaaaatcga   12420
cgctcaagtc agaggtggcg aaacccgaca ggactataaa gataccaggc gtttccccct   12480
```

```
ggaagctccc tcgtgcgctc tcctgttccg accctgccgc ttaccggata cctgtccgcc   12540 tttctcccctt cgggaagcgt ggcgcttcct catagctcac gctgtaggta tctcagttcg   12600
gtgtaggtcg ttcgctccaa gctgggctgt gtgcacgaac cccccgttca gcccgaccgc   12660
tgcgccttat ccgtaacta tcgtcttgag tccaacccgg taagacacga cttatcgcca   12720
ctggcagcag ccactggtaa caggattagc agagcgaggt atgtaggcgg tgctacagag   12780
ttcttgaagt ggtggcctaa ctacggctac actagaagaa cagtatttgg tatctgcgct   12840
ctgctgaagc cagttacctt cggaaaaaga gttggtagct cttgatccgg caaacaaacc   12900
accgctggta gcggtggttt ttttgtttgc aagcagcaga ttacgcgcag aaaaaaagga   12960
tctcaagaag atcctttgat cttttctacg gggtctgacg ctcagtggaa cgaaaactca   13020
cgttaaggga ttttggtcat gagattatca aaaaggatct tcacctagat ccttttaaat   13080
taaaaatgaa gttttaaatc aatctaaagt atatatgagt aaacttggtc tgacagttac   13140
caatgcttaa tcagtgaggc acctatctca gcgatctgtc tatttcgttc atccatagtt   13200
gcctgactcc ccgtcgtgta gataactacg atacgggagg gcttaccatc tggccccagt   13260
gctgcaatga taccgcgaga cccacgctca ccggctccag atttatcagc aataaaccag   13320
ccagccggaa gggccgagcg cagaagtggt cctgcaactt tatccgcctc catccagtct   13380
attaattgtt gccgggaagc tagagtaagt agttcgccag ttaatagttt gcgcaacgtt   13440
gttgccattg ctacaggcat cgtggtgtca cgctcgtcgt ttggtatggc ttcattcagc   13500
tccggttccc aacgatcaag gcgagttaca tgatccccca tgttgtgcaa aaaagcggtt   13560
agctccttcg gtcctccgat cgttgtcaga agtaagttgg ccgcagtgtt atcactcatg   13620
gttatggcag cactgcataa ttctcttact gtcatgccat ccgtaagatg cttttctgtg   13680
actggtgagt actcaaccaa gtcattctga gaatagtgta tgcggcgacc gagttgctct   13740
tgcccggcgt caatacggga taataccgcg ccacatagca gaactttaaa agtgctcatc   13800
attggaaaac gttcttcggg gcgaaaactc tcaaggatct taccgctgtt gagatccagt   13860
tcgatgtaac ccactcgtgc acccaactga tcttcagcat cttttacttt caccagcgtt   13920
tctgggtgag caaaaacagg aaggcaaaat gccgcaaaaa agggaataag ggcgacacgg   13980
aaatgttgaa tactcatact cttcctttt caatattatt gaagcattta tcagggttat   14040
tgtctcatga gcggatacat atttgaatgt atttagaaaa ataaacaaat aggggttccg   14100
cgcacatttc cccgaaaagt gccacctgaa cgaagcatct gtgcttcatt ttgtagaaca   14160
aaaatgcaac gcgagagcgc taattttca acaaagaat ctgagctgca tttttacaga   14220
acagaaatgc aacgcgaaag cgctatttta ccaacgaaga atctgtgctt cattttgta   14280 aaacaaaaat gcaacgcgag agcgctaatt tttcaaacaa agaatctgag ctgcattttt   14340
acagaacaga atgcaacgc gagagcgcta ttttaccaac aaagaatcta tacttctttt   14400
ttgttctaca aaaatgcatc ccgagagcgc tattttttcta acaaagcatc ttagattact   14460 tttttttctcc tttgtgcgct ctataatgca gtctcttgat aacttttgc actgtaggtc   14520 cgttaaggtt agaagaaggc tactttggtg tctattttct cttccataaa aaagcctga   14580 ctccacttcc cgcgtttact gattactagc gaagctgcgg gtgcatttt tcaagataaa   14640 ggcatcccg attatattct ataccgatgt ggattgcgca tactttgtga acagaaagtg   14700
atagcgttga tgattcttca ttggtcagaa aattatgaac ggtttcttct attttgtctc   14760
tatatactac gtataggaaa tgtttacatt ttcgtattgt tttcgattca ctctatgaat   14820
```

```
agttcttact acaatttttt tgtctaaaga gtaatactag agataaacat aaaaaatgta    14880
gaggtcgagt ttagatgcaa gttcaaggag cgaaaggtgg atgggtaggt tatataggga    14940
tatagcacag agatatatag caaagagata cttttgagca atgtttgtgg aagcggtatt    15000
cgcaatattt tagtagctcg ttacagtccg gtgcgttttt ggttttttga aagtgcgtct    15060
tcagagcgct tttggttttc aaaagcgctc tgaagttcct atactttcta gagaatagga    15120
acttcggaat aggaacttca aagcgtttcc gaaaacgagc gcttccgaaa atgcaacgcg    15180
agctgcgcac atacagctca ctgttcacgt cgcacctata tctgcgtgtt gcctgtatat    15240
atatatacat gagaagaacg gcatagtgcg tgtttatgct taaatgcgta cttatatgcg    15300
tctatttatg taggatgaaa ggtagtctag tacctcctgt gatattatcc cattccatgc    15360
ggggtatcgt atgcttcctt cagcactacc ctttagctgt tctatatgct gccactcctc    15420
aattggatta gtctcatcct tcaatgctat catttccttt gatattggat catactaaga    15480
aaccattatt atcatgacat taacctataa aaataggcgt atcacgaggc cctttcgtc    15539
```

<210> SEQ ID NO 43
<211> LENGTH: 1644
<212> TYPE: DNA
<213> ORGANISM: artificial sequence
<220> FEATURE:
<223> OTHER INFORMATION: B subtilis kivD cocon optimized for S
      cerevisiae expression

<400> SEQUENCE: 43

```
atgtatacag taggtgacta tctgttggac agattcacg aattaggtat agaagaaata      60
ttcggagtac caggtgacta caatttgcaa tttctagatc aaattatttc acacaaagat     120
atgaaatggg tgggaaatgc taatgagtta atgcctcct atatggccga cgggtacgca     180
agaacgaaaa aggctgcggc attcttgact acatttggtg ttggcgaatt atccgcagtt     240
aatggcttag cgggctccta tgctgagaac ctgcctgttg ttgagatcgt gggatctcct     300
acctcgaaag tgcagaacga aggtaagttt gttcaccata cgttggctga tggtgatttc     360
aagcacttta tgaagatgca cgaaccggtt actgctgcca ggactttatt gacagccgag     420
aatgcaactg ttgaaattga tagtgtgttg tctgccttac taaaggaaag aaagccggtt     480
tacatcaatt tacctgtaga tgtagctgcc gctaaggctg aaaaaccatc cttgcctctt     540
aagaaggaaa ttccacgtc gaatacatct gatcaagaga ttctgaacaa atacaggaa     600 agtctgaaga atgccaagaa accaattgta atcacaggcc atgaaattat atcgttcggc     660
ctagagaaga ctgttactca gtttatttca aagactaagt tacctattac tactttgaac     720
tttggtaaat catctgttga tgaagcattg ccctcatttt tggggattta caacggtact     780
ctgtcagagc caaacttgaa ggaatttgtg aatctgctg atttattct tatgttgggt     840 gtaaagctta ccgattctag tacgggtgca tttactcacc atcttaatga aaataaaatg     900
atttccttga atatcgatga aggtaaaatt ttcaacgaaa gaatccaaaa tttcgacttc     960
gaatccctga tatcatctct tcttgacttg tccgaaattg aatataaagg caagtacata    1020
gataaaaagc aagaagattt tgtaccttct aacgcgctgt tgtcacaaga tagactgtgg    1080
caagctgtcg aaaatttgac ccaaagtaat gagacgatcg tggctgaaca aggcacttct    1140
ttcttcggtg cctcatctat atttctgaaa tcgaaatcac attttattgg tcaacccttg    1200
tggggatcta taggatacac tttccccgca gctctaggca gccaaattgc agataaagaa    1260
tctagacatt tattgtttat cggagatgga tcattgcaac tgactgtcca agaattagga    1320
```

```
ctagccatta gagagaagat aaacccaatc tgctttatca ttaataacga tggttacacg    1380
gttgagaggg aaattcatgg tccgaaccag agttataatg acattcctat gtggaattac    1440
tcaaaactgc cagaaagttt cggggcaacg gaagacagag ttgtgtccaa aattgtgaga    1500
acagaaaatg aattcgtatc cgtgatgaaa gaagctcaag cagatccaaa taggatgtat    1560
tggatagaac ttattctagc aaaggagggt gcacctaaag ttttgaaaaa gatgggtaag    1620
ttatttgcag aacaaaacaa gagc                                           1644
```

<210> SEQ ID NO 44
<211> LENGTH: 548
<212> TYPE: PRT
<213> ORGANISM: Bacillus subtilis

<400> SEQUENCE: 44

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320
```

```
Glu Ser Leu Ile Ser Ser Leu Asp Leu Ser Ile Glu Tyr Lys
            325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
            370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
            485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
            530                 535                 540

Gln Asn Lys Ser
545

<210> SEQ ID NO 45
<211> LENGTH: 1125
<212> TYPE: DNA
<213> ORGANISM: artificial sequence
<220> FEATURE:
<223> OTHER INFORMATION: horse ADH coding region codon optimized for S.
      cerevisiae expression

<400> SEQUENCE: 45
atgtcaacag ccggtaaagt tattaagtgt aaagcggcag ttttgtggga agagaaaaag      60
ccgtttagca tagaagaagt agaagtagcg ccaccaaaag cacacgaggt tagaatcaag     120
atggttgcca ccggaatctg tagatccgac gaccatgtgg tgagtggcac tctagttact     180
cctttgccag taatcgcggg acacgaggct gccggaatcg ttgaatccat aggtgaaggt     240
gttaccactg ttcgtcctgg tgataaagtg atcccactgt tcactcctca atgtggtaag     300
tgtagagtct gcaaacatcc tgagggtaat ttctgcctta aaaatgattt gtctatgcct     360
agaggtacta tgcaggatgg tacaagcaga tttacatgca gagggaaacc tatacaccat     420
ttccttggta cttctacatt ttcccaatac acagtggtgg acgagatatc tgtcgctaaa     480
atcgatgcag cttcaccact ggaaaaagtt tgcttgatag ggtgcggatt tccaccggt     540 tacggttccg cagttaaagt tgcaaaggtt acacagggtt cgacttgtgc agtattcggt     600
ttaggaggag taggactaag cgttattatg gggtgtaaag ctgcaggcgc agcgaggatt     660
```

```
ataggtgtag acatcaataa ggacaaattt gcaaaagcta aggaggtcgg ggctactgaa      720
tgtgttaacc ctcaagatta taagaaacca atacaagaag tccttactga aatgtcaaac      780
ggtggagttg atttctcttt tgaagttata ggccgtcttg atactatggt aactgcgttg      840
tcctgctgtc aagaggcata tggagtcagt gtgatcgtag gtgttcctcc tgattcacaa      900
aatttgtcga tgaatcctat gctgttgcta agcggtcgta catggaaggg agctatattt      960
ggcggtttta agagcaagga tagtgttcca aaacttgttg ccgactttat ggcgaagaag     1020
tttgctcttg atccttaat tacacatgta ttgccattcg agaaaatcaa tgaagggttt     1080
gatttgttaa gaagtggtga atctattcgt acaattttaa ctttt                    1125

<210> SEQ ID NO 46
<211> LENGTH: 375
<212> TYPE: PRT
<213> ORGANISM: Equus caballus

<400> SEQUENCE: 46

Met Ser Thr Ala Gly Lys Val Ile Lys Cys Lys Ala Ala Val Leu Trp
1               5                   10                  15

Glu Glu Lys Lys Pro Phe Ser Ile Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285
```

```
Val Ser Val Ile Val Gly Val Pro Pro Asp Ser Gln Asn Leu Ser Met
    290                 295                 300
Asn Pro Met Leu Leu Leu Ser Gly Arg Thr Trp Lys Gly Ala Ile Phe
305                 310                 315                 320
Gly Gly Phe Lys Ser Lys Asp Ser Val Pro Lys Leu Val Ala Asp Phe
                325                 330                 335
Met Ala Lys Lys Phe Ala Leu Asp Pro Leu Ile Thr His Val Leu Pro
            340                 345                 350
Phe Glu Lys Ile Asn Glu Gly Phe Asp Leu Leu Arg Ser Gly Glu Ser
        355                 360                 365
Ile Arg Thr Ile Leu Thr Phe
    370                 375

<210> SEQ ID NO 47
<211> LENGTH: 9089
<212> TYPE: DNA
<213> ORGANISM: artificial sequence
<220> FEATURE:
<223> OTHER INFORMATION: constructed plasmid

<400> SEQUENCE: 47
```

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accataccac | agcttttcaa | ttcaattcat | catttttttt | ttattcttt | ttttgatttc | 240 |
| ggtttctttg | aaatttttt | gattcggtaa | tctccgaaca | aaggaagaa | cgaaggaagg | 300 |
| agcacagact | tagattggta | tatatacgca | tatgtagtgt | tgaagaaaca | tgaaattgcc | 360 |
| cagtattctt | aacccaactg | cacagaacaa | aaacctgcag | gaaacgaaga | taaatcatgt | 420 |
| cgaaagctac | atataaggaa | cgtgctgcta | ctcatcctag | tcctgttgct | gccaagctat | 480 |
| ttaatatcat | gcacgaaaag | caaacaaact | tgtgtgcttc | attggatgtt | cgtaccacca | 540 |
| aggaattact | ggagttagtt | gaagcattag | gtcccaaaat | ttgtttacta | aaaacacatg | 600 |
| tggatatctt | gactgatttt | tccatggagg | gcacagttaa | gccgctaaag | gcattatccg | 660 |
| ccaagtacaa | ttttttactc | ttcgaagaca | gaaaatttgc | tgacattggt | aatacagtca | 720 |
| aattgcagta | ctctgcgggt | gtatacgaaa | tagcagaatg | ggcagacatt | acgaatgcac | 780 |
| acggtgtggt | gggcccaggt | attgttagcg | gtttgaagca | ggcggcagaa | gaagtaacaa | 840 |
| aggaacctag | aggcctttg | atgttagcag | aattgtcatg | caagggctcc | ctatctactg | 900 |
| gagaatatac | taagggtact | gttgacattg | cgaagagcga | caaagatttt | gttatcggct | 960 |
| ttattgctca | aagagacatg | ggtggaagag | atgaaggtta | cgattggttg | attatgacac | 1020 |
| ccggtgtggg | tttagatgac | aagggagacg | cattgggtca | acagtataga | accgtggatg | 1080 |
| atgtggtctc | tacaggatct | gacattatta | ttgttggaag | aggactattt | gcaagggaa | 1140 |
| gggatgctaa | ggtagagggt | gaacgttaca | gaaaagcagg | ctgggaagca | tatttgagaa | 1200 |
| gatgcggcca | gcaaaactaa | aaaactgtat | tataagtaaa | tgcatgtata | ctaaactcac | 1260 |
| aaattagagc | ttcaattta | ttatatcagt | tattaccca | tgcggtgtga | aataccgcac | 1320 |
| agatgcgtaa | ggagaaaata | ccgcatcagg | aaattgtaaa | cgttaatatt | ttgttaaaat | 1380 |
| tcgcgttaaa | ttttttgttaa | atcagctcat | tttttaacca | ataggccgaa | atcggcaaaa | 1440 |
| tcccttataa | atcaaaagaa | tagaccgaga | tagggttgag | tgttgttcca | gtttggaaca | 1500 |
| agagtccact | attaaagaac | gtggactcca | acgtcaaagg | gcgaaaaacc | gtctatcagg | 1560 |

```
gcgatggccc actacgtgaa ccatcaccct aatcaagttt tttggggtcg aggtgccgta    1620
aagcactaaa tcggaaccct aaagggagcc cccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagttggg    1920
taacgccagg gttttcccag tcacgacgtt gtaaaacgac ggccagtgag cgcgcgtaat    1980
acgactcact atagggcgaa ttgggtaccg gccccccct cgaggtcgac tggccattaa    2040
tctttcccat attagatttc gccaagccat gaaagttcaa gaaaggtctt tagacgaatt    2100
acccttcatt tctcaaactg gcgtcaaggg atcctggtat ggttttatcg ttttatttct    2160
ggttcttata gcatcgtttt ggacttctct gttcccatta ggcggttcag gagccagcgc    2220
agaatcattc tttgaaggat acttatcctt tccaattttg attgtctgtt acgttggaca    2280
taaactgtat actagaaatt ggactttgat ggtgaaacta aagatatgg atcttgatac    2340 cggcagaaaa caagtagatt tgactcttcg tagggaagaa atgaggattg agcgagaaac    2400
attagcaaaa agatccttcg taacaagatt tttacatttc tggtgttgaa gggaaagata    2460
tgagctatac agcggaattt ccatatcact cagattttgt tatctaattt tttccttccc    2520
acgtccgcgg gaatctgtgt atattactgc atctagatat atgttatctt atcttggcgc    2580
gtacatttaa ttttcaacgt attctataag aaattgcggg agtttttttc atgtagatga    2640
tactgactgc acgcaaatat aggcatgatt tataggcatg atttgatggc tgtaccgata    2700
ggaacgctaa gagtaacttc agaatcgtta tcctggcgga aaaaattcat ttgtaaactt    2760
taaaaaaaaa agccaatatc cccaaaatta ttaagagcgc ctccattatt aactaaaatt    2820
tcactcagca tccacaatgt atcaggtatc tactacagat attacatgtg gcgaaaaaga    2880
caagaacaat gcaatagcgc atcaagaaaa aacacaaagc tttcaatcaa tgaatcgaaa    2940
atgtcattaa aatagtatat aaattgaaac taagtcataa agctataaaa agaaaattta    3000
tttaaatgca agatttaaag taaattcacg gccctgcagg ccctaacctg ctaggacaca    3060
acgtctttgc ctggtaaagt ttctagctga cgtgattcct tcacctgtgg atccggcaat    3120
tgtaaaggtt gtgaaaccct cagcttcata accgacacct gcaaatgact ttgcattctt    3180
aacaaagata gttgtatcaa tttcacgttc gaatctatta aggttatcga tgttcttaga    3240
ataaatgtag gcggaatgtt ttctattctg ctcagctatc ttggcgtatt taatggcttc    3300
atcaatgtcc ttcactctaa ctataggcaa aattggcatc atcaactccg tcataacgaa    3360
cggatggttt gcgttgactt cacaaataat acactttaca ttacttggtg actctacatc    3420
tatttcatcc aaaaacagtt tagcgtcctt accaacccac ttcttattaa tgaaatattc    3480
ttgagtttca ttgttctttt gaagaacaag gtctatcagc ttggatactt ggtcttcatt    3540
gataatgacg gcgttgtttt tcaacatgtt agagatcaga tcatctgcaa cgttttcaaa    3600
cacgaacact tcttttttccg cgatacaagg aagattgttg tcaaacgaac aaccttcaat    3660
aatgcttctg ccggccttct cgatatctgc tgtatcgtct acaataaccg gaggattacc    3720
cgcgccagct ccgatggcct ttttaccaga attaagaagg ttttttacca tacccgggcc    3780
acccgtaccg cacaacaatt ttatggatgg atgtttgata atagcgtcta aactttccat    3840
agttgggttc tttatagtag tgacaaggtt ttcaggtcca ccacagctaa ttatggcttt    3900
```

```
gtttatcatt tctactgcga aagcgacaca cttttttggcg catgggtgac cattaaatac   3960
aactgcattc cccgcagcta tcatacctat agaattgcag ataacggttt ctgttggatt   4020
cgtgcttgga gttatagcgc cgataactcc gtatggactc atttcaacca ctgttagtcc   4080
attatcgccg gaccatgctg ttgttgtcag atcttcagtg cctggggtat acttggccac   4140
taattcatgt ttcaagattt tatcctcata ccttcccatg tgggtttcct ccaggatcat   4200
tgtggctaag acctctttat tctgtaatgc ggcttttctt atttcggtga ttattttctc   4260
tctttgttcc tttgtgtagt gtagggaaag aatcttttgt gcatgtactg cagaagaaat   4320
ggcattctca acatttttcaa atactccaaa acatgaagag ttatctttgt aattctttaa   4380
gttgatgttt tcaccattag tcttcacttt caagtctttg gtggttggga ttaaggtatc   4440
tttatccatg gtgtttgttt atgtgtgttt attcgaaact aagttcttgg tgttttaaaa   4500
ctaaaaaaaa gactaactat aaaagtagaa tttaagaagt ttaagaaata gatttacaga   4560
attacaatca atacctaccg tctttatata cttattagtc aagtagggga ataatttcag   4620
ggaactggtt tcaacctttt ttttcagctt tttccaaatc agagagagca gaaggtaata   4680
gaaggtgtaa gaaaatgaga tagatacatg cgtgggtcaa ttgccttgtg tcatcattta   4740
ctccaggcag gttgcatcac tccattgagg ttgtgcccgt ttttgcctg tttgtgcccc    4800 tgttctctgt agttgcgcta agagaatgga cctatgaact gatggttggt gaagaaaaca   4860
atattttggt gctgggattc ttttttttttc tggatgccag cttaaaaagc gggctccatt   4920
atatttagtg gatgccagga ataaactgtt cacccagaca cctacgatgt tatatattct   4980
gtgtaacccg cccctatttt tgggcatgta cgggttacag cagaattaaa aggctaattt   5040
tttgactaaa taaagttagg aaaatcacta ctattaatta tttacgtatt ctttgaaatg   5100
gcagtattga taatgataaa ctcgaactga aaaagcgtgt ttttttattca aaatgattct   5160 aactcccctta cgtaatcaag gaatctttttt gccttggcct ccgcgtcatt aaacttcttg   5220
ttgttgacgc taacattcaa cgctagtata tattcgtttt tttcaggtaa gttcttttca   5280
acgggtctta ctgatgaggc agtcgcgtct gaacctgtta agaggtcaaa tatgtcttct   5340
tgaccgtacg tgtcttgcat gttattagct ttgggaattt gcatcaagtc ataggaaaat   5400
ttaaatcttg gctctcttgg gctcaaggtg acaaggtcct cgaaaatagg gcgcgcccca   5460
ccgcggtgga gctccagctt ttgttccctt tagtgagggt taattgcgcg cttgcgtaa    5520 tcatggtcat agctgtttcc tgtgtgaaat tgttatccgc tcacaattcc acacaacata   5580
ggagccggaa gcataaagtg taaagcctgg ggtgcctaat gagtgaggta actcacatta   5640
attgcgttgc gctcactgcc cgctttccag tcgggaaacc tgtcgtgcca gctgcattaa   5700
tgaatcggcc aacgcgcggg gagaggcggt ttgcgtattg ggcgctcttc cgcttcctcg   5760
ctcactgact cgctgcgctc ggtcgttcgg ctgcggcgag cggtatcagc tcactcaaag   5820
gcggtaatac ggttatccac agaatcaggg gataacgcag gaagaacat gtgagcaaaa    5880 ggccagcaaa aggccaggaa ccgtaaaaag gccgcgttgc tggcgttttt ccataggctc   5940
cgcccccctg acgagcatca caaaaatcga cgctcaagtc agaggtggcg aaacccgaca   6000
ggactataaa gataccaggc gtttccccct ggaagctccc tcgtgcgctc tcctgttccg   6060
accctgccgc ttaccggata cctgtccgcc tttctccctt cgggaagcgt ggcgctttct   6120
catagctcac gctgtaggta tctcagttcg gtgtaggtcg ttcgctccaa gctgggctgt   6180
gtgcacgaac ccccgttca gcccgaccgc tgcgccttat ccggtaacta tcgtcttgag    6240
tccaacccgg taagacacga cttatcgcca ctggcagcag ccactggtaa caggattagc   6300
```

```
agagcgaggt atgtaggcgg tgctacagag ttcttgaagt ggtggcctaa ctacggctac   6360
actagaagga cagtatttgg tatctgcgct ctgctgaagc cagttacctt cggaaaaaga   6420
gttggtagct cttgatccgg caaacaaacc accgctggta gcggtggttt ttttgtttgc   6480
aagcagcaga ttacgcgcag aaaaaaagga tctcaagaag atcctttgat cttttctacg   6540
gggtctgacg ctcagtggaa cgaaaactca cgttaaggga ttttggtcat gagattatca   6600
aaaaggatct tcacctagat ccttttaaat taaaaatgaa gttttaaatc aatctaaagt   6660
atatatgagt aaacttggtc tgacagttac caatgcttaa tcagtgaggc acctatctca   6720
gcgatctgtc tatttcgttc atccatagtt gcctgactcc ccgtcgtgta gataactacg   6780
atacgggagg gcttaccatc tggccccagt gctgcaatga taccgcgaga cccacgctca   6840
ccggctccag atttatcagc aataaaccag ccagccggaa gggccgagcg cagaagtggt   6900
cctgcaactt tatccgcctc catccagtct attaattgtt gccgggaagc tagagtaagt   6960
agttcgccag ttaatagttt gcgcaacgtt gttgccattg ctacaggcat cgtggtgtca   7020
cgctcgtcgt ttggtatggc ttcattcagc tccggttccc aacgatcaag gcgagttaca   7080
tgatccccca tgttgtgcaa aaaagcggtt agctccttcg gtcctccgat cgttgtcaga   7140
agtaagttgg ccgcagtgtt atcactcatg gttatggcag cactgcataa ttctcttact   7200
gtcatgccat ccgtaagatg cttttctgtg actggtgagt actcaaccaa gtcattctga   7260
gaatagtgta tgcggcgacc gagttgctct tgcccggcgt caatacggga taataccgcg   7320
ccacatagca gaactttaaa agtgctcatc attggaaaac gttcttcggg gcgaaaactc   7380
tcaaggatct taccgctgtt gagatccagt tcgatgtaac ccactcgtgc acccaactga   7440
tcttcagcat cttttacttt caccagcgtt tctgggtgag caaaaacagg aaggcaaaat   7500
gccgcaaaaa agggaataag ggcgacacgg aaatgttgaa tactcatact cttccttttt   7560
caatattatt gaagcattta tcagggttat tgtctcatga gcggatacat atttgaatgt   7620
atttagaaaa ataaacaaat aggggttccg cgcacatttc cccgaaaagt gccacctgaa   7680
cgaagcatct gtgcttcatt tgtagaacaa aaaatgcaac gcgagagcgc taattttttca   7740 aacaaagaat ctgagctgca ttttttacaga acagaaatgc aacgcgaaag cgctatttta   7800
ccaacgaaga atctgtgctt cattttttgta aaacaaaaat gcaacgcgag agcgctaatt   7860
tttcaaacaa agaatctgag ctgcattttt acagaacaga atgcaacgc gagagcgcta   7920 ttttaccaac aaagaatcta tacttctttt tgttctaca aaaatgcatc ccgagagcgc   7980
tattttccta caaagcatc ttagattact tttttctcc tttgtgcgct ctataatgca   8040
gtctcttgat aacttttttgc actgtaggtc cgttaaggtt agaagaaggc tactttggtg   8100
tctattttct cttccataaa aaaagcctga ctccacttcc cgcgtttact gattactagc   8160
gaagctgcgg gtgcattttt tcaagataaa ggcatccccg attatattct ataccgatgt   8220
ggattgcgca tactttgtga acagaaagtg atagcgttga tgattcttca ttggtcagaa   8280
aattatgaac ggtttcttct attttgtctc tatatactac gtataggaaa tgtttacatt   8340
ttcgtattgt tttcgattca ctctatgaat agttcttact acaatttttt tgtctaaaga   8400
gtaatactag agataaacat aaaaaatgta gaggtcgagt ttagatgcaa gttcaaggag   8460
cgaaaggtgg atgggtaggt tatataggga tatagcacag agatatatag caaagagata   8520
cttttgagca atgtttgtgg aagcggtatt cgcaatattt tagtagctcg ttacagtccg   8580
gtgcgttttt ggttttttga aagtgcgtct tcagagcgct tttggttttc aaaagcgctc   8640
```

-continued

| | |
|---|---|
| tgaagttcct atactttcta gagaatagga acttcggaat aggaacttca aagcgtttcc | 8700 |
| gaaaacgagc gcttccgaaa atgcaacgcg agctgcgcac atacagctca ctgttcacgt | 8760 |
| cgcacctata tctgcgtgtt gcctgtatat atatatacat gagaagaacg gcatagtgcg | 8820 |
| tgtttatgct taaatgcgta cttatatgcg tctatttatg taggatgaaa ggtagtctag | 8880 |
| tacctcctgt gatattatcc cattccatgc ggggtatcgt atgcttcctt cagcactacc | 8940 |
| ctttagctgt tctatatgct gccactcctc aattggatta gtctcatcct tcaatgctat | 9000 |
| catttccttt gatattggat catactaaga aaccattatt atcatgacat taacctataa | 9060 |
| aaataggcgt atcacgaggc cctttcgtc | 9089 |

<210> SEQ ID NO 48
<211> LENGTH: 1023
<212> TYPE: DNA
<213> ORGANISM: Saccharomyces cerevisiae

<400> SEQUENCE: 48

| | |
|---|---|
| caccgcggtg gggcgcgccc tattttcgag gaccttgtca ccttgagccc aagagagcca | 60 |
| agatttaaat tttcctatga cttgatgcaa attcccaaag ctaataacat gcaagacacg | 120 |
| tacggtcaag aagacatatt tgacctctta acaggttcag acgcgactgc ctcatcagta | 180 |
| agacccgttg aaaagaactt acctgaaaaa aacgaatata tactagcgtt gaatgttagc | 240 |
| gtcaacaaca agaagtttaa tgacgcggag gccaaggcaa aaagattcct tgattacgta | 300 |
| agggagttag aatcattttg aataaaaaac acgcttttc agttcgagtt tatcattatc | 360 |
| aatactgcca tttcaaagaa tacgtaaata attaatagta gtgattttcc taactttatt | 420 |
| tagtcaaaaa attagccttt taattctgct gtaacccgta catgcccaaa ataggggcg | 480 |
| ggttacacag aatatataac atcgtaggtg tctgggtgaa cagtttattc ctggcatcca | 540 |
| ctaaatataa tggagcccgc tttttaagct ggcatccaga aaaaaaaga atcccagcac | 600 |
| caaaatattg ttttcttcac caaccatcag ttcataggtc cattctctta gcgcaactac | 660 |
| agagaacagg ggcacaaaca ggcaaaaaac gggcacaacc tcaatggagt gatgcaacct | 720 |
| gcctggagta aatgatgaca caaggcaatt gacccacgca tgtatctatc tcattttctt | 780 |
| acaccttcta ttaccttctg ctctctctga tttggaaaaa gctgaaaaaa aaggttgaaa | 840 |
| ccagttccct gaaattattc ccctacttga ctaataagta tataaagacg gtaggtattg | 900 |
| attgtaattc tgtaaatcta tttcttaaac ttcttaaatt ctacttttat agttagtctt | 960 |
| ttttttagtt ttaaaacacc aagaacttag tttcgaataa acacacataa actagtaaac | 1020 |
| aaa | 1023 |

<210> SEQ ID NO 49
<211> LENGTH: 21
<212> TYPE: DNA
<213> ORGANISM: artificial sequence
<220> FEATURE:
<223> OTHER INFORMATION: primer

<400> SEQUENCE: 49

| | |
|---|---|
| caaaagctga gctccaccgc g | 21 |

<210> SEQ ID NO 50
<211> LENGTH: 44
<212> TYPE: DNA
<213> ORGANISM: artificial sequence
<220> FEATURE:
<223> OTHER INFORMATION: primer

```
<400> SEQUENCE: 50
gtttactagt ttatgtgtgt ttattcgaaa ctaagttctt ggtg                44

<210> SEQ ID NO 51
<211> LENGTH: 8994
<212> TYPE: DNA
<213> ORGANISM: artificial sequence
<220> FEATURE:
<223> OTHER INFORMATION: constructed plasmid

<400> SEQUENCE: 51
ctagttctag agcggccgcc accgcggtgg agctccagct tttgttccct ttagtgaggg     60
ttaattgcgc gcttggcgta atcatggtca tagctgtttc ctgtgtgaaa ttgttatccg    120
ctcacaattc cacacaacat aggagccgga agcataaagt gtaaagcctg gggtgcctaa    180
tgagtgaggt aactcacatt aattgcgttg cgctcactgc ccgctttcca gtcgggaaac    240
ctgtcgtgcc agctgcatta tgaatcggc caacgcgcgg ggagaggcgg tttgcgtatt    300 ggcgctctt ccgcttcctc gctcactgac tcgctgcgct cggtcgttcg ctgcggcga    360 gcggtatcag ctcactcaaa ggcggtaata cggttatcca cagaatcagg ggataacgca    420
ggaaagaaca tgtgagcaaa aggccagcaa aaggccagga accgtaaaaa ggccgcgttg    480
ctggcgtttt tccataggct ccgcccccct gacgagcatc acaaaaatcg acgctcaagt    540
cagaggtggc gaaacccgac aggactataa agataccagg cgtttccccc tggaagctcc    600
ctcgtgcgct ctcctgttcc gaccctgccg cttaccggat acctgtccgc ctttctccct    660
tcgggaagcg tggcgctttc tcatagctca cgctgtaggt atctcagttc ggtgtaggtc    720
gttcgctcca agctgggctg tgtgcacgaa ccccccgttc agcccgaccg ctgcgcctta    780
tccggtaact atcgtcttga gtccaacccg gtaagacacg acttatcgcc actggcagca    840
gccactggta acaggattag cagagcgagg tatgtaggcg gtgctacaga gttcttgaag    900
tggtggccta actacggcta cactagaagg acagtatttg gtatctgcgc tctgctgaag    960
ccagttacct tcggaaaaag agttggtagc tcttgatccg gcaaacaaac caccgctggt   1020
agcggtggtt tttttgtttg caagcagcag attacgcgca gaaaaaaagg atctcaagaa   1080
gatcctttga tcttttctac ggggtctgac gctcagtgga acgaaaactc acgttaaggg   1140
attttggtca tgagattatc aaaaaggatc ttcacctaga tccttttaaa ttaaaaatga   1200
agttttaaat caatctaaag tatatatgag taaacttggt ctgacagtta ccaatgctta   1260
atcagtgagg cacctatctc agcgatctgt ctatttcgtt catccatagt tgcctgactc   1320
cccgtcgtgt agataactac gatacgggag ggcttaccat ctggccccag tgctgcaatg   1380
ataccgcgag acccacgctc accggctcca gatttatcag caataaacca gccagccgga   1440
agggccgagc gcagaagtgg tcctgcaact ttatccgcct ccatccagtc tattaattgt   1500
tgccgggaag ctagagtaag tagttcgcca gttaatagtt tgcgcaacgt tgttgccatt   1560
gctacaggca tcgtggtgtc acgctcgtcg tttggtatgg cttcattcag ctccggttcc   1620
caacgatcaa ggcgagttac atgatccccc atgttgtgca aaaaagcggt tagctccttc   1680
ggtcctccga tcgttgtcag aagtaagttg gccgcagtgt tatcactcat ggttatggca   1740
gcactgcata attctcttac tgtcatgcca tccgtaagat gcttttctgt gactggtgag   1800
tactcaacca agtcattctg agaatagtgt atgcggcgac cgagttgctc ttgcccggcg   1860
tcaatacggg ataataccgc gccacatagc agaactttaa aagtgctcat cattggaaaa   1920
```

```
cgttcttcgg ggcgaaaact ctcaaggatc ttaccgctgt tgagatccag ttcgatgtaa    1980
cccactcgtg cacccaactg atcttcagca tcttttactt tcaccagcgt ttctgggtga    2040
gcaaaaacag gaaggcaaaa tgccgcaaaa aagggaataa gggcgacacg gaaatgttga    2100
atactcatac tcttcctttt tcaatatttat tgaagcattt atcagggtta ttgtctcatg    2160
agcggataca tatttgaatg tatttagaaa aataaacaaa taggggttcc gcgcacattt    2220
ccccgaaaag tgccacctga acgaagcatc tgtgcttcat tttgtagaac aaaaatgcaa    2280
cgcgagagcg ctaattttc aaacaaagaa tctgagctgc attttacag aacagaaatg     2340 caacgcgaaa gcgctatttt accaacgaag aatctgtgct tcattttgt aaaacaaaaa     2400 tgcaacgcga gagcgctaat ttttcaaaca aagaatctga gctgcatttt tacagaacag    2460
aaatgcaacg cgagagcgct attttaccaa caaagaatct atacttcttt tttgttctac    2520
aaaaatgcat cccgagagcg ctattttct aacaaagcat cttagattac tttttttctc     2580
ctttgtgcgc tctataatgc agtctcttga taacttttg cactgtaggt ccgttaaggt     2640
tagaagaagg ctactttggt gtctattttc tcttccataa aaaagcctg actccacttc     2700 ccgcgtttac tgattactag cgaagctgcg ggtgcatttt ttcaagataa aggcatcccc    2760
gattatattc tataccgatg tggattgcgc atactttgtg aacagaaagt gatagcgttg    2820
atgattcttc attggtcaga aaattatgaa cggtttcttc tatttgtct ctatatacta     2880 cgtataggaa atgtttacat tttcgtattg ttttcgattc actctatgaa tagttcttac    2940
tacaattttt ttgtctaaag agtaatacta gagataaaca taaaaaatgt agaggtcgag    3000
tttagatgca agttcaagga gcgaaaggtg gatgggtagg ttatatagg atatagcaca     3060 gagatatata gcaaagagat acttttgagc aatgtttgtg gaagcggtat tcgcaatatt    3120
ttagtagctc gttacagtcc ggtgcgtttt tggttttttg aaagtgcgtc ttcagagcgc    3180
ttttggtttt caaaagcgct ctgaagttcc tatactttct agagaatagg aacttcggaa    3240
taggaacttc aaagcgtttc cgaaaacgag cgcttccgaa aatgcaacgc gagctgcgca    3300
catacagctc actgttcacg tcgcacctat atctgcgtgt tgcctgtata tatatataca    3360
tgagaagaac ggcatagtgc gtgtttatgc ttaaatgcgt acttatatgc gtctatttat    3420
gtaggatgaa aggtagtcta gtacctcctg tgatattatc ccattccatg cggggtatcg    3480
tatgcttcct tcagcactac cctttagctg ttctatatgc tgccactcct caattggatt    3540
agtctcatcc ttcaatgcta tcatttcctt tgatattgga tcatactaag aaaccattat    3600
tatcatgaca ttaacctata aaataggcg tatcacgagg ccctttcgtc tcgcgcgttt     3660
cggtgatgac ggtgaaaacc tctgacacat gcagctcccg gagacggtca cagcttgtct    3720
gtaagcggat gccgggagca gacaagcccg tcagggcgcg tcagcgggtg ttggcgggtg    3780
tcggggctgg cttaactatg cggcatcaga gcagattgta ctgagagtgc accatatcga    3840
ctacgtcgta aggccgtttc tgacagagta aaattcttga gggaacttc accattatgg    3900 gaaatgcttc aagaaggtat tgacttaaac tccatcaaat ggtcaggtca ttgagtgttt    3960
tttatttgtt gtatttttt tttttagag aaaatcctcc aatatcaaat taggaatcgt     4020
agtttcatga ttttctgtta cacctaactt tttgtgtggt gccctcctcc ttgtcaatat    4080
taatgttaaa gtgcaattct tttccttat cacgttgagc cattagtatc aatttgctta     4140
cctgtattcc tttactatcc tccttttct ccttcttgat aaatgtatgt agattgcgta     4200
tatagtttcg tctaccctat gaacatattc cattttgtaa tttcgtgtcg tttctattat    4260
gaatttcatt tataaagttt atgtacaaat atcataaaaa aagagaatct ttttaagcaa    4320
```

```
ggattttctt aacttcttcg gcgacagcat caccgacttc ggtggtactg ttggaaccac   4380
ctaaatcacc agttctgata cctgcatcca aaaccttttt aactgcatct tcaatggcct   4440
taccttcttc aggcaagttc aatgacaatt tcaacatcat tgcagcagac aagatagtgg   4500
cgatagggtc aaccttattc tttggcaaat ctggagcaga accgtggcat ggttcgtaca   4560
aaccaaatgc ggtgttcttg tctggcaaag aggccaagga cgcagatggc aacaaaccca   4620
aggaacctgg gataacggag gcttcatcgg agatgatatc accaaacatg ttgctggtga   4680
ttataatacc atttaggtgg gttgggttct taactaggat catggcggca gaatcaatca   4740
attgatgttg aaccttcaat gtagggaatt cgttcttgat ggtttcctcc acagtttttc   4800
tccataatct tgaagaggcc aaaagattag ctttatccaa ggaccaaata ggcaatggtg   4860
gctcatgttg tagggccatg aaagcggcca ttcttgtgat tctttgcact tctggaacgg   4920
tgtattgttc actatcccaa gcgacaccat caccatcgtc ttcctttctc ttaccaaagt   4980
aaatacctcc cactaattct ctgacaacaa cgaagtcagt acctttagca aattgtggct   5040
tgattggaga taagtctaaa agagagtcgg atgcaaagtt acatggtctt aagttggcgt   5100
acaattgaag ttcttacgg atttttagta aaccttgttc aggtctaaca ctaccggtac   5160
cccatttagg accagccaca gcacctaaca aaacggcatc aaccttcttg gaggcttcca   5220
gcgcctcatc tggaagtggg acacctgtag catcgatagc agcaccacca attaaatgat   5280
tttcgaaatc gaacttgaca ttggaacgaa catcagaaat agctttaaga accttaatgg   5340
cttcggctgt gatttcttga ccaacgtggt cacctggcaa aacgacgatc ttcttagggg   5400
cagacatagg ggcagacatt agaatggtat atccttgaaa tatatatata tattgctgaa   5460
atgtaaaagg taagaaaagt tagaaagtaa gacgattgct aaccacctat tggaaaaaac   5520
aataggtcct taaataatat tgtcaacttc aagtattgtg atgcaagcat ttagtcatga   5580
acgcttctct attctatatg aaaagccggt tccggcctct caccttttcct ttttctccca   5640
attttcagt tgaaaaaggt atatgcgtca ggcgacctct gaaattaaca aaaaatttcc   5700
agtcatcgaa tttgattctg tgcgatagcg cccctgtgtg ttctcgttat gttgaggaaa   5760
aaaataatgg ttgctaagag attcgaactc ttgcatctta cgatacctga gtattcccac   5820
agttaactgc ggtcaagata tttcttgaat caggcgcctt agaccgctcg gccaaacaac   5880
caattacttg ttgagaaata gagtataatt atcctataaa tataacgttt ttgaacacac   5940
atgaacaagg aagtacagga caattgattt tgaagagaat gtggattttg atgtaattgt   6000
tgggattcca tttttaataa ggcaataata ttaggtatgt ggatatacta gaagttctcc   6060
tcgaccgtcg atatgcggtg tgaaataccg cacagatgcg taaggagaaa ataccgcatc   6120
aggaaattgt aaacgttaat attttgttaa aattcgcgtt aaattttgt taaatcagct   6180
catttttaa ccataggcc gaaatcggca aaatccctta taaatcaaaa gaatagaccg   6240
agatagggtt gagtgttgtt ccagtttgga acaagagtcc actattaaag aacgtggact   6300
ccaacgtcaa agggcgaaaa accgtctatc agggcgatgg cccactacgt gaaccatcac   6360
cctaatcaag ttttttgggg tcgaggtgcc gtaaagcact aaatcggaac cctaaaggga   6420
gcccccgatt tagagcttga cggggaaagc cggcgaacgt ggcgagaaag gaagggaaga   6480
aagcgaaagg agcgggcgct agggcgctgg caagtgtagc ggtcacgctg cgcgtaacca   6540
ccacacccgc cgcgcttaat gcgccgctac agggcgcgtc gcgccattcg ccattcaggc   6600
tgcgcaactg ttgggaaggg cgatcggtgc gggcctcttc gctattacgc cagctggcga   6660
```

```
aaggggatg tgctgcaagg cgattaagtt gggtaacgcc agggttttcc cagtcacgac      6720
gttgtaaaac gacggccagt gagcgcgcgt aatacgactc actatagggc gaattgggta      6780
ccgggccccc cctcgaggtc gacggtatcg ataagcttga tatcgaattc ctgcagcccg      6840
ggggatccgc atgcttgcat ttagtcgtgc aatgtatgac tttaagattt gtgagcagga      6900
agaaaaggga gaatcttcta acgataaacc cttgaaaaac tgggtagact acgctatgtt      6960
gagttgctac gcaggctgca caattacacg agaatgctcc cgcctaggat ttaaggctaa      7020
gggacgtgca atgcagacga cagatctaaa tgaccgtgtc ggtgaagtgt tcgccaaact      7080
tttcggttaa cacatgcagt gatgcacgcg cgatggtgct aagttacata tatatatata      7140
tatatatata tagccatagt gatgtctaag taacctttat ggtatatttc ttaatgtgga      7200
aagatactag cgcgcgcacc cacacacaag cttcgtcttt tcttgaagaa aagaggaagc      7260
tcgctaaatg ggattccact ttccgttccc tgccagctga tggaaaaagg ttagtggaac      7320
gatgaagaat aaaagagag atccactgag gtgaaatttc agctgacagc gagtttcatg      7380
atcgtgatga acaatggtaa cgagttgtgg ctgttgccag ggagggtggt tctcaacttt      7440
taatgtatgg ccaaatcgct acttgggttt gttatataac aaagaagaaa taatgaactg      7500
attctcttcc tccttcttgt cctttcttaa ttctgttgta attaccttcc tttgtaattt      7560
tttttgtaat tattcttctt aataatccaa acaaacacac atattacaat agctagctga      7620
ggatgaaggc attagtttat catggggatc acaaaatttc gttagaagac aaaccaaaac      7680
ccactctgca gaaaccaaca gacgttgtgg ttagggtgtt gaaaacaaca atttgcggta      7740
ctgacttggg aatatacaaa ggtaagaatc ctgaagtggc agatggcaga atcctgggtc      7800
atgagggcgt tggcgtcatt gaagaagtgg gcgaatccgt gacacaattc aaaaaggggg      7860
ataaagtttt aatctcctgc gttactagct gtggatcgtg tgattattgc aagaagcaac      7920
tgtattcaca ctgtagagac ggtggctgga ttttaggtta catgatcgac ggtgtccaag      7980
ccgaatacgt cagaatacca catgctgaca attcattgta taagatcccg caaactatcg      8040
atgatgaaat tgcagtacta ctgtccgata ttttacctac tggacatgaa attggtgttc      8100
aatatggtaa cgttcaacca ggcgatgctg tagcaattgt aggagcaggt cctgttggaa      8160
tgtcagtttt gttaactgct caattttact cgcctagtac cattattgtt atcgacatgg      8220
acgaaaaccg tttacaatta gcgaaggagc ttggggccac acacactatt aactccggta      8280
ctgaaaatgt tgtcgaagct gtgcatcgta tagcagccga aggagtggat gtagcaatag      8340
aagctgttgg tatacccgca acctgggaca tctgtcagga aattgtaaaa cccggcgctc      8400
atattgccaa cgtgggagtt catggtgtta aggtggactt tgaaattcaa aagttgtgga      8460
ttaagaatct aaccatcacc actggtttgg ttaacactaa tactacccca atgttgatga      8520
aggtagcctc tactgataaa ttgcctttaa agaaaatgat tactcacagg tttgagttag      8580
ctgaaatcga acacgcatat caggttttct tgaatggcgc taagaaaaaa gctatgaaga      8640
ttattctatc taatgcaggt gccgcctaat taattaagag taagcgaatt tcttatgatt      8700
tatgattttt attattaaat aagttataaa aaaataagt gtatacaaat tttaaagtga      8760
ctcttaggtt ttaaaacgaa aattcttatt cttgagtaac tctttcctgt aggtcaggtt      8820
gctttctcag gtatagcatg aggtcgctct tattgaccac acctctaccg gcatgccgag      8880
caaatgcctg caaatcgctc cccatttcac ccaattgtag atatgctaac tccagcaatg      8940
agttgatgaa tctcggtgtg tattttatgt cctcagagga caacacctgt ggta           8994
```

```
<210> SEQ ID NO 52
<211> LENGTH: 753
<212> TYPE: DNA
<213> ORGANISM: Saccharomyces cerevisiae

<400> SEQUENCE: 52
gcatgcttgc atttagtcgt gcaatgtatg actttaagat tgtgagcag gaagaaaagg      60 gagaatcttc taacgataaa cccttgaaaa actgggtaga ctacgctatg ttgagttgct     120
acgcaggctg cacaattaca cgagaatgct cccgcctagg atttaaggct aagggacgtg    180
caatgcagac gacagatcta aatgaccgtg tcggtgaagt gttcgccaaa ctttcggtt      240 aacacatgca gtgatgcacg cgcgatggtg ctaagttaca tatatatata tatagccata    300
gtgatgtcta agtaacctt atggtatatt tcttaatgtg gaaagatact agcgcgcgca     360
cccacacaca agcttcgtct tttcttgaag aaaagaggaa gctcgctaaa tgggattcca    420 cttccgttc cctgccagct gatggaaaaa ggttagtgga acgatgaaga ataaaaagag    480
agatccactg aggtgaaatt tcagctgaca gcgagtttca tgatcgtgat gaacaatggt    540
aacgagttgt ggctgttgcc agggagggtg gttctcaact tttaatgtat ggccaaatcg    600
ctacttgggt ttgttatata acaaagaaga ataatgaac tgattctctt cctccttctt     660 gtccttttctt aattctgttg taattacctt cctttgtaat ttttttttgta attattcttc  720 ttaataatcc aaacaaacac acatattaca ata                                  753

<210> SEQ ID NO 53
<211> LENGTH: 316
<212> TYPE: DNA
<213> ORGANISM: Saccharomyces cerevisiae

<400> SEQUENCE: 53
gagtaagcga atttcttatg atttatgatt tttattatta aataagttat aaaaaaaata    60
agtgtataca aattttaaag tgactcttag gttttaaaac gaaaattctt attcttgagt    120 aactcttttcc tgtaggtcag gttgctttct caggtatagc atgaggtcgc tcttattgac  180
cacacctcta ccggcatgcc gagcaaatgc ctgcaaatcg ctccccattt cacccaattg   240
tagatatgct aactccagca atgagttgat gaatctcggt gtgtatttta tgtcctcaga   300
ggacaacacc tgtggt                                                    316

<210> SEQ ID NO 54
<211> LENGTH: 39
<212> TYPE: DNA
<213> ORGANISM: artificial sequence
<220> FEATURE:
<223> OTHER INFORMATION: primer

<400> SEQUENCE: 54
cacacatatt acaatagcta gctgaggatg aaagctctg                            39

<210> SEQ ID NO 55
<211> LENGTH: 39
<212> TYPE: DNA
<213> ORGANISM: artificial sequence
<220> FEATURE:
<223> OTHER INFORMATION: primer

<400> SEQUENCE: 55
cagagctttc atcctcagct agctattgta atatgtgtg                            39

<210> SEQ ID NO 56
```

<211> LENGTH: 9491
<212> TYPE: DNA
<213> ORGANISM: artificial sequence
<220> FEATURE:
<223> OTHER INFORMATION: constructed plasmid

<400> SEQUENCE: 56

```
tcgcgcgttt cggtgatgac ggtgaaaacc tctgacacat gcagctcccg gagacggtca      60
cagcttgtct gtaagcggat gccgggagca gacaagcccg tcaggcgcg tcagcggtg       120
ttggcgggtg tcggggctgg cttaactatg cggcatcaga gcagattgta ctgagagtgc    180
accataaatt cccgttttaa gagcttggtg agcgctagga gtcactgcca ggtatcgttt     240
gaacacggca ttagtcaggg aagtcataac acagtccttt cccgcaattt tcttttttcta   300
ttactcttgg cctcctctag tacactctat attttttat gcctcggtaa tgattttcat      360
tttttttttt cccctagcgg atgactcttt tttttcttta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaagag gcagaagcag tagcagaaca ggccacacaa tcgcaagtga     660
ttaacgtcca cacaggtata gggttctgg accatatgat acatgctctg ccaagcatt      720
ccggctggtc gctaatcgtt gagtgcattg gtgacttaca catagacgac catcacacca    780
ctgaagactg cgggattgct ctcggtcaag cttttaaaga ggccctactg gcgcgtggag     840
taaaaaggtt tggatcagga tttgcgcctt tggatgaggc actttccaga gcggtggtag    900
atctttcgaa caggccgtac gcagttgtcg aacttggttt gcaaagggag aaagtaggag     960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat  1200
atacatgtgt atatatgtat acctatgaat gtcagtaagt atgtatacga acagtatgat  1260
actgaagatg acaaggtaat gcatcattct atacgtgtca ttctgaacga ggcgcgcttt  1320
cctttttttct ttttgctttt tctttttttt tctcttgaac tcgacggatc tatgcggtgt  1380
gaaataccgc acagatgcgt aaggagaaaa taccgcatca ggaaattgta acgttaata    1440
ttttgttaaa attcgcgtta aatttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa  1620
ccgtctatca gggcgatggc ccactacgtg aaccatcacc ctaatcaagt tttttgggt    1680
cgaggtgccg taaagcacta atcggaacc ctaaagggag cccccgattt agagcttgac    1740
ggggaaagcc ggcgaacgtg gcgagaaagg aaggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggatgt gctgcaaggc    1980
gattaagttg ggtaacgcca ggttttccc agtcacgacg ttgtaaaacg acggccagtg   2040
agcgcgcgta atacgactca ctatagggcg aattgggtac cgggccccc ctcgaggtcg    2100
acggcgcgcc actggtagag agcgactttg tatgcccaa ttgcgaaacc cgcgatatcc    2160
```

```
ttctcgattc tttagtaccc gaccaggaca aggaaaagga ggtcgaaacg tttttgaaga      2220
aacaagagga actacacgga agctctaaag atggcaacca gccagaaact aagaaaatga      2280
agttgatgga tccaactggc accgctggct tgaacaacaa taccagcctt ccaacttctg      2340
taaataacgg cggtacgcca gtgccaccag taccgttacc tttcggtata cctcctttcc      2400
ccatgtttcc aatgcccttc atgcctccaa cggctactat cacaaatcct catcaagctg      2460
acgcaagccc taagaaatga ataacaatac tgacagtact aaataattgc ctacttggct      2520
tcacatacgt tgcatacgtc gatatagata ataatgataa tgacagcagg attatcgtaa      2580
tacgtaatag ttgaaaatct caaaaatgtg tgggtcatta cgtaaataat gataggaatg      2640
ggattcttct atttttcctt tttccattct agcagccgtc gggaaaacgt ggcatcctct      2700
ctttcgggct caattggagt cacgctgccg tgagcatcct ctctttccat atctaacaac      2760
tgagcacgta accaatggaa aagcatgagc ttagcgttgc tccaaaaaag tattggatgg      2820
ttaataccat ttgtctgttc tcttctgact ttgactcctc aaaaaaaaaa aatctacaat      2880
caacagatcg cttcaattac gccctcacaa aaactttttt ccttcttctt cgcccacgtt      2940
aaattttatc cctcatgttg tctaacggat ttctgcactt gatttattat aaaaagacaa      3000
agacataata cttctctatc aatttcagtt attgttcttc cttgcgttat tcttctgttc      3060 ttcttttct tttgtcatat ataaccataa ccaagtaata catattcaaa ctagtatgac      3120
tgacaaaaaa actcttaaag acttaagaaa tcgtagttct gtttacgatt caatggttaa      3180
atcacctaat cgtgctatgt tgcgtgcaac tggtatgcaa gatgaagact ttgaaaaacc      3240
tatcgtcggt gtcatttcaa cttgggctga aaacacacct tgtaatatcc acttacatga      3300
ctttggtaaa ctagccaaag tcggtgttaa ggaagctggt gcttggccag ttcagttcgg      3360
aacaatcacg gtttctgatg aatcgccat gggaacccaa ggaatgcgtt tctccttgac       3420
atctcgtgat attattgcag attctattga agcagccatg ggaggtcata atgcggatgc      3480
ttttgtagcc attggcggtt gtgataaaaa catgcccggt tctgttatcg ctatggctaa      3540
catggatatc ccagccattt ttgcttacgg cggaacaatt gcacctggta atttagacgg      3600
caaagatatc gatttagtct ctgtctttga aggtgtcggc cattggaacc acggcgatat      3660
gaccaaagaa gaagttaaag ctttggaatg taatgcttgt cccggtcctg gaggctgcgg      3720
tggtatgtat actgctaaca caatggcgac agctattgaa gttttgggac ttagccttcc      3780
gggttcatct tctcacccgg ctgaatccgc agaaagaaa gcagatattg aagaagctgg      3840
tcgcgctgtt gtcaaaatgc tcgaaatggg cttaaaacct tctgacattt taacgcgtga      3900
agcttttgaa gatgctatta ctgtaactat ggctctggga ggttcaacca actcaaccct      3960
tcacctctta gctattgccc atgctgctaa tgtggaattg acacttgatg atttcaatac      4020
tttccaagaa aaagttcctc atttggctga tttgaaacct tctggtcaat atgtattcca      4080 agaccttac aaggtcggag gggtaccagc agttatgaaa tatctcctta aaaatggctt       4140
ccttcatggt gaccgtatca cttgtactgg caaaacagtc gctgaaaatt tgaaggcttt      4200
tgatgattta acacctggtc aaaaggttat tatgccgctt gaaaatccta acgtgaaga       4260 tggtccgctc attattctcc atggtaactt ggctccagac ggtgccgttg ccaaagtttc      4320
tggtgtaaaa gtgcgtcgtc atgtcggtcc tgctaaggtc tttaattctg aagaagaagc      4380
cattgaagct gtcttgaatg atgatattgt tgatggtgat ttgttgtcg tacgttttgt       4440 aggaccaaag ggcggtcctg gtatgcctga aatgctttcc ctttcatcaa tgattgttgg      4500
```

```
taaagggcaa ggtgaaaaag ttgcccttct gacagatggc cgcttctcag gtggtactta    4560
tggtcttgtc gtgggtcata tcgctcctga agcacaagat ggcggtccaa tcgcctacct    4620
gcaaacagga gacatagtca ctattgacca agacactaag gaattacact ttgatatctc    4680
cgatgaagag ttaaaacatc gtcaagagac cattgaattg ccaccgctct attcacgcgg    4740
tatccttggt aaatatgctc acatcgtttc gtctgcttct aggggagccg taacagactt    4800
ttggaagcct gaagaaactg gcaaaaaatg ttgtcctggt tgctgtggtt aagcggccgc    4860
gttaattcaa attaattgat atagttttt aatgagtatt gaatctgttt agaaataatg    4920
gaatattatt tttatttatt tatttatatt attggtcggc tcttttcttc tgaaggtcaa    4980
tgacaaaatg atatgaagga ataatgatt tctaaaattt tacaacgtaa gatattttta    5040
caaaagccta gctcatcttt tgtcatgcac tattttactc acgcttgaaa ttaacggcca    5100
gtccactgcg gagtcatttc aaagtcatcc taatcgatct atcgttttg atagctcatt    5160 ttggagttcg cgattgtctt ctgttattca caactgtttt aatttttatt tcattctgga    5220
actcttcgag ttctttgtaa agtctttcat agtagcttac tttatcctcc aacatatta    5280 acttcatgtc aatttcggct cttaaatttt ccacatcatc aagttcaaca tcatctttta    5340
acttgaattt attctctagc tcttccaacc aagcctcatt gctccttgat ttactggtga    5400
aaagtgatac actttgcgcg caatccaggt caaaactttc ctgcaaagaa ttcaccaatt    5460
tctcgacatc atagtacaat ttgttttgtt ctcccatcac aatttaatat acctgatgga    5520
ttcttatgaa gcgctgggta atggacgtgt cactctactt cgccttttc cctactcctt    5580 ttagtacgga agacaatgct aataaataag agggtaataa taatattatt aatcggcaaa    5640
aaagattaaa cgccaagcgt ttaattatca gaaagcaaac gtcgtaccaa tccttgaatg    5700
cttcccaatt gtatattaag agtcatcaca gcaacatatt cttgttatta aattaattat    5760
tattgatttt tgatattgta taaaaaaacc aaatatgtat aaaaaaagtg aataaaaaat    5820
accaagtatg gagaaatata ttagaagtct atacgttaaa ccaccgcggt ggagctccag    5880
cttttgttcc ctttagtgag ggttaattgc gcgcttggcg taatcatggt catagctgtt    5940
tcctgtgtga attgttatc cgctcacaat tccacacaac ataggagccg aagcataaa    6000 gtgtaaagcc tggggtgcct aatgagtgag gtaactcaca ttaattgcgt tgcgctcact    6060
gcccgctttc cagtcgggaa acctgtcgtg ccagctgcat taatgaatcg ccaacgcgc    6120 ggggagaggc ggtttgcgta ttgggcgctc ttccgcttcc tcgctcactg actcgctgcg    6180
ctcggtcgtt cggctgcggc gagcggtatc agctcactca aaggcggtaa tacggttatc    6240
cacagaatca ggggataacg caggaaagaa catgtgagca aaaggccagc aaaaggccag    6300
gaaccgtaaa aaggccgcgt tgctggcgtt tttccatagg ctccgccccc ctgacgagca    6360
tcacaaaaat cgacgctcaa gtcagaggtg gcgaaacccg acaggactat aaagatacca    6420
ggcgtttccc cctggaagct ccctcgtgcg ctctcctgtt ccgaccctgc cgcttaccgg    6480
atacctgtcc gcctttctcc cttcgggaag cgtggcgctt tctcatagct cacgctgtag    6540
gtatctcagt tcggtgtagg tcgttcgctc caagctgggc tgtgtgcacg aaccccccgt    6600
tcagcccgac cgctgcgcct tatccggtaa ctatcgtctt gagtccaacc cggtaagaca    6660
cgacttatcg ccactggcag cagccactgg taacaggatt agcagagcga ggtatgtagg    6720
cggtgctaca gagttcttga agtggtggcc taactacggc tacactagaa ggacagtatt    6780
tggtatctgc gctctgctga agccagttac cttcggaaaa agagttggta gctcttgatc    6840
cggcaaacaa accaccgctg gtagcggtgg tttttttgtt tgcaagcagc agattacgcg    6900
```

```
cagaaaaaaa ggatctcaag aagatccttt gatcttttct acggggtctg acgctcagtg   6960
gaacgaaaac tcacgttaag ggattttggt catgagatta tcaaaaagga tcttcaccta   7020 gatccttta  aattaaaaat gaagttttaa atcaatctaa agtatatatg agtaaacttg   7080
gtctgacagt taccaatgct taatcagtga ggcacctatc tcagcgatct gtctatttcg   7140
ttcatccata gttgcctgac tccccgtcgt gtagataact acgatacggg agggcttacc   7200
atctggcccc agtgctgcaa tgataccgcg agacccacgc tcaccggctc cagatttatc   7260
agcaataaac cagccagccg aagggccga  gcgcagaagt ggtcctgcaa ctttatccgc   7320
ctccatccag tctattaatt gttgccggga agctagagta agtagttcgc cagttaatag   7380
tttgcgcaac gttgttgcca ttgctacagg catcgtggtg tcacgctcgt cgtttggtat   7440
ggcttcattc agctccggtt cccaacgatc aaggcgagtt acatgatccc ccatgttgtg   7500
caaaaaagcg gttagctcct tcggtcctcc gatcgttgtc agaagtaagt tggccgcagt   7560
gttatcactc atggttatgg cagcactgca taattctctt actgtcatgc catccgtaag   7620
atgcttttct gtgactggtg agtactcaac caagtcattc tgagaatagt gtatgcggcg   7680
accgagttgc tcttgcccgg cgtcaatacg ggataatacc gcgccacata gcagaacttt   7740
aaaagtgctc atcattggaa aacgttcttc ggggcgaaaa ctctcaagga tcttaccgct   7800
gttgagatcc agttcgatgt aacccactcg tgcacccaac tgatcttcag catcttttac   7860
tttcaccagc gtttctgggt gagcaaaaac aggaaggcaa aatgccgcaa aaaagggaat   7920
aagggcgaca cggaaatgtt gaatactcat actcttcctt tttcaatatt attgaagcat   7980
ttatcagggt tattgtctca tgagcggata catatttgaa tgtatttaga aaaataaaca   8040
aataggggtt ccgcgcacat ttccccgaaa agtgccacct gaacgaagca tctgtgcttc   8100
attttgtaga acaaaaatgc aacgcgagag cgctaatttt tcaaacaaag aatctgagct   8160
gcatttttac agaacagaaa tgcaacgcga aagcgctatt ttaccaacga gaatctgtg   8220 cttcattttt gtaaaacaaa aatgcaacgc gagagcgcta attttcaaa  caaagaatct   8280 gagctgcatt tttacagaac agaaatgcaa cgcgagagcg ctattttacc aacaaagaat   8340
ctatacttct ttttgttct  acaaaaatgc atcccgagag cgctattttt ctaacaaagc   8400
atcttagatt actttttttc tcctttgtgc gctctataat gcagtctctt gataactttt   8460
tgcactgtag gtccgttaag gttagaagaa ggctactttg gtgtctattt tctcttccat   8520
aaaaaaagcc tgactccact tcccgcgttt actgattact agcgaagctg cgggtgcatt   8580
ttttcaagat aaaggcatcc ccgattatat tctataccga tgtggattgc gcatactttg   8640
tgaacagaaa gtgatagcgt tgatgattct tcattggtca gaaaattatg aacggtttct   8700
tctattttgt ctctatatac tacgtatagg aaatgtttac attttcgtat tgttttcgat   8760
tcactctatg aatagttctt actacaattt ttttgtctaa agagtaatac tagagataaa   8820
cataaaaaat gtagaggtcg agtttagatg caagttcaag gagcgaaagg tggatgggta   8880
ggttatatag ggatatagca cagagatata tagcaaagag atactttga  gcaatgtttg   8940 tggaagcggt attcgcaata ttttagtagc tcgttacagt ccggtgcgtt tttggttttt   9000
tgaaagtgcg tcttcagagc gcttttggtt ttcaaaagcg ctctgaagtt cctatacttt   9060
ctagagaata ggaacttcgg aataggaact tcaaagcgtt tccgaaaacg agcgcttccg   9120
aaaatgcaac gcgagctgcg cacatacagc tcactgttca cgtcgcacct atatctgcgt   9180
gttgcctgta tatatatata catgagaaga acggcatagt gcgtgtttat gcttaaatgc   9240
```

```
gtacttatat gcgtctattt atgtaggatg aaaggtagtc tagtacctcc tgtgatatta      9300
tcccattcca tgcggggtat cgtatgcttc cttcagcact acctttagc tgttctatat       9360 gctgccactc ctcaattgga ttagtctcat ccttcaatgc tatcatttcc tttgatattg     9420
gatcatctaa gaaaccatta ttatcatgac attaacctat aaaaataggc gtatcacgag      9480 gcccttcgt c                                                           9491
```

<210> SEQ ID NO 57
<211> LENGTH: 1000
<212> TYPE: DNA
<213> ORGANISM: Saccharymoces cerevisiae

<400> SEQUENCE: 57

```
gttaattcaa attaattgat atagtttttt aatgagtatt gaatctgttt agaaataatg       60
gaatattatt tttatttatt tatttatatt attggtcggc tcttttcttc tgaaggtcaa      120
tgacaaaatg atatgaagga ataatgatt tctaaaattt tacaacgtaa gatattttta      180
caaaagccta gctcatcttt tgtcatgcac tattttactc acgcttgaaa ttaacggcca      240
gtccactgcg gagtcatttc aaagtcatcc taatcgatct atcgttttg atagctcatt       300 ttggagttcg cgattgtctt ctgttattca caactgtttt aatttttatt tcattctgga      360
actcttcgag ttctttgtaa agtctttcat agtagcttac tttatcctcc aacatattta     420
acttcatgtc aatttcggct cttaaatttt ccacatcatc aagttcaaca tcatcttta      480 acttgaattt attctctagc tcttccaacc aagcctcatt gctccttgat ttactggtga     540
aaagtgatac actttgcgcg caatccaggt caaaactttc ctgcaaagaa ttcaccaatt     600
tctcgacatc atagtacaat ttgttttgtt ctcccatcac aatttaatat acctgatgga      660
ttcttatgaa gcgctgggta atggacgtgt cactctactt cgccttttc cctactcctt       720 ttagtacgga agacaatgct aataaataag agggtaataa taatattatt aatcggcaaa      780
aaagattaaa cgccaagcgt ttaattatca gaaagcaaac gtcgtaccaa tccttgaatg      840
cttcccaatt gtatattaag agtcatcaca gcaacatatt cttgttatta aattaattat     900
tattgatttt tgatattgta taaaaaaacc aaatatgtat aaaaaaagtg aataaaaaat      960
accaagtatg gagaaatata ttagaagtct atacgttaaa                           1000
```

<210> SEQ ID NO 58
<211> LENGTH: 1713
<212> TYPE: DNA
<213> ORGANISM: Streptococcus mutans

<400> SEQUENCE: 58

```
atgactgaca aaaaaactct taaagactta agaaatcgta gttctgttta cgattcaatg        60
gttaaatcac ctaatcgtgc tatgttgcgt gcaactggta tgcaagatga agactttgaa      120
aaacctatcg tcggtgtcat ttcaacttgg gctgaaaaca cccttgtaa tatccactta       180 catgactttg gtaaactagc caaagtcggt gttaaggaag ctggtgcttg gccagttcag      240
ttcggaacaa tcacggtttc tgatggaatc gccatgggaa cccaaggaat gcgtttctcc      300 ttgcatctc gtgatattat tgcagattct attgaagcag ccatgggagg tcataatgcg       360
gatgcttttg tagccattgg cggttgtgat aaaaacatgc ccggttctgt tatcgctatg      420
gctaacatgg atatcccagc catttttgct tacggcggaa caattgcacc tggtaattta      480
gacggcaaag atatcgattt agtctctgtc tttgaaggtg tcggccattg gaaccacggc      540
gatatgacca agaagaagt taaagctttg gaatgtaatg cttgtcccgg tcctggaggc      600
```

```
tgcggtggta tgtatactgc taacacaatg gcgacagcta ttgaagtttt gggacttagc    660
cttccgggtt catcttctca cccggctgaa tccgcagaaa agaaagcaga tattgaagaa    720
gctggtcgcg ctgttgtcaa aatgctcgaa atgggcttaa aaccttctga cattttaacg    780
cgtgaagctt ttgaagatgc tattactgta actatggctc tgggaggttc aaccaactca    840
acccttcacc tcttagctat tgcccatgct gctaatgtgg aattgacact tgatgatttc    900
aatactttcc aagaaaaagt tcctcatttg gctgatttga aaccttctgg tcaatatgta    960
ttccaagacc tttacaaggt cggaggggta ccagcagtta tgaaatatct ccttaaaaat   1020
ggcttccttc atggtgaccg tatcacttgt actggcaaaa cagtcgctga aaatttgaag   1080
gcttttgatg atttaacacc tggtcaaaag gttattatgc cgcttgaaaa tcctaaacgt   1140
gaagatggtc cgctcattat tctccatggt aacttggctc cagacggtgc cgttgccaaa   1200
gtttctggtg taaaagtgcg tcgtcatgtc ggtcctgcta aggtctttaa ttctgaagaa   1260
gaagccattg aagctgtctt gaatgatgat attgttgatg gtgatgttgt tgtcgtacgt   1320
tttgtaggac caaagggcgg tcctggtatg cctgaaatgc tttcccttcc atcaatgatt   1380
gttggtaaag gcaaggtga aaaagttgcc cttctgacag atggccgctt ctcaggtggt   1440
acttatggtc ttgtcgtggg tcatatcgct cctgaagcac aagatggcgg tccaatcgcc   1500
tacctgcaaa caggagacat agtcactatt gaccaagaca ctaaggaatt acactttgat   1560
atctccgatg aagagttaaa acatcgtcaa gagaccattg aattgccacc gctctattca   1620
cgcggtatcc ttggtaaata tgctcacatc gtttcgtctg cttctagggg agccgtaaca   1680 gactttttgga agcctgaaga aactggcaaa aaa                                1713
```

<210> SEQ ID NO 59
<211> LENGTH: 571
<212> TYPE: PRT
<213> ORGANISM: Streptococcus mutans

<400> SEQUENCE: 59

Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

```
Trp Asn His Gly Asp Met Thr Lys Glu Glu Val Lys Ala Leu Glu Cys
            180                 185                 190

Asn Ala Cys Pro Gly Pro Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570

<210> SEQ ID NO 60
<211> LENGTH: 2145
```

<212> TYPE: DNA
<213> ORGANISM: artificial sequence
<220> FEATURE:
<223> OTHER INFORMATION: constructed chimeric gene

<400> SEQUENCE: 60

| | | | | | |
|---|---|---|---|---|---|
| gcatgcttgc | atttagtcgt | gcaatgtatg | actttaagat | ttgtgagcag | gaagaaaagg | 60 |
| gagaatcttc | taacgataaa | cccttgaaaa | actgggtaga | ctacgctatg | ttgagttgct | 120 |
| acgcaggctg | cacaattaca | cgagaatgct | cccgcctagg | atttaaggct | aagggacgtg | 180 |
| caatgcagac | gacagatcta | aatgaccgtg | tcggtgaagt | gttcgccaaa | cttttcggtt | 240 |
| aacacatgca | gtgatgcacg | cgcgatggtg | ctaagttaca | tatatatata | tatatatata | 300 |
| tatagccata | gtgatgtcta | agtaacccttt | atggtatatt | tcttaatgtg | gaaagatact | 360 |
| agcgcgcgca | cccacacaca | agcttcgtct | tttcttgaag | aaaagaggaa | gctcgctaaa | 420 |
| tgggattcca | ctttccgttc | cctgccagct | gatggaaaaa | ggttagtgga | acgatgaaga | 480 |
| ataaaagag | agatccactg | aggtgaaatt | tcagctgaca | gcgagtttca | tgatcgtgat | 540 |
| gaacaatggt | aacgagttgt | ggctgttgcc | agggagggtg | gttctcaact | tttaatgtat | 600 |
| ggccaaatcg | ctacttgggt | ttgttatata | acaaagaaga | aataatgaac | tgattctctt | 660 |
| cctccttctt | gtcctttctt | aattctgttg | taattacctt | cctttgtaat | ttttttttgta | 720 |
| attattcttc | ttaataatcc | aaacaaacac | acatattaca | atagctagct | gaggatgaag | 780 |
| gcattagttt | atcatgggga | tcacaaaatt | tcgttagaag | acaaaccaaa | acccactctg | 840 |
| cagaaaccaa | cagacgttgt | ggttagggtg | ttgaaaacaa | caatttgcgg | tactgacttg | 900 |
| ggaatataca | aaggtaagaa | tcctgaagtg | gcagatggca | gaatcctggg | tcatgagggc | 960 |
| gttggcgtca | ttgaagaagt | gggcgaatcc | gtgacacaat | tcaaaaaggg | ggataaagtt | 1020 |
| ttaatctcct | gcgttactag | ctgtggatcg | tgtgattatt | gcaagaagca | actgtattca | 1080 |
| cactgtagag | acgtggctg | gatttttaggt | tacatgatcg | acggtgtcca | agccgaatac | 1140 |
| gtcagaatac | cacatgctga | caattcattg | tataagatcc | cgcaaactat | cgatgatgaa | 1200 |
| attgcagtac | tactgtccga | tattttacct | actggacatg | aaattggtgt | tcaatatggt | 1260 |
| aacgttcaac | caggcgatgc | tgtagcaatt | gtaggagcag | gtcctgttgg | aatgtcagtt | 1320 |
| ttgttaactg | ctcaatttta | ctcgcctagt | accattattg | ttatcgacat | ggacgaaaac | 1380 |
| cgtttacaat | tagcgaagga | gcttgggggcc | acacacacta | ttaactccgg | tactgaaaat | 1440 |
| gttgtcgaag | ctgtgcatcg | tatagcagcc | gaaggagtgg | atgtagcaat | agaagctgtt | 1500 |
| ggtatacccg | caacctggga | catctgtcag | gaaattgtaa | aacccggcgc | tcatattgcc | 1560 |
| aacgtgggag | ttcatggtgt | taaggtggac | tttgaaattc | aaaagttgtg | gattaagaat | 1620 |
| ctaaccatca | ccactggttt | ggttaacact | aatactaccc | caatgttgat | gaaggtagcc | 1680 |
| tctactgata | aattgccttt | aaagaaaatg | attactcaca | ggtttgagtt | agctgaaatc | 1740 |
| gaacacgcat | atcaggtttt | cttgaatggc | gctaaagaaa | aagctatgaa | gattattcta | 1800 |
| tctaatgcag | gtgccgccta | attaattaag | agtaagcgaa | tttcttatga | tttatgattt | 1860 |
| ttattattaa | ataagttata | aaaaaaataa | gtgtatacaa | attttaaagt | gactcttagg | 1920 |
| ttttaaaacg | aaaattctta | ttcttgagta | actctttcct | gtaggtcagg | ttgctttctc | 1980 |
| aggtatagca | tgaggtcgct | cttattgacc | acacctctac | cggcatgccg | agcaaatgcc | 2040 |
| tgcaaatcgc | tccccatttc | acccaattgt | agatatgcta | actccagcaa | tgagttgatg | 2100 |
| aatctcggtg | tgtattttat | gtcctcagag | gacaacacct | gtggt | | 2145 |

<210> SEQ ID NO 61
<211> LENGTH: 4280
<212> TYPE: DNA
<213> ORGANISM: artificial sequence
<220> FEATURE:
<223> OTHER INFORMATION: vector

<400> SEQUENCE: 61

```
ggggatcctc tagagtcgac ctgcaggcat gcaagcttgg cgtaatcatg gtcatagctg      60
tttcctgtgt gaaattgtta tccgctcaca attccacaca acatacgagc cggaagcata     120
aagtgtaaag cctggggtgc ctaatgagtg agctaactca cattaattgc gttgcgctca     180
ctgcccgctt tccagtcggg aaacctgtcg tgccagctgc attaatgaat cggccaacgc     240
gcggggagag gcggtttgcg tattgggcgc tcttccgctt cctcgctcac tgactcgctg     300
cgctcggtcg ttcggctgcg gcgagcggta tcagctcact caaaggcggt aatacggtta     360
tccacagaat caggggataa cgcaggaaag aacatgtgag caaaaggcca gcaaaaggcc     420
aggaaccgta aaaaggccgc gttgctggcg ttttccata ggctccgccc ccctgacgag     480
catcacaaaa atcgacgctc aagtcagagg tggcgaaacc cgacaggact ataaagatac     540
caggcgtttc ccctggaag ctccctcgtg cgctctcctg ttccgaccct gccgcttacc     600
ggatacctgt ccgcctttct cccttcggga agcgtggcgc tttctcatag ctcacgctgt     660
aggtatctca gttcggtgta ggtcgttcgc tccaagctgg gctgtgtgca cgaacccccc     720
gttcagcccg accgctgcgc cttatccggt aactatcgtc ttgagtccaa cccggtaaga     780
cacgacttat cgccactggc agcagccact ggtaacagga ttagcagagc gaggtatgta     840
ggcggtgcta cagagttctt gaagtggtgg cctaactacg gctacactag aaggacagta     900
tttggtatct gcgctctgct gaagccagtt accttcggaa aaagagttgg tagctcttga     960
tccggcaaac aaaccaccgc tggtagcggt ggtttttttg tttgcaagca gcagattacg    1020
cgcagaaaaa aaggatctca agaagatcct ttgatctttt ctacggggtc tgacgctcag    1080
tggaacgaaa actcacgtta agggattttg gtcatgagat tatcaaaaag gatcttcacc    1140
tagatccttt taaattaaaa atgaagtttt aaatcaatct aaagtatata tgagtaaact    1200
tggtctgaca gttaccaatg cttaatcagt gaggcaccta tctcagcgat ctgtctattt    1260
cgttcatcca tagttgcctg actccccgtc gtgtagataa ctacgatacg ggagggctta    1320
ccatctggcc ccagtgctgc aatgataccg cgagacccac gctcaccggc tccagattta    1380
tcagcaataa accagccagc cggaagggcc gagcgcagaa gtggtcctgc aactttatcc    1440
gcctccatcc agtctattaa ttgttgccgg gaagctagag taagtagttc gccagttaat    1500
agtttgcgca acgttgttgc cattgctaca ggcatcgtgg tgtcacgctc gtcgtttggt    1560
atggcttcat tcagctccgg ttcccaacga tcaaggcgag ttacatgatc ccccatgttg    1620
tgcaaaaaag cggttagctc cttcggtcct ccgatcgttg tcagaagtaa gttggccgca    1680
gtgttatcac tcatggttat ggcagcactg cataattctc ttactgtcat gccatccgta    1740
agatgctttt ctgtgactgg tgagtactca accaagtcat tctgagaata gtgtatgcgg    1800
cgaccgagtt gctcttgccc ggcgtcaata cgggataata ccgcgccaca tagcagaact    1860
ttaaaagtgc tcatcattgg aaaacgttct tcggggcgaa aactctcaag gatcttaccg    1920
ctgttgagat ccagttcgat gtaacccact cgtgcaccca actgatcttc agcatctttt    1980
actttcacca gcgtttctgg gtgagcaaaa acaggaaggc aaaatgccgc aaaaaaggga    2040
ataagggcga cacggaaatg ttgaatactc atactcttcc ttttcaata ttattgaagc    2100
```

```
atttatcagg gttattgtct catgagcgga tacatatttg aatgtattta gaaaaataaa   2160
caaatagggg ttccgcgcac atttccccga aaagtgccac ctgacgtcta agaaaccatt   2220
attatcatga cattaaccta taaaaatagg cgtatcacga ggccctttcg tctcgcgcgt   2280
ttcggtgatg acggtgaaaa cctctgacac atgcagctcc cggagacggt cacagcttgt   2340
ctgtaagcgg atgccgggag cagacaagcc cgtcagggcg cgtcagcggg tgttggcggg   2400
tgtcggggct ggcttaacta tgcggcatca gagcagattg tactgagagt gcaccatatg   2460
cggtgtgaaa taccgcacag atgcgtaagg agaaaatacc gcatcaggcg ccattcgcca   2520
ttcaggctgc gcaactgttg ggaagggcga tcggtgcggg cctcttcgct attacgccag   2580
ctggcgaaag ggggatgtgc tgcaaggcga ttaagttggg taacgccagg gttttcccag   2640
tcacgacgtt gtaaaacgac ggccagtgaa ttcgagctcg gtaccccggg ctctgagaca   2700
gtagtaggtt agtcatcgct ctaccgacgc gcaggaaaag aaagaagcat tgcggattac   2760
gtattctaat gttcagcccg cggaacgcca gcaaatcacc acccatgcgc atgatactga   2820
gtcttgtaca cgctgggctt ccagtgtact gagagtgcac cataccacag cttttcaatt   2880
caattcatca tttttttttt attcttttt ttgatttcgg tttctttgaa atttttttga   2940
ttcggtaatc tccgaacaga aggaagaacg aaggaaggag cacagactta gattggtata   3000
tatacgcata tgtagtgttg aagaaacatg aaattgccca gtattcttaa cccaactgca   3060
cagaacaaaa acctgcagga aacgaagata aatcatgtcg aaagctacat ataaggaacg   3120
tgctgctact catcctagtc ctgttgctgc caagctattt aatatcatgc acgaaaagca   3180
aacaaacttg tgtgcttcat tggatgttcg taccaccaag gaattactgg agttagttga   3240
agcattaggt cccaaaattt gtttactaaa acacatgtg gatatcttga ctgattttc   3300 catggagggc acagttaagc cgctaaaggc attatccgcc aagtacaatt ttttactctt   3360
cgaagacaga aaatttgctg acattggtaa tacagtcaaa ttgcagtact ctgcgggtgt   3420
atacagaata gcagaatggg cagacattac gaatgcacac ggtgtggtgg gcccaggtat   3480 tgttagcgg ttgaagcagg cggcagaaga agtaacaaag gaacctagag gcctttgat    3540 gttagcagaa ttgtcatgca agggctccct atctactgga gaatatacta agggtactgt   3600
tgacattgcg aagagcgaca aagatttgt tatcggcttt attgctcaaa gagacatggg    3660
tggaagagat gaaggttacg attggttgat tatgacaccc ggtgtgggtt tagatgacaa   3720
gggagacgca ttgggtcaac agtatagaac cgtggatgat gtggtctcta caggatctga   3780
cattattatt gttggaagag gactatttgc aaagggaagg gatgctaagg tagagggtga   3840
acgttacaga aaagcaggct gggaagcata tttgagaaga tgcggccagc aaaactaaaa   3900
aactgtatta taagtaaatg catgtatact aaactcacaa attagagctt caatttaatt   3960
atatcagtta ttaccctatg cggtgtgaaa taccgcacag atgcgtaagg agaaaatacc   4020
gcatcaggaa attgtaaacg ttaatatttt gttaaaattc gcgttaaatt tttgttaaat   4080
cagctcattt tttaaccaat aggccgaaat cggcaaaatc ttcagcccgc ggaacgccag   4140
caaatcacca cccatgcgca tgatactgag tcttgtacac gctgggcttc cagtgatgat   4200
acaacgagtt agccaaggtg agcacggatg tctaaattag aattacgttt taatatcttt   4260
ttttccatat ctagggctag                                               4280
```

<210> SEQ ID NO 62
<211> LENGTH: 30
<212> TYPE: DNA

<213> ORGANISM: artificial sequence
<220> FEATURE:
<223> OTHER INFORMATION: primer

<400> SEQUENCE: 62
gcatgcttgc atttagtcgt gcaatgtatg                              30

<210> SEQ ID NO 63
<211> LENGTH: 54
<212> TYPE: DNA
<213> ORGANISM: artificial sequence
<220> FEATURE:
<223> OTHER INFORMATION: primer

<400> SEQUENCE: 63
gaacattaga atacgtaatc cgcaatgcac tagtaccaca ggtgttgtcc tctg    54

<210> SEQ ID NO 64
<211> LENGTH: 54
<212> TYPE: DNA
<213> ORGANISM: artificial sequence
<220> FEATURE:
<223> OTHER INFORMATION: primer

<400> SEQUENCE: 64
cagaggacaa cacctgtggt actagtgcat tgcggattac gtattctaat gttc    54

<210> SEQ ID NO 65
<211> LENGTH: 28
<212> TYPE: DNA
<213> ORGANISM: artificial sequence
<220> FEATURE:
<223> OTHER INFORMATION: primer

<400> SEQUENCE: 65
caccttggct aactcgttgt atcatcac                                28

<210> SEQ ID NO 66
<211> LENGTH: 100
<212> TYPE: DNA
<213> ORGANISM: artificial sequence
<220> FEATURE:
<223> OTHER INFORMATION: primer

<400> SEQUENCE: 66
ttttaagccg aatgagtgac agaaaaagcc cacaacttat caagtgatat tgaacaaagg    60
gcgaaacttc gcatgcttgc atttagtcgt gcaatgtatg                         100

<210> SEQ ID NO 67
<211> LENGTH: 98
<212> TYPE: DNA
<213> ORGANISM: artificial sequence
<220> FEATURE:
<223> OTHER INFORMATION: primer

<400> SEQUENCE: 67
cccaattggt aaatattcaa caagagacgc gcagtacgta acatgcgaat tgcgtaattc    60
acggcgataa caccttggct aactcgttgt atcatcac                           98

<210> SEQ ID NO 68
<211> LENGTH: 29
<212> TYPE: DNA
<213> ORGANISM: artificial sequence
<220> FEATURE:
<223> OTHER INFORMATION: primer

<400> SEQUENCE: 68
caaaagccca tgtcccacac caaaggatg                                           29

<210> SEQ ID NO 69
<211> LENGTH: 26
<212> TYPE: DNA
<213> ORGANISM: artificial sequence
<220> FEATURE:
<223> OTHER INFORMATION: primer

<400> SEQUENCE: 69
caccatcgcg cgtgcatcac tgcatg                                              26

<210> SEQ ID NO 70
<211> LENGTH: 28
<212> TYPE: DNA
<213> ORGANISM: artificial sequence
<220> FEATURE:
<223> OTHER INFORMATION: primer

<400> SEQUENCE: 70
tcggtttttg caatatgacc tgtgggcc                                            28

<210> SEQ ID NO 71
<211> LENGTH: 22
<212> TYPE: DNA
<213> ORGANISM: artificial sequence
<220> FEATURE:
<223> OTHER INFORMATION: primer

<400> SEQUENCE: 71
gagaagatgc ggccagcaaa ac                                                  22

<210> SEQ ID NO 72
<211> LENGTH: 2745
<212> TYPE: DNA
<213> ORGANISM: artificial sequence
<220> FEATURE:
<223> OTHER INFORMATION: constructed coding region-terminator segment

<400> SEQUENCE: 72
atgactgaca aaaaaactct taaagactta agaaatcgta gttctgttta cgattcaatg      60
gttaaatcac ctaatcgtgc tatgttgcgt gcaactggta tgcaagatga agactttgaa     120
aaacctatcg tcggtgtcat ttcaacttgg gctgaaaaca caccttgtaa tatccactta     180
catgactttg taaactagc caaagtcggt gttaaggaag ctggtgcttg gccagttcag      240
ttcggaacaa tcacggtttc tgatggaatc gccatgggaa cccaaggaat gcgtttctcc     300
ttgacatctc gtgatattat tgcagattct attgaagcag ccatgggagg tcataatgcg     360
gatgcttttg tagccattgg cggttgtgat aaaaacatgc ccggttctgt tatcgctatg     420
gctaacatgg atatcccagc cattttttgct tacgcggaa caattgcacc tggtaattta    480
gacggcaaag atatcgattt agtctctgtc tttgaaggtg tcggccattg gaaccacggc     540
gatatgacca agaagaagt taaagctttg gaatgtaatg cttgtcccgg tcctggaggc     600
tgcggtggta tgtatactgc taacacaatg gcgacagcta ttgaagtttt gggacttagc     660
cttccgggtt catcttctca cccggctgaa tccgcagaaa agaaagcaga tattgaagaa     720
gctggtcgcg ctgttgtcaa aatgctcgaa atgggcttaa aaccttctga cattttaacg     780
cgtgaagctt ttgaagatgc tattactgta actatggctc tgggaggttc aaccaactca    840

```
acccttcacc tcttagctat tgcccatgct gctaatgtgg aattgacact tgatgatttc      900
aatactttcc aagaaaaagt tcctcatttg gctgatttga aaccttctgg tcaatatgta      960
ttccaagacc tttacaaggt cggaggggta ccagcagtta tgaaatatct ccttaaaaat     1020
ggcttccttc atggtgaccg tatcacttgt actggcaaaa cagtcgctga aaatttgaag     1080
gcttttgatg atttaacacc tggtcaaaag gttattatgc cgcttgaaaa tcctaaacgt     1140
gaagatggtc cgctcattat tctccatggt aacttggctc cagacggtgc cgttgccaaa     1200
gtttctggtg taaaagtgcg tcgtcatgtc ggtcctgcta aggtctttaa ttctgaagaa     1260
gaagccattg aagctgtctt gaatgatgat attgttgatg gtgatgttgt tgtcgtacgt     1320
tttgtaggac caagggcgg tcctggtatg cctgaaatgc tttcccttc atcaatgatt      1380 gttggtaaag gcaaggtga aaagttgcc cttctgacag atggccgctt ctcaggtggt      1440
acttatggtc ttgtcgtggg tcatatcgct cctgaagcac aagatggcgg tccaatcgcc     1500
tacctgcaaa caggagacat agtcactatt gaccaagaca ctaaggaatt acactttgat     1560
atctccgatg aagagttaaa acatcgtcaa gagaccattg aattgccacc gctctattca     1620
cgcggtatcc ttggtaaata tgctcacatc gtttcgtctg cttctagggg agccgtaaca     1680
gacttttgga agcctgaaga aactggcaaa aaatgttgtc ctggttgctg tggttaagcg     1740
gccgcgttaa ttcaaattaa ttgatatagt tttttaatga gtattgaatc tgtttagaaa     1800
taatggaata ttatttttat ttatttattt atattattgg tcggctcttt tcttctgaag     1860
gtcaatgaca aaatgatatg aaggaaataa tgatttctaa aattttacaa cgtaagatat     1920
ttttacaaaa gcctagctca tcttttgtca tgcactattt tactcacgct tgaaattaac     1980
ggccagtcca ctgcggagtc atttcaaagt catcctaatc gatctatcgt ttttgatagc     2040
tcattttgga gttcgcgatt gtcttctgtt attcacaact gttttaattt ttatttcatt     2100
ctggaactct tcgagttctt tgtaaagtct ttcatagtag cttactttat cctccaacat     2160
atttaacttc atgtcaattt cggctcttaa attttccaca tcatcaagtt caacatcatc     2220
ttttaacttg aatttattct ctagctcttc caaccaagcc tcattgctcc ttgatttact     2280
ggtgaaaagt gatacacttt gcgcgcaatc caggtcaaaa ctttcctgca agaattcac     2340 caatttctcg acatcatagt acaatttgtt ttgttctccc atcacaattt aatataccctg    2400 atggattctt atgaagcgct gggtaatgga cgtgtcactc tacttcgcct ttttccctac     2460 tcctttagt acggaagaca atgctaataa ataagagggt aataataata ttattaatcg      2520
gcaaaaaaga ttaaacgcca agcgtttaat tatcagaaag caaacgtcgt accaatcctt     2580
gaatgcttcc caattgtata ttaagagtca tcacagcaac atattcttgt tattaaatta     2640
attattattg atttttgata ttgtataaaa aaaccaaata tgtataaaaa aagtgaataa     2700
aaaataccaa gtatggagaa atatattaga agtctatacg ttaaa                    2745
```

<210> SEQ ID NO 73  
<211> LENGTH: 99  
<212> TYPE: DNA  
<213> ORGANISM: artificial sequence  
<220> FEATURE:  
<223> OTHER INFORMATION: primer

<400> SEQUENCE: 73

```
tcctttctca attattattt tctactcata acctcacgca aaataacaca gtcaaatcaa       60
tcaaagtatg actgacaaaa aaactcttaa agacttaag                              99
```

-continued

<210> SEQ ID NO 74
<211> LENGTH: 77
<212> TYPE: DNA
<213> ORGANISM: artificial sequence
<220> FEATURE:
<223> OTHER INFORMATION: primer

<400> SEQUENCE: 74
gaacattaga atacgtaatc cgcaatgctt ctttcttttc cgtttaacgt atagacttct    60
aatatatttc tccatac                                                   77

<210> SEQ ID NO 75
<211> LENGTH: 45
<212> TYPE: DNA
<213> ORGANISM: artificial sequence
<220> FEATURE:
<223> OTHER INFORMATION: primer

<400> SEQUENCE: 75
aaacggaaaa gaaagaagca ttgcggatta cgtattctaa tgttc                    45

<210> SEQ ID NO 76
<211> LENGTH: 88
<212> TYPE: DNA
<213> ORGANISM: artificial sequence
<220> FEATURE:
<223> OTHER INFORMATION: primer

<400> SEQUENCE: 76
tatttttcgt tacataaaaa tgcttataaa actttaacta ataattagag attaaatcgc    60
caccttggct aactcgttgt atcatcac                                       88

<210> SEQ ID NO 77
<211> LENGTH: 27
<212> TYPE: DNA
<213> ORGANISM: artificial sequence
<220> FEATURE:
<223> OTHER INFORMATION: primer

<400> SEQUENCE: 77 gactttgga agcctgaaga aactggc                                         27

<210> SEQ ID NO 78
<211> LENGTH: 20
<212> TYPE: DNA
<213> ORGANISM: artificial sequence
<220> FEATURE:
<223> OTHER INFORMATION: primer

<400> SEQUENCE: 78
cttggcagca acaggactag                                                20

<210> SEQ ID NO 79
<211> LENGTH: 26
<212> TYPE: DNA
<213> ORGANISM: artificial sequence
<220> FEATURE:
<223> OTHER INFORMATION: primer

<400> SEQUENCE: 79
ccaggccaat tcaacagact gtcggc                                         26

<210> SEQ ID NO 80
<211> LENGTH: 26
<212> TYPE: DNA

```
<213> ORGANISM: artificial sequence
<220> FEATURE:
<223> OTHER INFORMATION: primer

<400> SEQUENCE: 80
gacttgaata atgcagcggc gcttgc                                          26

<210> SEQ ID NO 81
<211> LENGTH: 30
<212> TYPE: DNA
<213> ORGANISM: artificial sequence
<220> FEATURE:
<223> OTHER INFORMATION: primer

<400> SEQUENCE: 81
ccaccctctt caattagcta agatcatagc                                      30

<210> SEQ ID NO 82
<211> LENGTH: 25
<212> TYPE: DNA
<213> ORGANISM: artificial sequence
<220> FEATURE:
<223> OTHER INFORMATION: primer

<400> SEQUENCE: 82
aaaaattgat tctcatcgta aatgc                                           25

<210> SEQ ID NO 83
<211> LENGTH: 20
<212> TYPE: DNA
<213> ORGANISM: artificial sequence
<220> FEATURE:
<223> OTHER INFORMATION: primer

<400> SEQUENCE: 83
ctgcagcgag gagccgtaat                                                 20

<210> SEQ ID NO 84
<211> LENGTH: 2347
<212> TYPE: DNA
<213> ORGANISM: artificial sequence
<220> FEATURE:
<223> OTHER INFORMATION: constructed URA3 marker with flanking
      homologous repeat sequences for HIS gene replacement and marker
      excision

<400> SEQUENCE: 84
gcattgcgga ttacgtattc taatgttcag gtgctggaag aagagctgct taaccgccgc     60
gcccagggtg aagatccacg ctactttacc ctgcgtcgtc tggatttcgg cggctgtcgt    120
ctttcgctgg caacgccggt tgatgaagcc tgggacggtc cgctctcctt aaacggtaaa    180
cgtatcgcca cctcttatcc tcacctgctc aagcgttatc tcgaccagaa aggcatctct    240
tttaaatcct gcttactgaa cggttctgtt gaagtcgccc cgcgtgccgg actggcggat    300
gcgatttgcg atctggtttc caccggtgcc acgctggaag ctaacggcct gcgcgaagtc    360
gaagttatct atcgctcgaa agcctgcctg attcaacgcg atggcgaaat ggaagaatcc    420
aaacagcaac tgatcgacaa actgctgacc cgtattcagg gtgtgatcca ggcgcgcgaa    480
tcaaaataca tcatgatgca cgcaccgacc gaacgtctgg atgaagtcat ggtacctact    540
gagagtgcac ataccacag cttttcaatt caattcatca ttttttttt attctttttt     600 ttgatttcgg tttctttgaa attttttga ttcggtaatc tccgaacaga aggaagaacg    660
aaggaaggag cacagactta gattggtata tatacgcata tgtagtgttg aagaaacatg    720
```

```
aaattgccca gtattcttaa cccaactgca cagaacaaaa acctgcagga aacgaagata    780
aatcatgtcg aaagctacat ataaggaacg tgctgctact catcctagtc ctgttgctgc    840
caagctattt aatatcatgc acgaaaagca aacaaacttg tgtgcttcat tggatgttcg    900
taccaccaag gaattactgg agttagttga agcattaggc cccaaaattt gtttactaaa    960
aacacatgtg gatatcttga ctgattttc catggagggc acagttaagc cgctaaaggc   1020
attatccgcc aagtacaatt ttttactctt cgaagacaga aaatttgctg acattggtaa   1080
tacagtcaaa ttgcagtact ctgcgggtgt atacagaata gcagaatggg cagacattac   1140
gaatgcacac ggtgtggtgg gcccaggtat tgttagcggt ttgaagcagg cggcagaaga   1200
agtaacaaag gaacctagag gccttttgat gttagcagaa ttgtcatgca agggctccct   1260
atctactgga gaatatacta agggtactgt tgacattgcg aagagcgaca agattttgt    1320 tatcggcttt attgctcaaa gagacatggg tggaagagat gaaggttacg attggttgat   1380
tatgacaccc ggtgtgggtt tagatgacaa gggagacgca ttgggtcaac agtatagaac   1440
cgtggatgat gtggtctcta caggatctga cattattatt gttggaagag gactatttgc   1500
aaagggaagg gatgctaagg tagagggtga acgttacaga aaagcaggct gggaagcata   1560
tttgagaaga tgcggccagc aaaactaaaa aactgtatta taagtaaatg catgtatact   1620
aaactcacaa attagagctt caatttaatt atatcagtta ttaccctatg cggtgtgaaa   1680
taccgcacag atgcgtaagg agaaaatacc gcatcaggaa attgtaaacg ttaatatttt   1740
gttaaaattc gcgttaaatt tttgttaaat cagctcattt tttaaccaat aggccgaaat   1800
cggcaaaatc tctagagtgc tggaagaaga gctgcttaac cgccgcgccc agggtgaaga   1860
tccacgctac tttaccctgc gtcgtctgga tttcggcggc tgtcgtcttt cgctggcaac   1920
gccggttgat gaagcctggg acggtccgct ctccttaaac ggtaaacgta tcgccacctc   1980
ttatcctcac ctgctcaagc gttatctcga ccagaaaggc atctctttta aatcctgctt   2040
actgaacggt tctgttgaag tcgccccgcg tgccggactg gcggatgcga tttgcgatct   2100
ggtttccacc ggtgccacgc tggaagctaa cggcctgcgc gaagtcgaag ttatctatcg   2160
ctcgaaagcc tgcctgattc aacgcgatgg cgaaatggaa gaatccaaac agcaactgat   2220
cgacaaactg ctgacccgta ttcagggtgt gatccaggcg cgcgaatcaa aatacatcat   2280
gatgcacgca ccgaccgaac gtctggatga agtcatccag tgatgataca acgagttagc   2340
caaggtg                                                             2347
```

<210> SEQ ID NO 85
<211> LENGTH: 80
<212> TYPE: DNA
<213> ORGANISM: artificial sequence
<220> FEATURE:
<223> OTHER INFORMATION: primer

<400> SEQUENCE: 85

```
cttcgaagaa tatactaaaa aatgagcagg caagataaac gaaggcaaag gcattgcgga     60
ttacgtattc taatgttcag                                                 80
```

<210> SEQ ID NO 86
<211> LENGTH: 80
<212> TYPE: DNA
<213> ORGANISM: artificial sequence
<220> FEATURE:
<223> OTHER INFORMATION: primer

```
<400> SEQUENCE: 86
cttcgaagaa tatactaaaa aatgagcagg caagataaac gaaggcaaag gcattgcgga        60
ttacgtattc taatgttcag                                                    80
```

METHOD FOR PRODUCING BUTANOL USING TWO-PHASE EXTRACTIVE FERMENTATION

This application is a continuation-in-part of U.S. application Ser. No. 12/478,389, filed Jun. 4, 2009, herein incorporated by reference, and which claims the benefit of priority from U.S. Provisional Application No. 61/058,567, filed Jun. 4, 2008, herein incorporated by reference.

FIELD OF THE INVENTION

The invention relates to the field of biofuels. More specifically, the invention relates to a method for producing butanol through microbial fermentation, in which the butanol product is removed by extraction into a water immiscible organic extractant during the fermentation.

BACKGROUND OF THE INVENTION

Butanol is an important industrial chemical, with a variety of applications, such as use as a fuel additive, as a feedstock chemical in the plastics industry, and as a foodgrade extractant in the food and flavor industry. Each year 10 to 12 billion pounds of butanol are produced by petrochemical means and the need for this chemical will likely increase.

Several chemical synthetic methods are known; however, these methods of producing butanol use starting materials derived from petrochemicals and are generally expensive and are not environmentally friendly. Several methods of producing butanol by fermentation are also known, for example the ABE process which is the fermentive process producing a mixture of acetone, 1-butanol and ethanol. Acetone-butanol-ethanol (ABE) fermentation by *Clostridium acetobutylicum* is one of the oldest known industrial fermentations; as is also the pathways and genes responsible for the production of these solvents. Production of 1-butanol by the ABE process is limited by the toxic effect of the 1-butanol on *Clostridium acetobutylicum*. In situ extractive fermentation methods using specific organic extractants which are nontoxic to the bacterium have been reported to enhance the production of 1-butanol by fermentation using *Clostridium acetobutylicum* (Roffler et al., *Biotechnol. Bioeng.* 31:135-143, 1988; Roffler et al., *Bioprocess Engineering* 2:1-12, 1987; and Evans et al., *Appl. Environ. Microbiol.* 54:1662-1667, 1988).

In contrast to the native *Clostridium acetobutylicum* described above, recombinant microbial production hosts expressing 1-butanol, 2-butanol, and isobutanol biosynthetic pathways have also been described. These recombinant hosts have the potential of producing butanol in higher yields compared to the ABE process because they do not produce byproducts such as acetone and ethanol. However, the problem with these recombinant hosts is that biological production of butanol appears to be limited by butanol toxicity thresholds to the host microorganism used in the fermentation. Extractive fermentation methods have not been applied to the production of butanols using recombinant microbial strains.

The present invention satisfies the above need and provides a method of making butanol from at least one fermentable carbon source that overcome the issues of toxicity resulting in an increase in the effective titer, the effective rate, and the effective yield of butanol production by fermentation utilizing a recombinant microbial host wherein the butanol is extracted into specific organic extractants during fermentation.

SUMMARY OF THE INVENTION

The invention provides a method for recovering butanol from a fermentation medium, the method comprising:
a) providing a fermentation medium comprising butanol, water, and a genetically modified microorganism that produces butanol from at least one fermentable carbon source;
b) contacting the fermentation medium with i) at least one first water immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof, and optionally (ii) a second water immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof to form a two-phase mixture comprising an aqueous phase and a butanol-containing organic phase;
c) separating the butanol-containing organic phase from the aqueous phase; and
d) recovering the butanol from the butanol-containing organic phase to produce recovered butanol.

The invention provides a method for the production of butanol comprising the steps of:
a) providing a genetically modified microorganism that produces butanol from at least one fermentable carbon source;
b) growing the microorganism in a biphasic fermentation medium comprising an aqueous phase and a water immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof, wherein said biphasic fermentation medium comprises from about 3% to about 60% by volume of said water immiscible organic extractant, for a time sufficient to allow extraction of the butanol into the organic extractant to form a butanol-containing organic phase;
c) separating the butanol-containing organic phase from the aqueous phase; and
d) recovering the butanol from the butanol-containing organic phase to produce recovered butanol.

An embodiment of the invention provides a method for the production of butanol comprising the steps of:
a) providing a genetically modified microorganism that produces butanol from at least one fermentable carbon source;
b) growing the microorganism in a fermentation medium wherein the microorganism produces said butanol into the fermentation medium to produce a butanol-containing fermentation medium;
c) contacting the butanol-containing fermentation medium with i) at least one first water immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof, and optionally (ii) a second water immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof to form a two-phase mixture comprising an aqueous phase and a butanol-containing organic phase;
d) separating the butanol-containing organic phase from the aqueous phase; and e) recovering the butanol from the butanol-containing organic phase.

An embodiment of the invention provides a method for the production of butanol comprising the steps of:
a) providing a genetically modified microorganism that produces butanol from at least one fermentable carbon source;
b) growing the microorganism in a fermentation medium under aerobic conditions for a time sufficient to reach a preselected growth level;
c) switching to microaerobic or anaerobic conditions to stimulate butanol production into the fermentation medium to form a butanol-containing fermentation medium;
d) contacting the butanol-containing fermentation medium with i) at least one first water immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof, and optionally (ii) a second water immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof to form a two-phase mixture comprising an aqueous phase and a butanol-containing organic phase;
e) separating the butanol-containing organic phase from the aqueous phase; and
f) recovering the butanol from the butanol-containing organic phase.

Another embodiment of the invention provides a method for the production of butanol comprising the steps of:
a) providing a fermentation medium comprising butanol, water, and a genetically modified microorganism that produces butanol from a fermentation medium comprising at least one fermentable carbon source;
b) contacting the fermentation medium via a co-current or counter-current extractant stream with i) at least one first water immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof, and optionally (ii) a second water immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof to form a two-phase mixture comprising an aqueous phase and a butanol-containing organic phase;
c) separating the butanol-containing organic phase from the aqueous phase; and
d) recovering the butanol from the butanol-containing organic phase to produce recovered butanol.

The present extractive fermentation methods provide butanol, including all butanol isomers, which is known to have an energy content similar to that of gasoline and which can be blended with any fossil fuel. Butanol is favored as a fuel or fuel additive as it yields only $CO_2$ and little or no $SO_X$ or $NO_X$ when burned in the standard internal combustion engine. Additionally butanol is less corrosive than ethanol, the most preferred fuel additive to date.

In addition to its utility as a biofuel or fuel additive, the butanol produced from the present methods has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or vehicles.

Finally, the present methods produce butanol from plant derived carbon sources, avoiding the negative environmental impact associated with standard petrochemical processes for butanol production.

BRIEF DESCRIPTION OF THE FIGURE AND SEQUENCE DESCRIPTIONS

FIG. 1 is a graph showing the concentration of isobutanol in the fermentation medium (i.e., aqueous phase) during a fermentation using oleyl alcohol as the organic extractant with gas stripping (■) as described in Example 6, and during a fermentation with gas stripping alone (●), as described in Example 7. FIG. 1 represents data generated using a recombinant *Escherichia coli* producing isobutanol.

Figure 2:
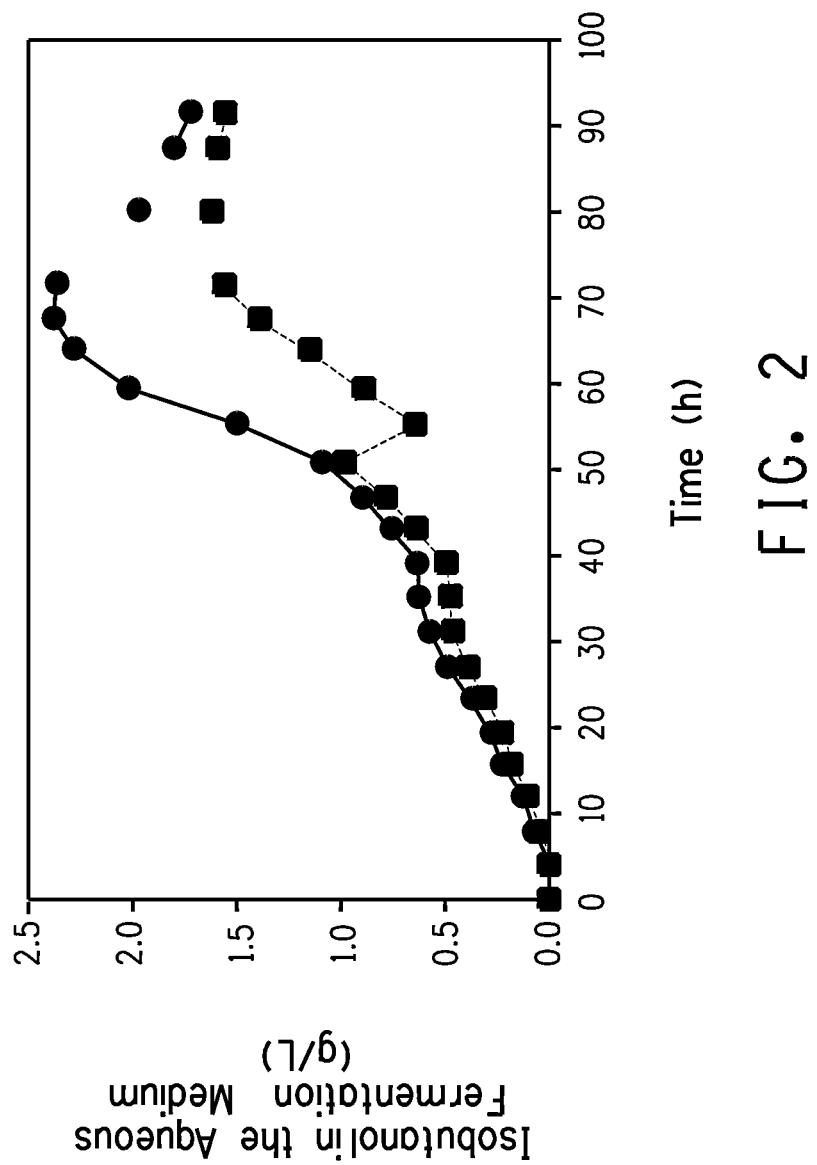

FIG. 2 is a graph showing the concentration of isobutanol in the fermentation medium (i.e., aqueous phase) during a fermentation using oleyl alcohol as the organic extractant with gas stripping (■) as described in Example 8, and during a fermentation with gas stripping alone (●), as described in Example 9. FIG. 2 represents data generated using a recombinant *Saccharomyces cerevisiae* producing isobutanol.

Figure 3:
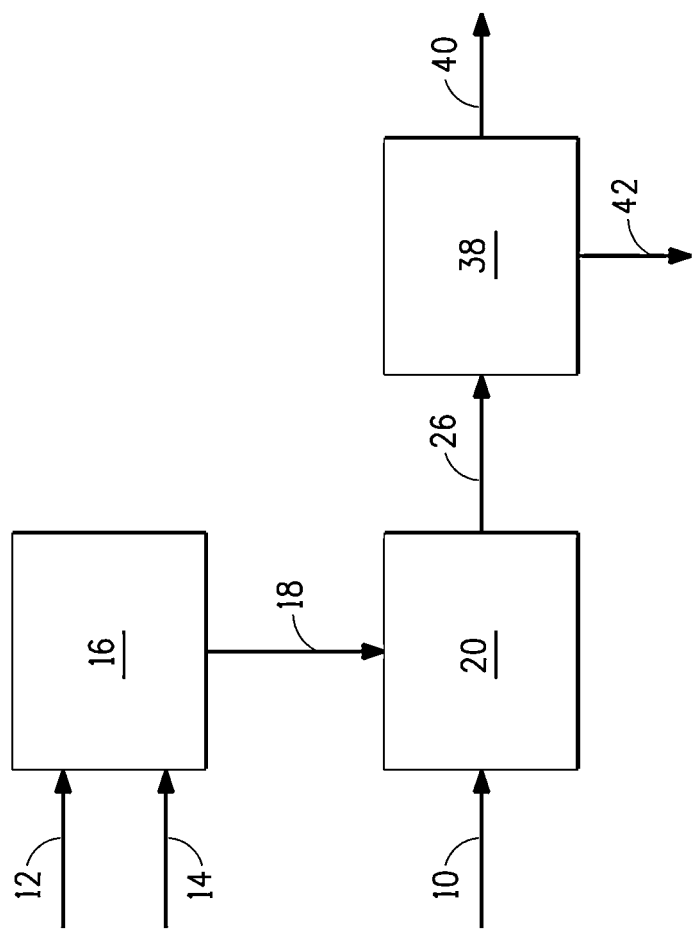

FIG. 3 schematically illustrates one embodiment of the methods of the invention, in which the first water immiscible extractant and the optional second water immiscible extractant are combined in a vessel prior to contacting the fermentation medium with the extractant in a fermentation vessel.

Figure 4:
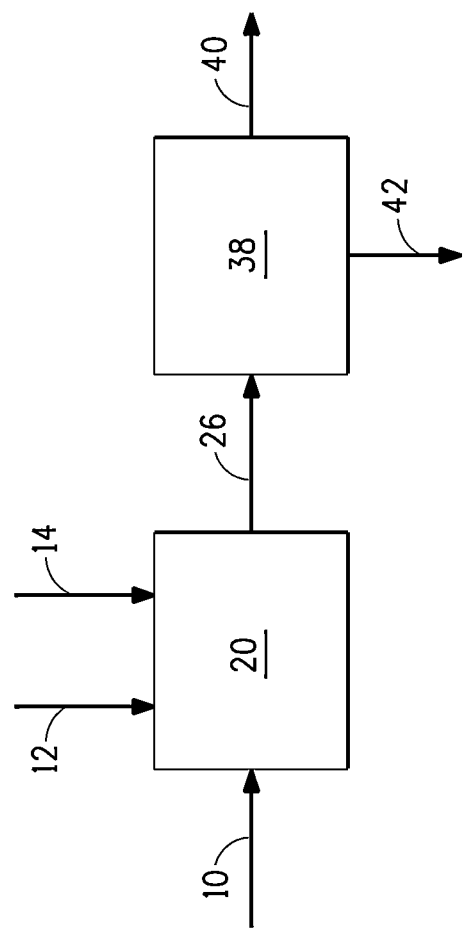

FIG. 4 schematically illustrates one embodiment of the methods of the invention, in which the first water immiscible extractant and the optional second water immiscible extractant are added separately to a fermentation vessel in which the fermentation medium is contacted with the extractant.

Figure 5:
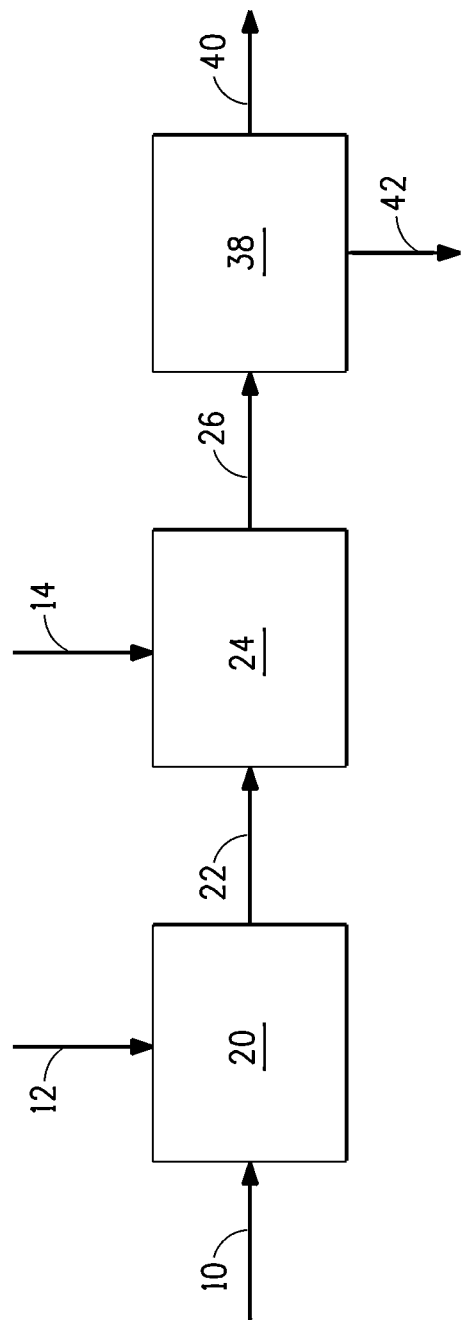

FIG. 5 schematically illustrates one embodiment of the methods of the invention, in which the first water immiscible extractant and the optional second water immiscible extractant are added separately to different fermentation vessels for contacting of the fermentation medium with the extractant.

Figure 6:
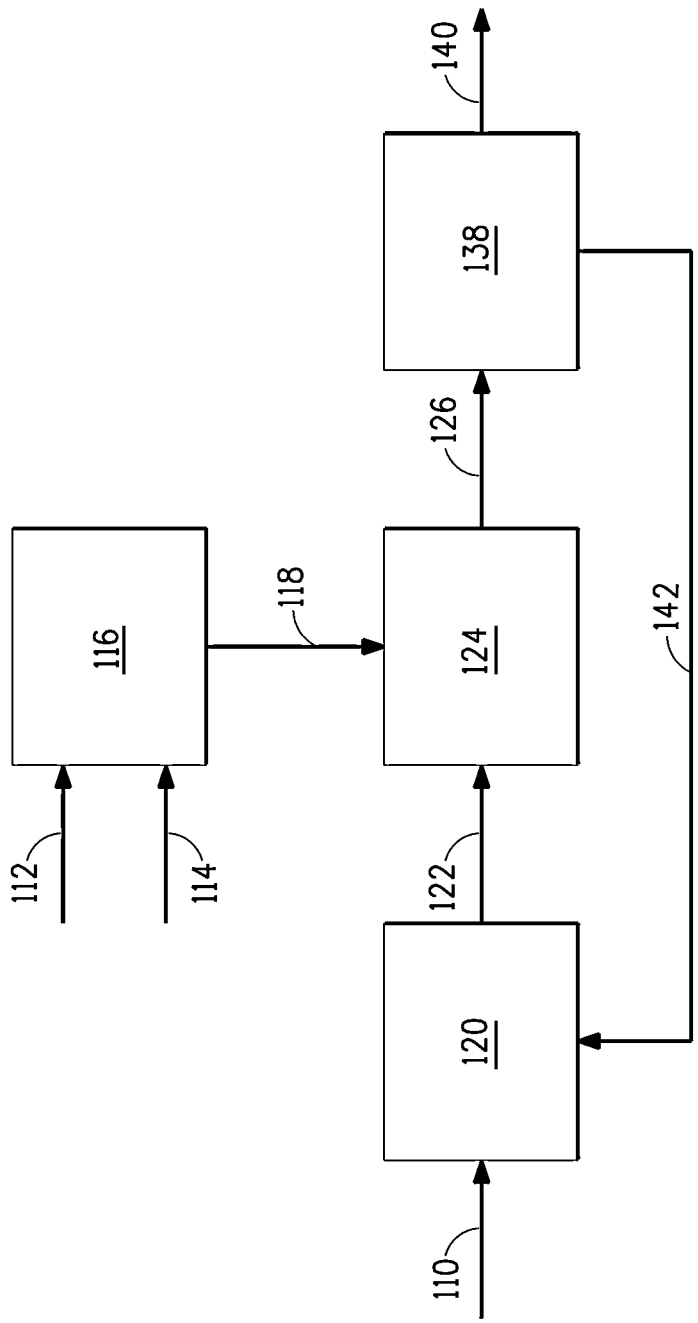

FIG. 6 schematically illustrates one embodiment of the methods of the invention, in which extraction of the product occurs downstream of the fermentor and the first water immiscible extractant and the optional second water immiscible extractant are combined in a vessel prior to contacting the fermentation medium with the extractant in a different vessel.

Figure 7:
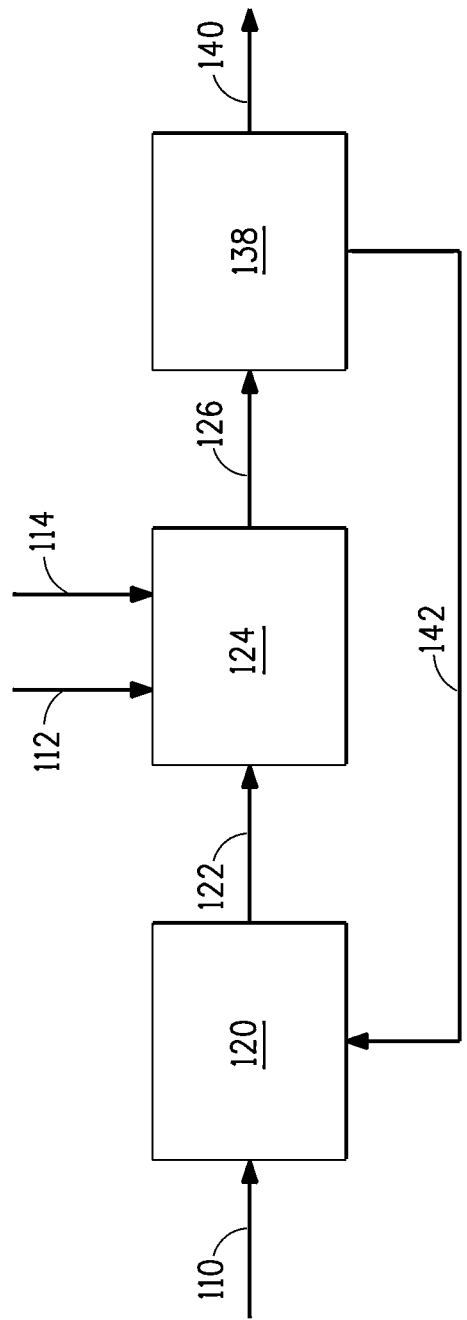

FIG. 7 schematically illustrates one embodiment of the methods of the invention, in which extraction of the product occurs downstream of the fermentor and the first water immiscible extractant and the optional second water immiscible extractant are added separately to a vessel in which the fermentation medium is contacted with the extractant.

Figure 8:
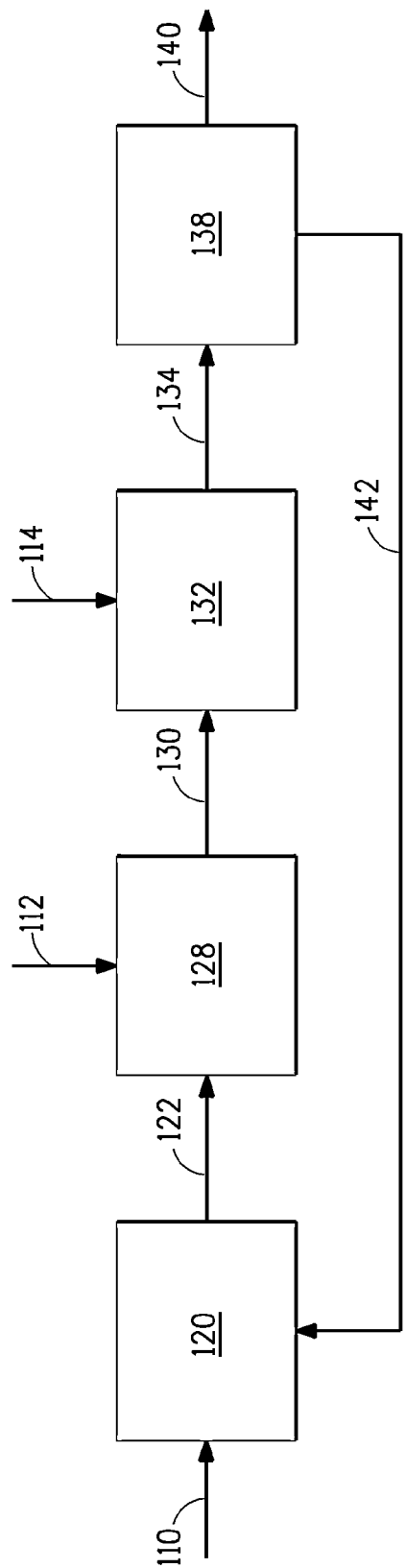

FIG. 8 schematically illustrates one embodiment of the methods of the invention, in which extraction of the product occurs downstream of the fermentor and the first water immiscible extractant and the optional second water immiscible extractant are added separately to different vessels for contacting of the fermentation medium with the extractant.

FIG. 9 schematically illustrates one embodiment of the methods of the invention, in which extraction of the product occurs in at least one batch fermentor via co-current flow of an extractant at or near the bottom of a fermentation mash to fill the fermentor with extractant which flows out of the fermentor at a point at or near the top of the fermentor.

The following sequences conform with 37 C.F.R. 1.821 1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a bis), and Section 208 and Annex C of the Administrative Instructions).

TABLE 1

Summary of Gene and Protein SEQ ID Numbers

| Description | SEQ ID NO: Nucleic acid | SEQ ID NO: Peptide |
|---|---|---|
| *Klebsiella pneumoniae* budB (acetolactate synthase) | 1 | 2 |
| *E. coli* ilvC (acetohydroxy acid reductoisomerase) | 3 | 4 |
| *E. coli* ilvD (acetohydroxy acid dehydratase) | 5 | 6 |
| *Lactococcus lactis* kivD (branched-chain α-keto acid decarboxylase), codon optimized | 7 | 8 |
| *Achromobacter xylosoxidans*. butanol dehydrogenase (sadB) gene | 9 | 10 |
| *Bacillus subtilis* alsS (acetolactate synthase) | 32 | 33 |
| Pf5.IlvC-Z4B8 (KARI) | 36 | 37 |
| *S. cerevisiae* ILV5 (acetohydroxy acid reductoisomerase; KARI) | 40 | 41 |
| *B. subtilis* ketoisovalerate decarboxylase (KivD) codon optimized | 43 | 44 |
| Horse liver alcohol dehydrogenase (HADH) codon optimized | 45 | 46 |
| *Streptococcus mutans* ilvD acetohydroxy acid dehydratase | 58 | 59 |

SEQ ID NOs:11-22 are the nucleotide sequences of the primers used to construct the recombinant *Escherichia coli* strain described in the General Methods section of the Examples herein below.

SEQ ID NO:23 is the nucleotide sequence of the pflB gene from *Escherichia coli* strain K-12 MG1655.

SEQ ID NO:24 is the nucleotide sequence of the ldhA gene from *Escherichia coli* strain K-12 MG1655.

SEQ ID NO:25 is the nucleotide sequence of the adhE gene from *Escherichia coli* strain K-12 MG1655.

SEQ ID NO:26 is the nucleotide sequence of the frdA gene from *Escherichia coli* strain K-12 MG1655.

SEQ ID NO:27 is the nucleotide sequence of the frdB gene from *Escherichia coli* strain K-12 MG1655.

SEQ ID NO:28 is the nucleotide sequence of the frdC gene from *Escherichia coli* strain K-12 MG1655.

SEQ ID NO:29 is the nucleotide sequence of the frdD gene from *Escherichia coli* strain K-12 MG1655.

SEQ ID NO; 30 is the nucleotide sequence of pLH475-Z4B8.

SEQ ID NO; 31 is the nucleotide sequence of the CUP1 promoter.

SEQ ID NO; 34 is the nucleotide sequence of the CYC1 terminator.

SEQ ID NO; 35 is the nucleotide sequence of the ILV5 promoter.

SEQ ID NO; 38 is the nucleotide sequence of the ILV5 terminator.

SEQ ID NO; 39 is the nucleotide sequence of the FBA1 promoter.

SEQ ID NO; 42 is the nucleotide sequence of pLH468.

SEQ ID NO; 47 is the nucleotide sequence of pNY8.

SEQ ID NO; 48 is the nucleotide sequence of the GPD1 promoter.

SEQ ID NOs:49, 50, 54, 55, 62-71, 73-83 and 85-86 are the nucleotide sequences of primers used in the examples.

SEQ ID NO; 51 is the nucleotide sequence of pRS425::GPM-sadB.

SEQ ID NO; 52 is the nucleotide sequence of the GPM1 promoter.

SEQ ID NO:53 is the nucleotide sequence of the ADH1 terminator.

SEQ ID NO:56 is the nucleotide sequence of pRS423 FBA ilvD(Strep).

SEQ ID NO:57 is the nucleotide sequence of the FBA terminator.

SEQ ID NO:60 is the nucleotide sequence of the GPM-sadB-ADHt segment.

SEQ ID NO:61 is the nucleotide sequence of pUC19-URA3r.

SEQ ID NO:72 is the nucleotide sequence of the ilvD-FBA1t segment.

SEQ ID NO:84 is the nucleotide sequence of the URA3r2 template DNA.

DETAILED DESCRIPTION

As used above and throughout the description of the invention, the following terms, unless otherwise indicated, shall be defined as follows:

The term "butanol" as used herein, refers to 1-butanol, 2-butanol, isobutanol, or mixtures thereof.

The term "aerobic conditions" as used herein, means growth conditions in the presence of oxygen.

The term "microaerobic conditions" as used herein, means growth conditions with low levels of oxygen (i.e., below normal atmospheric oxygen levels).

The term "anaerobic conditions" as used herein, means growth conditions in the absence of oxygen.

The term "fermentable carbon source" as used herein, refers to a carbon source capable of being metabolized by the microorganisms disclosed herein. Suitable fermentable carbon sources include, but are not limited to, monosaccharides, such as glucose or fructose; disaccharides, such as lactose or sucrose; oligosaccharides; polysaccharides, such as starch or cellulose; one carbon substrates; and mixtures thereof.

The term "extractant" as used herein refers to organic solvent used to extract any butanol isomer.

The term "biphasic fermentation medium" as used herein, refers to a two-phase growth medium comprising a fermentation medium (i.e., the aqueous phase) and a suitable amount of a water immiscible organic extractant.

The term "butanol biosynthetic pathway" as used herein, refers to an enzyme pathway to produce 1-butanol, 2-butanol, or isobutanol.

The term "1-butanol biosynthetic pathway" as used herein, refers to an enzyme pathway to produce 1-butanol from acetyl-coenzyme A (acetyl-CoA).

The term "2-butanol biosynthetic pathway" as used herein, refers to an enzyme pathway to produce 2-butanol from pyruvate.

The term "isobutanol biosynthetic pathway" as used herein, refers to an enzyme pathway to produce isobutanol from pyruvate.

The term "fatty acid" as used herein, refers to a carboxylic acid having a long, aliphatic chain (i.e., $C_{11}$ to $C_{22}$), which is either saturated or unsaturated.

The term "fatty alcohol" as used herein, refers to an alcohol having a long, aliphatic chain (i.e., $C_{11}$ to $C_{22}$), which is either saturated or unsaturated.

The term "fatty aldehyde" as used herein, refers to an aldehyde having a long, aliphatic chain (i.e., $C_{11}$ to $C_{22}$), which is either saturated or unsaturated.

The term "effective titer" as used herein, refers to the total amount of butanol produced by fermentation per liter of fermentation medium. The total amount of butanol includes the amount of butanol in the fermentation medium, and the amount of butanol recovered from the organic extractant and from the gas phase, if gas stripping is used.

The term "minimal media" as used herein, refers to growth media that contain the minimum nutrients possible for growth, generally without the presence of amino acids. A minimal medium typically contains a fermentable carbon source and various salts, which may vary among microorganisms and growing conditions; these salts generally provide essential elements such as magnesium, nitrogen, phosphorus, and sulfur to allow the microorganism to synthesize proteins and nucleic acids.

The term "defined media" as used herein, refers to growth media that have known quantities of all ingredients. e.g., a defined carbon source and nitrogen source, and trace elements and vitamins required by the microorganism.

The term "OD" as used herein, refers to optical density.

The term "$OD_{600}$" as used herein, refers to the optical density at a wavelength of 600 nm.

The term "id" as used herein, refers to internal diameter.

The term "Aq" as used herein, refers to aqueous phase.

The term "Org" as used herein, refers to organic phase.

The term "IPTG" as used herein, refers to isopropyl β-D-thiogalactopyranoside.

The term "vvm" as used herein, refers to volume to volume per minute.

The term "ATCC" as used herein, refers to the American Type Culture Collection, Manassas, Va.

The term "vol" means volume.
The term "rpm" means revolutions per minute.
The term "sec" means second(s).
The term "min" means minute(s).
The term "h" means hour(s).
The term "μL" means microliter.
The term "mL" means milliliter(s).
The term "L" means liter(s).
The term "mL/min" means milliliters per minute.
The term "mmol" means millimole(s).
The term "mM" means millimolar.
The term "M" means molar.
The term "μm" means micrometer.
The term "g" means grams.
The term "μg" means microgram.
The term "g/g" means gram per gram.
The term "g/L" means grams per liter.
The term "μg/mL" means microgram per liter.
The term "mg/L" means micgram per liter.
The term "mmol/min/mg" means millimole per minute per milligram.
The term "g/L/h" means grams per liter per hour.
The term "HPLC" means high pressure liquid chromatography.
The term "GC" means gas chromatography.

Genetically Modified Microorganisms

Microbial hosts for butanol production may be selected from bacteria, cyanobacteria, filamentous fungi and yeasts. The microbial host used should be tolerant to the butanol product produced, so that the yield is not limited by toxicity of the product to the host. The selection of a microbial host for butanol production is described in detail below.

Microbes that are metabolically active at high titer levels of butanol are not well known in the art. Although butanol-tolerant mutants have been isolated from solventogenic Clostridia, little information is available concerning the butanol tolerance of other potentially useful bacterial strains. Most of the studies on the comparison of alcohol tolerance in bacteria suggest that butanol is more toxic than ethanol (de Cavalho et al., *Microsc. Res. Tech.* 64:215-22 (2004) and Kabelitz et al., *FEMS Microbiol. Lett.* 220:223-227 (2003)). Tomas et al. (*J. Bacteriol.* 186:2006-2018 (2004)) report that the yield of 1-butanol during fermentation in Clostridium acetobutylicum may be limited by butanol toxicity. The primary effect of 1-butanol on Clostridium acetobutylicum is disruption of membrane functions (Hermann et al., *Appl. Environ. Microbiol.* 50:1238-1243 (1985)).

The microbial hosts selected for the production of butanol should be tolerant to butanol and should be able to convert carbohydrates to butanol using the introduced biosynthetic pathway as described below. The criteria for selection of suitable microbial hosts include the following: intrinsic tolerance to butanol, high rate of carbohydrate utilization, availability of genetic tools for gene manipulation, and the ability to generate stable chromosomal alterations.

Suitable host strains with a tolerance for butanol may be identified by screening based on the intrinsic tolerance of the strain. The intrinsic tolerance of microbes to butanol may be measured by determining the concentration of butanol that is responsible for 50% inhibition of the growth rate (IC50) when grown in a minimal medium. The IC50 values may be determined using methods known in the art. For example, the microbes of interest may be grown in the presence of various amounts of butanol and the growth rate monitored by measuring the optical density at 600 nanometers. The doubling time may be calculated from the logarithmic part of the growth curve and used as a measure of the growth rate. The concentration of butanol that produces 50% inhibition of growth may be determined from a graph of the percent inhibition of growth versus the butanol concentration. Preferably, the host strain should have an IC50 for butanol of greater than about 0.5%. More suitable is a host strain with an IC50 for butanol that is greater than about 1.5%. Particularly suitable is a host strain with an IC50 for butanol that is greater than about 2.5%.

The microbial host for butanol production should also utilize glucose and/or other carbohydrates at a high rate. Most microbes are capable of utilizing carbohydrates. However, certain environmental microbes cannot efficiently use carbohydrates, and therefore would not be suitable hosts.

The ability to genetically modify the host is essential for the production of any recombinant microorganism. Modes of gene transfer technology that may be used include by electroporation, conjugation, transduction or natural transformation. A broad range of host conjugative plasmids and drug resistance markers are available. The cloning vectors used with an organism are tailored to the host organism based on the nature of antibiotic resistance markers that can function in that host.

The microbial host also may be manipulated in order to inactivate competing pathways for carbon flow by inactivating various genes. This requires the availability of either transposons or chromosomal integration vectors to direct inactivation. Additionally, production hosts that are amenable to chemical mutagenesis may undergo improvements in intrinsic butanol tolerance through chemical mutagenesis and mutant screening.

Based on the criteria described above, suitable microbial hosts for the production of butanol include, but are not limited to, members of the genera, *Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Pichia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarum, Enterococcus faecalis, Pediococcus pentosaceus, Pediococcus acidilactici, Bacillus subtilis* and *Saccharomyces cerevisiae*.

Microorganisms mentioned above may be genetically modified to convert fermentable carbon sources into butanol, specifically 1-butanol, 2-butanol, or isobutanol, using methods known in the art. Particularly suitable microorganisms include *Escherichia Lactobacillus*, and *Saccharomyces*, where *E. coli, L. plantarum* and *S. cerevisiae* are particularly preferred. Additionally, the microorganism may be a butanol-tolerant strain of one of the microorganisms listed above that is isolated using the method described by Bramucci et al. (copending and commonly owned U.S. patent application Ser. No. 11/761,497; and WO 2007/146377). An example of one such strain is *Lactobacillus plantarum* strain PN0512 (ATCC: PTA-7727, biological deposit made Jul. 12, 2006 for U.S. patent application Ser. No. 11/761,497).

These microorganisms can be genetically modified to contain a 1-butanol biosynthetic pathway to produce 1-butanol, as described by Donaldson et al. in WO 2007/041269, incorporated herein by reference. For example, the microorganism may be genetically modified to express a 1-butanol biosynthetic pathway comprising the following enzyme-catalyzed substrate to product conversions:

a) acetyl-CoA to acetoacetyl-CoA;
b) acetoacetyl-CoA to 3-hydroxybutyryl-CoA;
c) 3-hydroxybutyryl-CoA to crotonyl-CoA;
d) crotonyl-CoA to butyryl-CoA;
e) butyryl-CoA to butyraldehyde; and
f) butyraldehyde to 1-butanol.

The microorganisms may also be genetically modified to express a 2-butanol biosynthetic pathway to produce 2-butanol, as described by Donaldson et al. in U.S. Patent Application Publication Nos. 2007/0259410 and 2007/0292927, WO 2007/130518 and WO 2007/130521, all of which are incorporated herein by reference. For example, in one embodiment the microorganism may be genetically modified to express a 2-butanol biosynthetic pathway comprising the following enzyme-catalyzed substrate to product conversions:

a) pyruvate to alpha-acetolactate;
b) alpha-acetolactate to acetoin;
c) acetoin to 2,3-butanediol;
d) 2,3-butanediol to 2-butanone; and
e) 2-butanone to 2-butanol.

The microorganisms may also be genetically modified to express an isobutanol biosynthetic pathway to produce isobutanol, as described by Donaldson et al. in U.S. Patent Application Publication No. 2007/0092957 and WO 2007/050671, both of which are incorporated herein by reference. For example, the microorganism may be genetically modified to contain an isobutanol biosynthetic pathway comprising the following enzyme-catalyzed substrate to product conversions:

a) pyruvate to acetolactate;
b) acetolactate to 2,3-dihydroxyisovalerate;
c) 2,3-dihydroxyisovalerate to α-ketoisovalerate;
d) α-ketoisovalerate to isobutyraldehyde; and
e) isobutyraldehyde to isobutanol.

The microorganism genetically modified to be capable of converting fermentable carbon sources into butanol may be a recombinant *Escherichia coli* strain that comprises an isobutanol biosynthetic pathway, as described above, and deletions of the following genes to eliminate competing pathways that limit isobutanol production, pflB, given as SEQ ID NO:23, (encoding for pyruvate formate lyase), ldhA, given as SEQ ID NO:24, (encoding for lactate dehydrogenase), adhE, given as SEQ ID NO:25, (encoding for alcohol dehydrogenase), and at least one gene comprising the frdABCD operon (encoding for fumarate reductase), specifically, frdA, given as SEQ ID NO:26, frdB, given as SEQ ID NO:27, frdC, given as SEQ ID NO:28, and frdD, given as SEQ ID NO:29, The *Escherichia coli* strain may comprise: (a) an isobutanol biosynthetic pathway encoded by the following genes: budB (given as SEQ ID NO:1) from *Klebsiella pneumoniae* encoding acetolactate synthase (given as SEQ ID NO:2), ilvC (given as SEQ ID NO:3) from *E. coli* encoding acetohydroxy acid reductoisomerase (given as SEQ ID NO:4), ilvD (given as SEQ ID NO:5) from *E. coli* encoding acetohydroxy acid dehydratase (given as SEQ ID NO:6), kivD (given as SEQ ID NO:7) from *Lactococcus lactis* encoding the branched-chain keto acid decarboxylase (given as SEQ ID NO:8), and sadB (given as SEQ ID NO:9) from *Achromobacter xylosoxidans* encoding a butanol dehydrogenase (given as SEQ ID NO:10); and (b) deletions of the following genes: pflB (SEQ ID NO:23), ldhA (SEQ ID NO:24) adhE (SEQ ID NO:25), and frdB (SEQ ID NO:27). The enzymes encoded by the genes of the isobutanol biosynthetic pathway catalyze the substrate to product conversions for converting pyruvate to isobutanol, as described above. Specifically, acetolactate synthase catalyzes the conversion of pyruvate to acetolactate, acetohydroxy acid reductoisomerase catalyzes the conversion of acetolactate to 2,3-dihydroxyisovalerate, acetohydroxy acid dehydratase catalyzes the conversion of 2,3-dihydroxyisovalerate to α-ketoisovalerate, branched-chain keto acid decarboxylase catalyzes the conversion of α-ketoisovalerate to isobutyraldehyde, and butanol dehydrogenase catalyzes the conversion of isobutyraldehyde to isobutanol. This recombinant *Escherichia coli* strain can be constructed using methods known in the art, as exemplified in the General Methods Section of the Examples herein below.

The *Saccharomyces cerevisiae* strain may comprise: an isobutanol biosynthetic pathway encoded by the following genes: alsS coding region from *Bacillus subtilis* (SEQ ID NO:32) encoding acetolactate synthase (SEQ ID NO:33), ILV5 from *S. cerevisiae* (SEQ ID NO:40) encoding acetohydroxy acid reductoisomerase (KAR1; SEQ ID NO:41) and/or a mutant KAR1 such as encoded by Pf5.IlvC-Z4B8 (SEQ ID NO:36; protein SEQ ID NO:37), ilvD from *Streptococcus mutans* (SEQ ID NO:58) encoding acetohydroxy acid dehydratase (SEQ ID NO:59), kivD from *Bacillus subtilis* (SEQ ID NO:43) encoding the branched-chain keto acid decarboxylase (SEQ ID NO:44), and sadB from *Achromobacter xylosoxidans* (SEQ ID NO:9) encoding a butanol dehydrogenase (SEQ ID NO:10). The enzymes encoded by the genes of the isobutanol biosynthetic pathway catalyze the substrate to product conversions for converting pyruvate to isobutanol, as described herein.

A preferred yeast strain expressing an isobutanol pathway has acetolactate synthase (ALS) activity in the cytosol and has deletions of the endogenous pyruvate decarboxylase (PDC) genes as described in commonly owned and co-pending U.S. Patent Application No. 61/058,970, which is herein incorporated by reference. This combination of cytosolic ALS and reduced PDC expression was found to greatly increase flux from pyruvate to acetolactate, which then flows to the pathway for production of isobutanol.

This recombinant *Saccharomyces cerevisiae* strain can be constructed using methods known in the art, as exemplified in the General Methods section of the Examples herein below.

Organic Extractants

Extractants useful in the Methods described herein are water immiscible organic solvents. Suitable organic extractants should meet the criteria for an ideal solvent for a commercial two-phase extractive fermentation for the production or recovery of butanol. Specifically, the extractant should (i) be nontoxic to the butanol-producing microorganisms such as, for example, genetically modified *Escherichia coli*, *Lactobacillus plantarum*, and *Saccharomyces cerevisiae*, (ii) be substantially immiscible with the fermentation medium, (iii) have a high partition coefficient for the extraction of butanol, (iv) have a low partition coefficient for the extraction of nutrients, (v) have a low tendency to form emulsions with the fermentation medium, and (vi) be low cost and nonhazardous. Suitable organic extractants for use in the Methods disclosed herein are selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof. As used herein, the term "mixtures thereof" encompasses both mixtures within and mixtures between these group members, for example mixtures within $C_{12}$ to $C_{22}$ fatty alcohols, and also mixtures between $C_{12}$ to $C_{22}$ fatty alcohols and $C_{12}$ to $C_{22}$ fatty acids, for example.

In some instances extractants having less than 12-carbon chain lengths can be harmful to the microorganism and therefore harmful to the process of providing butanol via a biosynthetic path. In the case of an 11-carbon extractant, the effect on a microorganism can be dependent on the conditions, but can be harmful. In the case where a $C_{11}$ fatty alcohol, $C_{11}$ fatty acid, an ester of a $C_{12}$ fatty acid, a $C_{11}$ aldehyde, and mixtures thereof can be deleterious to the process, for example in the case where a microorganism is adversely affected by the $C_{11}$ compound under the conditions used, such use is to be avoided. Suitable organic extractants are further selected from the group consisting of oleyl alcohol (CAS No. 143-28-2), behenyl alcohol (CAS No. 661-19-8), cetyl alcohol (CAS No. 36653-82-4), lauryl alcohol, also referred to as 1-dodecanol (CAS No. 112-53-8), myristyl alcohol (112-72-1), stearyl alcohol (CAS No. 112-92-5), 1-undecanol (CAS No. 112-42-5), oleic acid (CAS No. 112-80-1), lauric acid (CAS No. 143-07-7), myristic acid (CAS No. 544-63-8), stearic acid (CAS No. 57-11-4), methyl myristate CAS No. 124-10-7), methyl oleate (CAS No. 112-62-9), undecanal (CAS No. 112-44-7), lauric aldehyde (CAS No. 112-54-9), 2-methylundecanal (CAS No. 110-41-8), oleamide (CAS No. 301-02-0), linoleamide (CAS No. 3999-01-7), palmitamide (CAS No. 629-54-9) and stearylamide (CAS No. 124-26-5) and mixtures thereof. These organic extractants are available commercially from various sources, such as Sigma-Aldrich (St. Louis, Mo.), in various grades, many of which may be suitable for use in extractive fermentation to produce or recover butanol. Technical grades contain a mixture of compounds, including the desired component and higher and lower fatty components. For example, one commercially available technical grade oleyl alcohol contains about 65% oleyl alcohol and a mixture of higher and lower fatty alcohols.

One of reasonable skill in the art can appreciate that it may be advantageous to use a mixture of the organic extractants. For example, solvent mixtures may be used to increase the partition coefficient of the product. Additionally, solvent mixtures may be used to adjust and optimize physical characteristics of the solvent, such as the density, boiling point, and viscosity.

Methods for Producing Butanol Using Two-Phase Extractive Fermentation

The microorganism may be cultured in a suitable fermentation medium in a suitable fermentor to produce butanol. Any suitable fermentor may be used including a stirred tank fermentor, an airlift fermentor, a bubble fermentor, or any combination thereof. Materials and methods for the maintenance and growth of microbial cultures are well known to those skilled in the art of microbiology or fermentation science (See for example, Bailey et al., *Biochemical Engineering Fundamentals*, second edition, McGraw Hill, New York, 1986). Consideration must be given to appropriate fermentation medium, pH, temperature, and requirements for aerobic, microaerobic, or anaerobic conditions, depending on the specific requirements of the microorganism, the fermentation, and the process. The fermentation medium used is not critical, but it must support growth of the microorganism used and promote the biosynthetic pathway necessary to produce the desired butanol product. A conventional fermentation medium may be used, including, but not limited to, complex media containing organic nitrogen sources such as yeast extract or peptone and at least one fermentable carbon source; minimal media; and defined media. Suitable fermentable carbon sources include, but are not limited to, monosaccharides, such as glucose or fructose; disaccharides, such as lactose or sucrose; oligosaccharides; polysaccharides, such as starch or cellulose; one carbon substrates; and mixtures thereof. In addition to the appropriate carbon source, the fermentation medium may contain a suitable nitrogen source, such as an ammonium salt, yeast extract or peptone, minerals, salts, cofactors, buffers and other components, known to those skilled in the art (Bailey et al. supra). Suitable conditions for the extractive fermentation depend on the particular microorganism used and may be readily determined by one skilled in the art using routine experimentation.

Methods for Recovering Butanol Using Two-Phase Extractive Fermentation

Butanol may be recovered from a fermentation medium containing butanol, water, at least one fermentable carbon source, and a microorganism that has been genetically modified (that is, genetically engineered) to produce butanol via a biosynthetic pathway from at least one carbon source. Such genetically modified microorganisms can be selected from the group consisting of *Escherichia coli*, *Lactobacillus plantarum*, and *Saccharomyces cerevisiae*. The first step in the process is contacting the fermentation medium with a water immiscible organic extractant, described above, to form a two-phase mixture comprising an aqueous phase and a butanol-containing organic phase. "Contacting" means the fermentation medium and the organic extractant are brought into physical contact at any time during the fermentation process. In one embodiment, the fermentation medium further comprises ethanol, and the butanol-containing organic phase can contain ethanol.

The organic extractant may contact the fermentation medium at the start of the fermentation forming a biphasic fermentation medium. Alternatively, the organic extractant may contact the fermentation medium after the microorganism has achieved a desired amount of growth, which can be determined by measuring the optical density of the culture.

Further, the organic extractant may contact the fermentation medium at a time at which the butanol level in the fermentation medium reaches a preselected level, for example, before the butanol concentration reaches a toxic level. The butanol concentration may be monitored during the fermentation using methods known in the art, such as gas chromatography or high performance liquid chromatography.

Fermentation may be run under aerobic conditions for a time sufficient for the culture to achieve a preselected level of growth, as determined by optical density measurement. An inducer may then be added to induce the expression of the butanol biosynthetic pathway in the modified microorganism, and fermentation conditions are switched to microaerobic or anaerobic conditions to stimulate butanol production, as described in detail in Example 6 herein below. The extractant is added after the switch to microaerobic or anaerobic conditions.

After contacting the fermentation medium with the organic extractant, the butanol product partitions into the organic extractant, decreasing the concentration in the aqueous phase containing the microorganism, thereby limiting the exposure of the production microorganism to the inhibitory butanol product. The volume of the organic extractant to be used depends on a number of factors, including the volume of the fermentation medium, the size of the fermentor, the partition coefficient of the extractant for the butanol product, and the fermentation mode chosen, as described below. The volume of the organic extractant is about 3% to about 60% of the fermentor working volume.

The next step is separating the butanol-containing organic phase from the aqueous phase using methods known in the art, including but not limited to, siphoning, decantation, centrifugation, using a gravity settler, membrane-assisted phase splitting, and the like. Recovery of the butanol from the butanol-containing organic phase can be done using methods known in the art, including but not limited to, distillation, adsorption by resins, separation by molecular sieves, pervaporation, and the like. Specifically, distillation may be used to recover the butanol from the butanol-containing organic phase.

Gas stripping may be used concurrently with the organic extractant to remove the butanol product from the fermentation medium. Gas stripping may be done by passing a gas such as air, nitrogen, or carbon dioxide through the fermentation medium, thereby forming a butanol-containing gas phase. The butanol product may be recovered from the butanol-containing gas phase using methods known in the art, such as using a chilled water trap to condense the butanol, or scrubbing the gas phase with a solvent.

Any butanol remaining in the fermentation medium after the fermentation run is completed may be recovered by continued extraction using fresh or recycled organic extractant. Alternatively, the butanol can be recovered from the fermentation medium using methods known in the art, such as distillation, azeotropic distillation, liquid-liquid extraction, adsorption, gas stripping, membrane evaporation, pervaporation, and the like.

The two-phase extractive fermentation method may be carried out in a continuous mode in a stirred tank fermentor. In this mode, the mixture of the fermentation medium and the butanol-containing organic extractant is removed from the fermentor. The two phases are separated by means known in the art including, but not limited to, siphoning, decantation, centrifugation, using a gravity settler, membrane-assisted phase splitting, and the like, as described above. After separation, the fermentation medium may be recycled to the fermentor or may be replaced with fresh medium. Then, the extractant is treated to recover the butanol product as described above. The extractant may then be recycled back into the fermentor for further extraction of the product. Alternatively, fresh extractant may be continuously added to the fermentor to replace the removed extractant. This continuous mode of operation offers several advantages. Because the product is continually removed from the reactor, a smaller volume of organic extractant is required enabling a larger volume of the fermentation medium to be used. This results in higher production yields. The volume of the organic extractant may be about 3% to about 50% of the fermentor working volume; 3% to about 20% of the fermentor working volume; or 3% to about 10% of the fermentor working volume. It is beneficial to use the smallest amount of extractant in the fermentor as possible to maximize the volume of the aqueous phase, and therefore, the amount of cells in the fermentor. The process may be operated in an entirely continuous mode in which the extractant is continuously recycled between the fermentor and a separation apparatus and the fermentation medium is continuously removed from the fermentor and replenished with fresh medium. In this entirely continuous mode, the butanol product is not allowed to reach the critical toxic concentration and fresh nutrients are continuously provided so that the fermentation may be carried out for long periods of time. The apparatus that may be used to carryout these modes of two-phase extractive fermentations are well known in the art. Examples are described, for example, by Kollerup et al. in U.S. Pat. No. 4,865,973.

Batchwise fermentation mode may also be used. Batch fermentation, which is well known in the art, is a closed system in which the composition of the fermentation medium is set at the beginning of the fermentation and is not subjected to artificial alterations during the process. In this mode, a volume of organic extractant is added to the fermentor and the extractant is not removed during the process. Although this mode is simpler than the continuous or the entirely continuous modes described above, it requires a larger volume of organic extractant to minimize the concentration of the inhibitory butanol product in the fermentation medium. Consequently, the volume of the fermentation medium is less and the amount of product produced is less than that obtained using the continuous mode. The volume of the organic solvent in the batchwise mode may be 20% to about 60% of the fermentor working volume; or 30% to about 60% of the fermentor working volume. It is beneficial to use the smallest volume of extractant in the fermentor as possible, for the reason described above.

Fed-batch fermentation mode may also be used. Fed-batch fermentation is a variation of the standard batch system, in which the nutrients, for example glucose, are added in increments during the fermentation. The amount and the rate of addition of the nutrient may be determined by routine experimentation. For example, the concentration of critical nutrients in the fermentation medium may be monitored during the fermentation. Alternatively, more easily measured factors such as pH, dissolved oxygen, and the partial pressure of waste gases, such as carbon dioxide, may be monitored. From these measured parameters, the rate of nutrient addition may be determined. The amount of organic solvent used in this mode is the same as that used in the batch-wise mode, described above.

Extraction of the product may be done downstream of the fermentor, rather than in situ. In this external mode, the extraction of the butanol product into the organic extractant is carried out on the fermentation medium removed from the fermentor. The amount of organic solvent used is about 20% to about 60% of the fermentor working volume; or 30% to about 60% of the fermentor working volume. The fermentation medium may be removed from the fermentor continuously or periodically, and the extraction of the butanol product by the organic extractant may be done with or without the removal of the cells from the fermentation medium. The cells may be removed from the fermentation medium by means known in the art including, but not limited to, filtration or centrifugation. After separation of the fermentation medium from the extractant by means described above, the fermentation medium may be recycled into the fermentor, discarded, or treated for the removal of any remaining butanol product. Similarly, the isolated cells may also be recycled into the fermentor. After treatment to recover the butanol product, the extractant may be recycled for use in the extraction process. Alternatively, fresh extractant may be used. In this mode the solvent is not present in the fermentor, so the toxicity of the solvent is much less of a problem. If the cells are separated from the fermentation medium before contacting with the solvent, the problem of solvent toxicity is further reduced. Furthermore, using this external mode there is less chance of forming an emulsion and evaporation of the solvent is minimized, alleviating environmental concerns.

A method for the production of butanol is provided, wherein a microorganism that has been genetically modified of being capable of converting at least one fermentable carbon source into butanol, is grown in a biphasic fermentation medium. The biphasic fermentation medium comprises an aqueous phase and a water immiscible organic extractant, as described above, wherein the biphasic fermentation medium comprises from about 3% to about 60% by volume of the organic extractant. The microorganism may be grown in the biphasic fermentation medium for a time sufficient to extract butanol into the extractant to form a butanol-containing organic phase. In the case where the fermentation medium further comprises ethanol, the butanol-containing organic phase may contain ethanol. The butanol-containing organic phase is then separated from the aqueous phase, as described above. Subsequently, the butanol is recovered from the butanol-containing organic phase, as described above.

Isobutanol may be produced by extractive fermentation with the use of a modified *Escherichia coli* or *Saccharomyces cerevisiae* strain in combination with oleyl alcohol as the organic extractant. Using the method described herein provides a high effective titer for isobutanol. Atsumi et al. (*Nature* 451(3):86-90, 2008) report isobutanol titers up to 22 g/L using fermentation with an *Escherichia coli* that was genetically modified to contain an isobutanol biosynthetic pathway. Butanol produced by the method disclosed herein has an effective titer of greater than 22 g per liter of the fermentation medium. Alternatively, the butanol produced by methods disclosed has an effective titer of at least 25 g per liter of the fermentation medium. Alternatively, the butanol produced by methods described herein has an effective titer of at least 30 g per liter of the fermentation medium. Alternatively, the butanol produced by methods described herein has an effective titer of at least 37 g per liter of the fermentation medium.

Without being held to theory, it is believed that the higher butanol titer obtained with the extractive fermentation method disclosed herein results, in part, from the removal of the toxic butanol product from the fermentation medium, thereby keeping the level below that which is toxic to the microorganism.

The use of the organic extractant oleyl alcohol has an additional beneficial effect that is surprising and not well understood at the time of presenting this invention. Specifically, the use of oleyl alcohol as the extractant in combination with gas stripping provides significantly higher titers than gas stripping alone, even though gas stripping alone is effective in keeping the butanol below toxic levels. Organic extractants comprising or consisting essentially of oleyl alcohol can provide improved titers in the processes described herein.

Referring now to FIG. 3, there is shown a schematic representation of one embodiment of processes for producing and recovering butanol using in situ extractive fermentation. An aqueous stream 10 of at least one fermentable carbon source is introduced into a fermentor 20, which contains at least one microorganism (not shown) genetically modified to convert the at least one fermentable carbon source into butanol. A stream of the first water immiscible extractant 12 and a stream of the optional second water immiscible extractant 14 are introduced to a vessel 16, in which the extractants are combined to form the extractant 18. A stream of the extractant 18 is introduced into the fermentor 20, whereby contact between the fermentation medium and the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Referring now to FIG. 4, there is shown a schematic representation of one embodiment of processes for producing and recovering butanol using in situ extractive fermentation. An aqueous stream 10 of at least one fermentable carbon source is introduced into a fermentor 20, which contains at least one microorganism (not shown) genetically modified to convert the at least one fermentable carbon source into butanol. A stream of the first water immiscible extractant 12 and a stream of the optional second water immiscible extractant 14 are introduced separately to the fermentor 20, whereby contact between the fermentation medium and the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Referring now to FIG. 5, there is shown a schematic representation of one embodiment of processes for producing and recovering butanol using in situ extractive fermentation. An aqueous stream 10 of at least one fermentable carbon source is introduced into a first fermentor 20, which contains at least one microorganism (not shown) genetically modified to convert the at least one fermentable carbon source into butanol. A stream of the first water immiscible extractant 12 is introduced to the fermentor 20, and a stream 22 comprising a mixture of the first solvent and the contents of fermentor 20 is introduced into a second fermentor 24. A stream of the optional second water immiscible extractant 14 is introduced into the second fermentor 24, whereby contact between the fermentation medium and the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Referring now to FIG. 6, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one microorganism (not shown) genetically modified to convert the at least one fermentable carbon source into butanol. A stream of the first water immiscible extractant 112 and a stream of the optional second water immiscible extractant 114 are introduced to a vessel 116, in which the water immiscible extractants are combined to form the extractant 118. At least a portion, shown as stream 122, of the fermentation medium in fermentor 120 is introduced into vessel 124. A stream of the extractant 118 is also introduced into vessel 124, whereby contact between the fermentation medium and the extractant to form a two-phase mixture comprising an aqueous phase and a butanol-containing organic phase occurs. A stream 126 comprising both the aqueous and organic phases is introduced into a vessel 138, in which separation of the aqueous and organic phases is performed to produce a butanol-containing organic phase 140 and an aqueous phase 142.

Referring now to FIG. 7, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one microorganism (not shown) genetically modified to convert the at least one fermentable carbon source into butanol. A stream of the first water immiscible extractant 112 and a stream of the optional second water immiscible extractant 114 are introduced separately to a vessel 124, in which the water immiscible extractants are combined to form the extractant 118. At least a portion, shown as stream 122, of the fermentation medium in fermentor 120 is also introduced into vessel 124, whereby contact between the fermentation medium and the extractant to form a two-phase mixture comprising an aqueous phase and a butanol-containing organic phase occurs. A stream 126 comprising both the aqueous and organic phases is introduced into a vessel 138, in which separation of the aqueous and organic phases is performed to produce a butanol-containing organic phase 140 and an aqueous phase 142.

Referring now to FIG. 8, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one microorganism (not shown) genetically modified to convert the at least one fermentable carbon source into butanol. A stream of the first water immiscible extractant 112 is introduced to a vessel 128, and at least a portion, shown as stream 122, of the fermentation medium in fermentor 120 is also introduced into vessel 128. A stream 130 comprising a mixture of the first water immiscible extractant and the contents of fermentor 120 is introduced into a second vessel 132. A stream of the optional second water immiscible extractant 114 is introduced into the second vessel 132, whereby contact between the fermentation medium and the extractant to form a two-phase mixture comprising an aqueous phase and a butanol-containing organic phase occurs. A stream 134 comprising both the aqueous and organic phases is introduced into a vessel 138, in which separation of the aqueous and organic phases is performed to produce a butanol-containing organic phase 140 and an aqueous phase 142.

The extractive processes described herein can be run as batch processes or can be run in a continuous mode where fresh extractant is added and used extractant is pumped out such that the amount of extractant in the fermentor remains constant during the entire fermentation process. Such continuous extraction of products and byproducts from the fermentation can increase effective rate, titer and yield.

In yet another embodiment, it is also possible to operate the liquid-liquid extraction in a flexible co-current or, alternatively, counter-current way that accounts for the difference in batch operating profiles when a series of batch fermentors are used. In this scenario the fermentors are filled with fermentable mash which provides at least one fermentable carbon source and microorganism in a continuous fashion one after another for as long as the plant is operating. Referring to FIG. 9, once Fermentor F100 fills with mash and microorganism, the mash and microorganism feeds advance to Fermentor F101 and then to Fermentor F102 and then back to Fermentor F100 in a continuous loop. The fermentation in any one fermentor begins once mash and microorganism are present together and continues until the fermentation is complete. The mash and microorganism fill time equals the number of fermentors divided by the total cycle time (fill, ferment, empty and clean). If the total cycle time is 60 hours and there are 3 fermentors then the fill time is 20 hours. If the total cycle time is 60 hours and there are 4 fermentors then the fill time is 15 hours.

Adaptive co-current extraction follows the fermentation profile assuming the fermentor operating at the higher broth phase titer can utilize the extracting solvent stream richest in butanol concentration and the fermentor operating at the lowest broth phase titer will benefit from the extracting solvent stream leanest in butanol concentration. For example, referring again to FIG. 9, consider the case where Fermentor F100 is at the start of a fermentation and operating at relatively low butanol broth phase (B) titer, Fermentor F101 is in the middle of a fermentation operating at relatively moderate butanol broth phase titer and Fermentor F102 is near the end of a fermentation operating at relatively high butanol broth phase titer. In this case, lean extracting solvent (S), with minimal or no extracted butanol, can be fed to Fermentor F100, the "solvent out" stream (S') from Fermentor F100 having an extracted butanol component can then be fed to Fermentor F101 as its "solvent in" stream and the solvent out stream from F101 can then e fed to Fermentor F102 as its solvent in stream. The solvent out stream from F102 can then be sent to be processed to recover the butanol present in the stream. The processed solvent stream from which most of the butanol is removed can be returned to the system as lean extracting solvent and would be the solvent in feed to Fermentor F100 above.

As the fermentations proceed in an orderly fashion the valves in the extracting solvent manifold can be repositioned to feed the leanest extracting solvent to the fermentor operating at the lowest butanol broth phase titer. For example, assume (a) Fermentor F102 completes its fermentation and has been reloaded and fermentation begins anew, (b) Fermentor F100 is in the middle of its fermentation operating at moderate butanol broth phase titer and (c) Fermentor F101 is near the end of its fermentation operating at relatively higher butanol broth phase titer. In this scenario the leanest extracting solvent would feed F102, the extracting solvent leaving F102 would feed Fermentor F100 and the extracting solvent leaving Fermentor F100 would feed Fermentor F101.

The advantage of operating this way can be to maintain the broth phase butanol titer as low as possible for as long as possible to realize improvements in productivity. Additionally, it can be possible to drop the temperature in the other fermentors that have progressed further into fermentation that are operating at higher butanol broth phase titers. The drop in temperature can allow for improved tolerance to the higher butanol broth phase titers.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

All solvents (that is, extractants) were obtained from Sigma-Aldrich (St. Louis, Mo.) and were used without further purification. The oleyl alcohol used was technical grade, which contained a mixture of oleyl alcohol (65%) and higher and lower fatty alcohols. The purity of the other solvents used was as follows: oleic acid, 65 to 88%; octanoic acid, 98%; nonanol, 98%; 1-dodecanol, 98%; 1-nonanal, 95%, and 1-decanol, 98%. Isobutanol was obtained from Sigma-Aldrich and was used without further purification.

General Methods

Construction of Recombinant *Escherichia coli* Strain NGCI-031

A recombinant *Escherichia coli* strain comprising an isobutanol biosynthetic pathway and deletions of the following genes, pflB (SEQ ID NO:23, encoding for pyruvate formate lyase), IdhA (SEQ ID NO:24, encoding for lactate dehydrogenase), adhE (SEQ ID NO:25, encoding for alcohol dehydrogenase), and frdB (SEQ ID NO:27, encoding a subunit of fumarate reductase), was constructed as described below. The genes in the isobutanol biosynthetic pathway were budB from *Klebsiella pneumoniae* (given as SEQ ID NO:1), ilvC from *Escherichia coli* (given as SEQ ID NO:3), ilvD from *Escherichia coli* (given as SEQ ID NO:5), kivD from *Lactococcus* lactis (given as SEQ ID NO:7), and sadB from *Achromobacter xylosoxidans* (given as SEQ ID NO:9). The construction of the recombinant strain was done in two steps. First, an *Escherichia coli* strain having the aforementioned gene deletions was constructed. Then, the genes encoding the isobutanol biosynthetic pathway were introduced into the strain.

Construction of Recombinant *Escherichia coli* Strain Having Deletions of pflB, IdhA, adhE and frdB Genes The Keio collection of *E. coli* strains (Baba et al., *Mol. Syst. Biol.*, 2:1-11, 2006) was used for the production of the *E. coli* strain having the intended gene deletions, which is referred to herein as the four-knock out *E. coli* strain. The Keio collection is a library of single gene knockouts created in strain *E. coli* BW25113 by the method of Datsenko and Wanner (Datsenko, K. A. & Wanner, B. L., *Proc. Natl. Acad. Sci., U.S.A.* 97 6640-6645, 2000). In the collection, each deleted gene was replaced with a FRT-flanked kanamycin marker that was removable by Flp recombinase. The four-knock out *E. coli* strain was constructed by moving the knockout-kanamycin marker from the Keio donor strain by P1 transduction to a recipient strain. After each P1 transduction to produce a knockout, the kanamycin marker was removed by Flp recombinase. This markerless strain acted as the new donor strain for the next P1 transduction.

The four-knock out *E. coli* strain was constructed in Keio strain JW0886 by P1$_{vir}$ transductions with P1 phage lysates prepared from three Keio strains in addition to JW0886. The Keio strains used are listed below:

JW0886: the kan marker is inserted in the pflB gene
JW4114: the kan marker is inserted in the frdB gene
JW1375: the kan marker is inserted in the IdhA gene
JW1228: the kan marker is inserted in the adhE gene P1$_{vir}$ transductions were carried out as described by Miller with some modifications (Miller, J. H. 1992. *A Short Course in Bacterial Genetics*. Cold Spring Harbor Laboratory, Cold Spring Harbor, N.Y.). Briefly, to prepare a transducing lysate, cells of the donor strain were grown overnight in Luria-Bertani (LB) medium at 37° C. while shaking. An overnight growth of these cells was sub-cultured into LB medium containing 0.005 M CaCl$_2$ and placed in a 37° C. water bath with no aeration. One hour prior to adding phage, the cells were incubated at 37° C. with shaking. After final growth of the cells, a 1.0 mL aliquot of the culture was dispensed into 14-mL tubes and approximately $10^7$ P1$_{vir}$ phage was added. The tubes were incubated in a 37° C. water bath for 20 min, after which 2.5 mL of 0.8% LB top agar was added to each tube. The contents of the tubes were spread on an LB agar plate and were incubated at 37° C. The following day the soft agar layer was scraped into a centrifuge tube. The surface of the plate was washed with LB medium and added to the centrifuge tube, followed by a few drops of CHCl$_3$ and then the tube was vigorously agitated using a vortex mixer. After centrifugation at 4,000 rpm for 10 min, the supernatant containing the P1$_{vir}$ lysate was collected.

For transduction, the recipient strain was grown overnight in 1-2 mL of LB medium at 37° C. with shaking. Cultures were pelleted by centrifugation in a microcentrifuge (Eppendorf) at 10,000 rpm for 1 min at room temperature. The cell pellet was resuspended in an equal volume of MC buffer (0.1 M MgSO$_4$, 0.005 M CaCl$_2$), dispensed into tubes in 0.1 mL aliquots and 0.1 mL and 0.01 mL of P1$_{vir}$ lysate was added. A control tube containing no P1$_{vir}$ lysate was also included. The tubes were incubated for 20 min at 37° C. after which time, 0.2 mL of 0.1 M sodium citrate was added to stop the P1 infection. One mL of LB medium was added to each tube before the tubes were incubated at 37° C. for 1 h. After incubation the cells were pelleted as described above, resuspended in 50-200 μL of LB prior to spreading on the LB plates containing 25 μg/mL of kanamycin and were incubated overnight at 37° C. Transductants were screened by colony PCR with chromosome specific primers flanking the region upstream and downstream of the kanamycin marker insertion.

Removal of the kanamycin marker from the chromosome was obtained by transforming the kanamycin-resistant strain with plasmid pCP20 (Cherepanov, P. P. and Wackernagel, W., *Gene*, 158: 9-14, 1995) followed by spreading onto LB ampicillin (100 μg/mL) plates and incubating at 30° C. The pCP20 plasmid carries the yeast FLP recombinase under the control of the $\lambda_{PR}$ promoter. Expression from this promoter is controlled by the cI857 temperature-sensitive repressor residing on the plasmid. The origin of replication of pCP20 is also temperature sensitive. Ampicillin resistant colonies were streaked onto LB agar plates and incubated at 42° C. The higher incubation temperature simultaneously induced expression of the FLP recombinase and cured the pCP20 plasmid from the cell. Isolated colonies were patched to grids onto the LB plates containing kanamycin (25 μg/mL), and LB ampicillin (100 μg/mL) plates and LB plates. The resulting kanamycin-sensitive, ampicillin-sensitive colonies were screened by colony PCR to confirm removal of the kanamycin marker from the chromosome.

For colony PCR amplifications the HotStarTaq Master Mix (Qiagen, Valencia, Calif.; catalog no. 71805-3) was used according to the manufacturer's protocol. Into a 25 μL Master Mix reaction containing 0.2 μM of each chromosome specific PCR primer, a small amount of a colony was added. Amplification was carried out in a DNA Thermocycler GeneAmp 9700 (PE Applied Biosystems, Foster City, Calif.). Typical colony PCR conditions were as follows: 15 min at 95° C.; 30 cycles of 95° C. for 30 sec, annealing temperature ranging from 50-58° C. for 30 sec, primers extended at 72° C. with an extension time of approximately 1 min/kb of DNA; then 10 min at 72° C. followed by a hold at 4° C. PCR product sizes were determined by gel electrophoresis by comparison with known molecular weight standards.

For transformations, electrocompetent cells of *E. coli* were prepared as described by Ausubel, F. M., et al., (Current Protocols in Molecular Biology, 1987, Wiley-Interscience,). Cells were grown in 25-50 mL of LB medium at 30-37° C. and harvested at an $OD_{600}$ of 0.5-0.7 by centrifugation at 10,000 rpm for 10 min. These cells are washed twice in sterile ice-cold water in a volume equal to the original starting volume of the culture. After the final wash cells were resuspended in sterile water and the DNA to be transformed was added. The cells and DNA were transferred to chilled cuvettes and electroporated in a Bio-Rad Gene Pulser II according to manufacturer's instructions (Bio-Rad Laboratories, Inc Hercules, Calif.).

Strain JW0886 (ΔpflB::kan) was transformed with plasmid pCP20 and spread on LB plates containing 100 µg/mL of ampicillin at 30° C. Ampicillin resistant transformants were then selected, streaked on LB plates and grown at 42° C. Isolated colonies were patched onto the ampicillin and kanamycin selective medium plates and LB plates. Kanamycin-sensitive and ampicillin-sensitive colonies were screened by colony PCR with primers pflB CkUp (SEQ ID NO:11) and pflB CkDn (SEQ ID NO:12). A 10 µL aliquot of the PCR reaction mix was analyzed by gel electrophoresis. The expected approximate 0.4 kb PCR product was observed confirming removal of the marker and creating the "JW0886 markerless" strain. This strain had a deletion of the pflB gene.

The "JW0886 markerless" strain was transduced with a $P1_{vir}$ lysate from JW4114 (frdB::kan) and streaked onto the LB plates containing 25 µg/mL of kanamycin. The kanamycin-resistant transductants were screened by colony PCR with primers frdB CkUp (SEQ ID NO:13) and frdB CkDn (SEQ ID NO: 14). Colonies that produced the expected approximate 1.6 kb PCR product were made electrocompetent, as described above, and transformed with pCP20 for marker removal as described above. Transformants were first spread onto LB plates containing 100 µg/mL of ampicillin at 30° C. and ampicillin resistant transformants were then selected and streaked on LB plates and grown at 42° C. Isolated colonies were patched onto ampicillin and the kanamycin selective medium plates and LB plates. Kanamycin-sensitive, ampicillin-sensitive colonies were screened by PCR with primers frdB CkUp (SEQ ID NO:13) and frdB CkDn (SEQ ID NO: 14). The expected approximate 0.4 kb PCR product was observed confirming marker removal and creating the double knockout strain, "ΔpflB frdB".

The double knockout strain was transduced with a $P1_{vir}$ lysate from JW1375 (ΔldhA::kan) and spread onto the LB plates containing 25 µg/mL of kanamycin. The kanamycin-resistant transductants were screened by colony PCR with primers IdhA CkUp (SEQ ID NO:15) and IdhA CkDn (SEQ ID NO:16). Clones producing the expected 1.1 kb PCR product were made electrocompetent and transformed with pCP20 for marker removal as described above. Transformants were spread onto LB plates containing 100 µg/mL of ampicillin at 30° C. and ampicillin resistant transformants were streaked on LB plates and grown at 42° C. Isolated colonies were patched onto ampicillin and kanamycin selective medium plates and LB plates. Kanamycin-sensitive, ampicillin-sensitive colonies were screened by PCR with primers IdhA CkUp (SEQ ID NO:15) and IdhA CkDn (SEQ ID NO:16) for a 0.3 kb product. Clones that produced the expected approximate 0.3 kb PCR product confirmed marker removal and created the triple knockout strain designated the "three-knock out strain" (ΔpflB frdB IdhA).

The "three-knock out strain" was transduced with a $P1_{vir}$ lysate from JW1228 (ΔadhE::kan) and spread onto the LB plates containing 25 µg/mL kanamycin. The kanamycin-resistant transductants were screened by colony PCR with primers adhE CkUp (SEQ ID NO: 17) and adhE CkDn (SEQ ID NO:18). Clones that produced the expected 1.6 kb PCR product were made electrocompetent and transformed with pCP20 for marker removal. Transformants were spread onto LB plates containing 100 µg/mL of ampicillin at 30° C. Ampicillin resistant transformants were streaked on LB plates and grown at 42° C. Isolated colonies were patched onto ampicillin and kanamycin selective plates and LB plates. Kanamycin-sensitive, ampicillin-sensitive colonies were screened by PCR with the primers adhE CkUp (SEQ ID NO: 17) and adhE CkDn (SEQ ID NO:18). Clones that produced the expected approximate 0.4 kb PCR product were named the "four-knock out strain" (ΔpflB frdB IdhA adhE).

Introduction of the Set of Genes Encoding an Isobutanol Biosynthetic Pathway into the Four-Knock Out *E. coli* Strain.

The plasmid pTrc99A::budB-ilvC-ilvD-kivD was constructed as described in Examples 9-14 of copending and commonly owned U.S. Patent Application Publication No. 2007/0092957, which are incorporated herein by reference. This plasmid comprised the following genes, budB encoding acetolactate synthase from *Klebsiella pneumoniae* (SEQ ID NO:1), ilvC gene encoding acetohydroxy acid reductoisomerase from *E. coli* (SEQ ID NO:3), ilvD encoding acetohydroxy acid dehydratase from *E. coli* (SEQ ID NO:5), and kivD encoding the branched-chain keto acid decarboxylase from *Lactococcus lactis* (SEQ ID NO:7). The sadB gene from *Achromobacter xylosoxidans* encoding a butanol dehydrogenase (SEQ ID NO:9) was subcloned into the pTrc99A::budB-ilvC-ilvD-kivD plasmid as described below.

A DNA fragment encoding a butanol dehydrogenase (DNA: SEQ ID NO:9; protein: SEQ ID NO:10) from *Achromobacter xylosoxidans* (disclosed in copending and commonly owned U.S. Patent Application No. 61/048,291) was amplified from *A. xylosoxidans* genomic DNA using standard conditions. The DNA was prepared using a Gentra Puregene kit (Gentra Systems, Inc., Minneapolis, Minn.; catalog number D-5500A) following the recommended protocol for gram negative organisms. PCR amplification was done using forward and reverse primers N473 and N469 (SEQ ID NOs:19 and 20, respectively) with Phusion high Fidelity DNA Polymerase (New England Biolabs, Beverly, Mass.). The PCR product was TOPO-Blunt cloned into pCR4 BLUNT (Invitrogen) to produce pCR4Blunt::sadB, which was transformed into *E. coli* Mach-1 cells. Plasmid was subsequently isolated from four clones, and the sequence verified.

The sadB coding region was then cloned into the vector pTrc99a (Amann et al., *Gene* 69: 301-315, 1988). The pCR4Blunt::sadB was digested with EcoRI, releasing the sadB fragment, which was ligated with EcoRI-digested pTrc99a to generate pTrc99a::sadB. This plasmid was transformed into *E. coli* Mach 1 cells and the resulting transformant was named Mach1/pTrc99a::sadB. The activity of the enzyme expressed from the sadB gene in these cells was determined to be 3.5 mmol/min/mg protein in cell-free extracts when analyzed using isobutyraldehyde as the standard.

Then, the sadB gene was subcloned into pTrc99A::budB-ilvC-ilvD-kivD as follows. The sadB coding region was amplified from pTrc99a::sadB using primers N695A (SEQ ID NO:21) and N696A (SEQ ID NO:22) with Phusion High Fidelity DNA Polymerase (New England Biolabs, Beverly, Mass.). Amplification was carried out with an initial denaturation at 98° C. for 1 min, followed by 30 cycles of denaturation at 98° C. for 10 sec, annealing at 62° C. for 30 sec, elongation at 72° C. for 20 sec and a final elongation cycle at 72° C. for 5 min, followed by a 4° C. hold. Primer N695A contained an AvrII restriction site for cloning and a RBS (ribosomal binding site) upstream of the ATG start codon of the sadB coding region. The N696A primer included an XbaI site for cloning. The 1.1 kb PCR product was digested with AvrII and XbaI (New England Biolabs, Beverly, Mass.) and gel purified using a Qiaquick Gel Extraction Kit (Qiagen Inc., Valencia, Calif.)). The purified fragment was ligated with pTrc99A::budB-ilvC-ilvD-kivD, that had been cut with the same restriction enzymes, using T4 DNA ligase (New England Biolabs, Beverly, Mass.). The ligation mixture was incubated at 16° C. overnight and then transformed into E. coli Mach 1™ competent cells (Invitrogen) according to the manufacturer's protocol. Transformants were obtained following growth on LB agar with 100 µg/ml of ampicillin. Plasmid DNA from the transformants was prepared with QIAprep Spin Miniprep Kit (Qiagen Inc., Valencia, Calif.) according to manufacturer's protocols. The resulting plasmid was called pTrc99A::budB-ilvC-ilvD-kivD-sadB. Electrocompetent four-knock out E. coli cells, prepared as described above, were transformed with pTrc99A::budB-ilvC-ilvD-kivD-sadB. Transformants were streaked onto LB agar plates containing 100 µg/mL of ampicillin. The resulting recombinant E. coli strain comprised an isobutanol biosynthetic pathway, encoded by plasmid pTrc99A::budB-ilvC-ilvD-kivD-sadB, and deletions of pflB, frdB, IdhA, and adhE genes and was designated as strain NGCI-031.

Construction of the Yeast Strain NGI-049

NGI-049 is a Saccharomyces cerevisiae strain with insertion-inactivation of endogenous PDC1, PDC5, and PDC6 genes, and containing expression vectors pLH475-Z4B8 and pLH468. PDC1, PDC5, and PDC6 genes encode the three major isozymes of pyruvate decarboxylase. The strain expresses genes encoding enzymes for an isobutanol biosynthetic pathway that are integrated or on plasmids.

Expression Vector pLH475-Z4B8

The pLH475-Z4B8 plasmid (SEQ ID NO:30) was constructed for expression of ALS and KAR1 in yeast. pLH475-Z4B8 is a pHR81 vector (ATCC #87541) containing the following chimeric genes: 1) the CUP1 promoter (SEQ ID NO:31), acetolactate synthase coding region from Bacillus subtilis (AlsS; SEQ ID NO:32; protein SEQ ID NO:33) and CYC1 terminator (SEQ ID NO:34); 2) an ILV5 promoter (SEQ ID NO:35), Pf5.IlvC-Z4B8 coding region (SEQ ID NO:36; protein SEQ ID NO:37) and ILV5 terminator (SEQ ID NO:38); and 3) the FBA1 promoter (SEQ ID NO:39), S. cerevisiae KAR1 coding region (ILV5; SEQ ID NO:40; protein SEQ ID NO:41) and CYC1 terminator.

The Pf5.IlvC-Z4B8 coding region is a sequence encoding KAR1 derived from Pseudomonas fluorescens but containing mutations, that was described in commonly owned and co-pending U.S. patent application Ser. No. 12/337,736, which is herein incorporated by reference. The Pf5.IlvC-Z4B8 encoded KAR1 (SEQ ID NO:37;) has the following amino acid changes as compared to the natural Pseudomonas fluorescens KAR1:

C33L: cysteine at position 33 changed to leucine,
R47Y: arginine at position 47 changed to tyrosine,
S50A: serine at position 50 changed to alanine,
T52D: threonine at position 52 changed to asparagine,
V53A: valine at position 53 changed to alanine,
L61F: leucine at position 61 changed to phenylalanine,
T80I: threonine at position 80 changed to isoleucine,
A156V: alanine at position 156 changed to threonine, and
G170A: glycine at position 170 changed to alanine.

The Pf5.IlvC-Z4B8 coding region was synthesized by DNA 2.0 (Palo Alto, Calif.; SEQ ID NO:6) based on codons that were optimized for expression in Saccharomyces cerevisiae.

Expression Vector pLH468

The pLH468 plasmid (SEQ ID NO:42) was constructed for expression of DHAD, KivD and HADH in yeast.

Coding regions for B. subtilis ketoisovalerate decarboxylase (KivD) and Horse liver alcohol dehydrogenase (HADH) were synthesized by DNA2.0 based on codons that were optimized for expression in Saccharomyces cerevisiae (SEQ ID NO:43 and 45, respectively) and provided in plasmids pKivDy-DNA2.0 and pHadhy-DNA2.0. The encoded proteins are SEQ ID NOs:44 and 46, respectively. Individual expression vectors for KivD and HADH were constructed. To assemble pLH467 (pRS426::$P_{GRD1}$-kivDy-GPD1t), vector pNY8 (SEQ ID NO:47; also named pRS426.GPD-ald-GPDt, described in commonly owned and co-pending US Patent App. Pub. US2008/0182308, Example 17, which is herein incorporated by reference) was digested with AscI and SfiI enzymes, thus excising the GPD1 promoter and the ald coding region. A GPD1 promoter fragment (SEQ ID NO:48) from pNY8 was PCR amplified to add an AscI site at the 5' end, and an SpeI site at the 3' end, using 5' primer OT1068 and 3' primer OT1067 (SEQ ID NOs:49 and 50). The AscI/SfiI digested pNY8 vector fragment was ligated with the GPD1 promoter PCR product digested with AscI and SpeI, and the SpeI-SfiI fragment containing the codon optimized kivD coding region isolated from the vector pKivD-DNA2.0. The triple ligation generated vector pLH467 (pRS426::$P_{GPD1}$-kivDy-GPD1t). pLH467 was verified by restriction mapping and sequencing.

pLH435 (pRS425::$P_{GPM1}$-Hadhy-ADH1t) was derived from vector pRS425::GPM-sadB (SEQ ID NO:51) which is described in commonly owned and co-pending U.S. Patent App. No. 61/058,970, Example 3, which is herein incorporated by reference. pRS425::GPM-sadB is the pRS425 vector (ATCC #77106) with a chimeric gene containing the GPM1 promoter (SEQ ID NO:52), coding region from a butanol dehydrogenase of Achromobacter xylosoxidans (sadB; SEQ ID NO:9; protein SEQ ID NO:10: disclosed in commonly owned and co-pending U.S. Patent App. No. 61/048,291), and ADH1 terminator (SEQ ID NO:53). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NO:54 and 55) to generate vector pRS425-GPMp-sadB-NheI, which was verified by sequencing. pRS425::$P_{GPM1}$-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC #87474) was digested with SacI and NotI, and ligated with the SacI-SalI fragment from pLH467 that contains the $P_{GPD1}$-kivDy-GPD1t cassette together with the SalI-NotI fragment from pLH435 that contains the $P_{GPM1}$-Hadhy-ADH1t cassette in a triple ligation reaction. This yielded the vector pRS411::$P_{GPD1}$-kivDy-$P_{GPM1}$-Hadhy (pLH441), which was verified by restriction mapping.

In order to generate a co-expression vector for all three genes in the lower isobutanol pathway: ilvD, kivDy and Hadhy, we used pRS423 FBA ilvD(Strep) (SEQ ID NO:56), which is described in commonly owned and co-pending U.S. Patent Application No. 61/100,792, as the source of the IlvD gene. This shuttle vector contains an F1 origin of replication (nt 1423 to 1879) for maintenance in *E. coli* and a 2 micron origin (nt 8082 to 9426) for replication in yeast. The vector has an FBA promoter (nt 2111 to 3108; SEQ ID NO:39) and FBA terminator (nt 4861 to 5860; SEQ ID NO:57). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO:58; protein SEQ ID NO:59) from *Streptococcus mutans* UA159 (ATCC #700610) is between the FBA promoter and FBA terminator forming a chimeric gene for expression. In addition there is a lumio tag fused to the ilvD coding region (nt 4829-4849).

The first step was to linearize pRS423 FBA ilvD(Strep) (also called pRS423-FBA(SpeI)-ilvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 by fragment. This fragment was ligated with the 9,482 by vector fragment from pRS423-FBA(SpeI)-IlvD (*Streptococcus mutans*)-Lumio. This generated vector pLH468 (pRS423::$P_{FBA1}$-ilvD(Strep)Lumio-FBA1t-$P_{GPD1}$-kivDy-GPD1t-$P_{GPM1}$-hadhy-ADH1t), which was confirmed by restriction mapping and sequencing.

Construction of pdc6::GPMp1-sadB Integration Cassette and PDC6 Deletion:

A pdc6::GPM1p-sadB-ADH1t-URA3r integration cassette was made by joining the GPM-sadB-ADHt segment (SEQ ID NO:60) from pRS425::GPM-sadB (described above) to the URA3r gene from pUC19-URA3r. pUC19-URA3r (SEQ ID NO:61) contains the URA3 marker from pRS426 (ATCC #77107) flanked by 75 bp homologous repeat sequences to allow homologous recombination in vivo and removal of the URA3 marker. The two DNA segments were joined by SOE PCR (as described by Horton et al. (1989) Gene 77:61-68) using as template pRS425::GPM-sadB and pUC19-URA3r plasmid DNAs, with Phusion DNA polymerase (New England Biolabs Inc., Beverly, Mass.; catalog no. F-5405) and primers 114117-11A through 114117-11D (SEQ ID NOs:62, 63, 64 and 65), and 114117-13A and 114117-13B (SEQ ID NOs:66 and 67).

The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC #200866) and transformants were maintained on synthetic complete media lacking uracil and supplemented with 2% glucose at 30° C. using standard genetic techniques (*Methods in Yeast Genetics*, 2005, Cold Spring Harbor Laboratory Press, Cold Spring Harbor, N.Y., pp. 201-202). Transformants were screened by PCR using primers 112590-34G and 112590-34H (SEQ ID NOs:68 and 69), and 112590-34F and 112590-49E (SEQ ID NOs:70 and 71) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700 pdc6::$P_{GPM1}$-sadB-ADH1t.

Construction of pdc1:: PDC1-ilvD Integration Cassette and PDC1 Deletion:

A pdc1::PDC1p-ilvD-FBA1t-URA3r integration cassette was made by joining the ilvD-FBA1t segment (SEQ ID NO:72) from pLH468 (described above) to the URA3r gene from pUC19-URA3r by SOE PCR (as described by Horton et al. (1989) Gene 77:61-68) using as template pLH468 and pUC19-URA3r plasmid DNAs, with Phusion DNA polymerase (New England Biolabs Inc., Beverly, Mass.; catalog no. F-5405) and primers 114117-27A through 114117-27D (SEQ ID NOs:73, 74, 75 and 76).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::$P_{GPM1}$-sadB-ADH1t and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 114117-36D and 135 (SEQ ID NOs:77 and 78), and primers 112590-49E and 112590-30F (SEQ ID NOs:70 and 79) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6::GPM1p-sadB-ADH1t pdc1::PDC1p-ilvD-FBA1t.

HIS3 Deletion

To delete the endogenous HIS3 coding region, a his3:: URA3r2 cassette was PCR-amplified from URA3r2 template DNA (SEQ ID NO:84). URA3r2 contains the URA3 marker from pRS426 (ATCC #77107) flanked by 500 bp homologous repeat sequences to allow homologous recombination in vivo and removal of the URA3 marker. PCR was done using Phusion DNA polymerase and primers 114117-45A and 114117-45B (SEQ ID NOs:85 and 86) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (*Methods in Yeast Genetics*, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA73" has the genotype: BY4700 pdc6::GPM1p-sadB-ADH1t pdc1::PDC1p-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 403-4091) using Phusion DNA polymerase and primers PDC5::KanMXF and PDC5::KanMXR (SEQ ID NOs:80 and 81) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (*Methods in Yeast Genetics*, 2005, Cold Spring Harbor Laboratory Press, Cold Spring Harbor, N.Y., pp. 201-202) and transformants were selected on YP media supplemented with 1% ethanol and geneticin (200 µg/ml) at 30° C. Transformants were screened by PCR to verify correct integration at the PDC locus with replacement of the PDC5 coding region using primers PDC5kofor and N175 (SEQ ID NOs:82 and 83). The identified correct transformants have the genotype: BY4700 pdc6::GPM1p-sadB-ADH1t pdc1::PDC1p-ilvD-FBA1t Δhis3 pdc5::kanMX4.

Plasmid vectors pLH468 and pLH475-Z4B8 were simultaneously transformed into strain BY4700 pdc6::GPM1p-sadB-ADH1t pdc1::PDC1p-ilvD-FBA1t Δhis3 pdc5::kanMX4 using standard genetic techniques (*Methods in Yeast Genetics*, 2005, Cold Spring Harbor Laboratory Press, Cold Spring Harbor, N.Y.).and maintained on synthetic complete media lacking histidine and uracil, and supplemented with 1% ethanol at 30° C.

GC Method for Determination of Isobutanol

The following GC method was used to determine the amount of isobutanol in the aqueous phase and organic phase in Examples 1-7 described below. The GC method utilized an HP-InnoWax column (30 m×0.32 mm ID, 0.25 µm film) from Agilent Technologies (Santa Clara, Calif.). The carrier gas was helium at a flow rate of 1 mL/min measured at 150° C. with constant head pressure; injector split was 1:10 at 200° C.; oven temperature was 45° C. for 1 min, 45° C. to 230° C. at 10° C./min, and 230° C. for 30 sec. Flame ionization detection was used at 260° C. with 40 mL/min helium makeup gas. Culture broth samples were filtered through 0.2 µm spin filters before injection. Depending on the analytical sensitivity desired, either 0.1 µL or 0.5 µL injection volumes were used. Calibrated standard curves were generated for the following compounds: ethanol, isobutanol, acetoin, meso-2,3-butanediol, and (2S,3S)-2,3-butanediol. Analytical standards were also utilized to identify retention times for isobutyraldehyde, isobutyric acid, and isoamyl alcohol. Under these conditions, the isobutanol retention time was about 5.33 minutes.

HPLC Method for Determination of Glucose and Isobutanol in the Aqueous Phase

For Examples 7 and 8, isobutanol in the organic phase was determined using the GC method described above. For Examples 7 and 8, isobutanol and glucose concentrations in the aqueous phase were measured by HPLC (Waters Alliance Model, Milford, Mass. or Agilent 1100 Series, Santa Clara, Calif.) using a Shodex sugar SH1011 column, 8.0 mm×300 mm, (Showa Denko K.K., Kanagawa, Japan (through Thompson Instruments, Clear Brook, Va.)) using 0.01 N aqueous sulfuric acid, isocratic, as the eluant. The sample was passed through a 0.2 µm syringe filter (PALL GHP membrane) into an HPLC vial. The HPLC run conditions were as follows:

Injection volume: 10 µL
Flow rate: 0.80 mL/minute
Run time: 32 minutes
Column Temperature: 50° C.
Detector: refractive index
Detector temperature: 40° C.
UV detection: 210 nm, 4 nm bandwidth After the run, concentrations in the sample were determined from standard curves for each of the compounds. The retention times were 27.0 and 8.7 minutes for isobutanol and glucose, respectively.

Example 1

Screening of Solvents

The purpose of this Example was to screen various organic solvents for use in the extractive fermentation of butanols. Solvent characteristics that were investigated were the partitioning of isobutanol between the solvent and an aqueous phase, the emulsion forming tendency of the solvent in the two-phase system, and the biocompatibility of the solvent with a wild-type *Saccharomyces cerevisiae* strain.

The partitioning of isobutanol between water and the following solvents: oleic acid (CAS No. 112-80-1), oleyl alcohol (CAS No. 143-28-2), octanoic acid (CAS No. 124-07-2), 1-nonanol (CAS No. 28473-21-4), 1-dodecanol (CAS No. 112-53-8), 1-nonanal (CAS No. 124-19-6), and 1-decanol (CAS No. 112-30-1) was investigated. Isobutanol was added to water to give aqueous solutions having a final isobutanol concentration of 10, 30, 50, and 70 g/L. These aqueous butanol solutions (12 mL) were added to test tubes and 4 mL of the solvent to be tested was added. Each solvent was tested in duplicate at each isobutanol concentration. The tubes were incubated for 3 hours with mixing at 30° C. After that time, the aqueous phase and the solvent phase from each tube were separated by centrifugation and analyzed for isobutanol using the GC Method described in the General Methods Section herein above. The partition coefficient for isobutanol between each solvent phase and the aqueous phase was calculated, i.e., $K_p = [\text{Isobutanol}]_{Org}/[\text{isobutanol}]_{Aq}$. The results are summarized in Table 2.

TABLE 2

Partition Coefficients for Isobutanol

| Solvent | Average Partition Coefficient |
|---|---|
| oleic acid | 2.7 |
| oleyl alcohol | 3.7 |
| octanoic acid | 6.7 |
| nonanol | 6.7 |
| 1-dodecanol | 5.2 |
| 1-nonanal | 5.7 |
| 1-decanol | 4.7 |

As can be seen from the data in the table, all the solvents tested had a favorable partition coefficient for isobutanol.

The biocompatibility of each solvent was determined using shake flask studies with *Saccharomyces cerevisiae* BY4741 obtained from ATCC. Seed shake flasks containing 700 mL of yeast extract/peptone/dextrose (YPD) medium were inoculated with 200 µL of *S. cerevisiae* BY4741 inoculum and incubated overnight at 30° C. with shaking at 250 rpm until the $OD_{600}$ reached about 0.5. Samples were withdrawn from the culture for measurement of $OD_{600}$ using a spectrophotometer and glucose concentration using HPLC.

The resulting seed culture was divided into eight 125 mL flasks as follows. Into one flask, which served as a control, 100 mL of the seed culture was added. Into the remaining seven flasks, 75 mL of the seed culture and 25 mL of the solvent to be tested was added. The flasks were incubated at 30° C., with shaking at 250 rpm in a table top shaker (Innova 4230, New Brunswick Scientific, Edison, N.J.) and samples were removed from each flask at various times and the $OD_{600}$ and glucose concentration were measured. The results are summarized in Tables 3 and 4.

TABLE 3

Optical Density Results

| Solvent | $OD_{600}$ t = 0 | $OD_{600}$ t = 2 h | $OD_{600}$ t = 4 | $OD_{600}$ t = 6 h | $OD_{600}$ t = 24 h |
|---|---|---|---|---|---|
| none (control) | 0.5 | 1.0 | 2.6 | 3.4 | 4.7 |
| oleic acid | 0.5 | 0.8 | 1.7 | 2.8 | 4.4 |
| oleyl alcohol | 0.5 | 1.0 | 2.0 | 2.4 | 3.5 |
| octanoic acid | 0.5 | 0.9 | 0.8 | 0.7 | 1.0 |
| nonanol | 0.5 | 0.5 | 0.7 | 0.6 | 0.7 |
| 1-dodecanol | 0.5 | 0.9 | 1.6 | 2.8 | 4.2 |
| 1-nonanal | 0.5 | 0.7 | 0.7 | 0.8 | 1.8 |
| 1-decanol | 0.5 | 0.5 | 0.7 | 0.6 | 0.8 |

TABLE 4

Glucose Results

| Solvent | Glucose (g/L) t = 0 | Glucose (g/L) t = 2 h | Glucose (g/L) t = 4 h | Glucose (g/L) t = 6 h | Glucose (g/L) t = 24 h |
|---|---|---|---|---|---|
| none (control) | 17.5 | 14.9 | 9.3 | 2.1 | 0.0 |
| oleic acid | 17.5 | 19.0 | 10.2 | 2.2 | 0.0 |
| oleyl alcohol | 17.5 | 15.3 | 10.4 | 3.4 | 0.0 |
| octanoic acid | 17.5 | 17.1 | 17.6 | 19.2 | 18.5 |
| nonanol | 17.5 | 17.0 | 16.9 | 18.1 | 17.8 |
| 1-dodecanol | 17.5 | 15.4 | 11.6 | 3.9 | 0.0 |
| 1-nonanal | 17.5 | 16.6 | 17.0 | 17.8 | 17.6 |
| 1-decanol | 17.5 | 16.6 | 17.0 | 17.8 | 17.6 |

As can been from the results in Tables 3 and 4, the *S. cerevisiae* grown in the presence of oleic acid, oleyl alcohol, and 1-dodecanol exhibited about the same level of glucose utilization and growth as the control without solvent, indicating that these solvents are biocompatible with the *S. cerevisiae* strain tested. The solvents octanoic acid, 1-nonanal, 1-decanol, and nonanol all inhibited growth and glucose utilization of the *S. cerevisiae* strain.

Example 2 And Example 3

Comparative

Growth of *Saccharomyces cerevisiae* in the Presence of Isobutanol and Oleyl Alcohol The purpose of these Examples was to demonstrate that oleyl alcohol mitigates the toxicity of isobutanol to *Saccharomyces cerevisiae*. The glucose consumption rate and the growth rate of wild-type *Saccharomyces cerevisiae* BY4741 strain were measured in shake flask cultures containing a high concentration of isobutanol in the presence of oleyl alcohol (Example 2) and the absence of oleyl alcohol (Example 3, Comparative).

Three seed shake flasks containing 600 mL of YPD medium were inoculated with 100, 300, and 1000 µL of *Saccharomyces cerevisiae* BY4741 inoculum, respectively. The flasks were incubated overnight at 30° C. with shaking at 250 rpm until the $OD_{600}$ reached about 0.1. Samples were withdrawn from each culture and the $OD_{600}$ and glucose concentration were measured as described above.

To a 125 mL flask was added 100 mL of the culture which was derived from the 300 µL inoculum (Example 3, Comparative). To another 125 mL flask was added 75 mL of the culture and 25 mL of oleyl alcohol (i.e., 25 vol %) (Example 2). The flasks were incubated at 30° C. with shaking at 100 rpm. Samples were withdrawn for $OD_{600}$ and glucose measurement. When the $OD_{600}$ reached about 0.4, isobutanol was added to both flasks to a final concentration of 30 g/L of the aqueous phase. A third flask containing 75 mL of the culture and 25 vol % of oleyl alcohol, but no added isobutanol, served as a positive control. Samples were withdrawn from all flasks at various times for the determination of $OD_{600}$ and glucose concentration. The optical density results and the glucose results are given in Tables 5 and 6, respectively.

TABLE 5

Optical Density Results in the Presence and Absence of Oleyl Alcohol

| Time (h) | Example 2 $OD_{600}$ | Example 3 (Comparative) $OD_{600}$ | Control $OD_{600}$ |
|---|---|---|---|
| 0 (isobutanol addition) | 0.4 | 0.4 | 0.4 |
| 3 | 0.5 | 0.6 | 0.6 |
| 4 | 1.3 | 0.7 | 1.7 |
| 5 | 1.7 | 0.6 | 2.5 |
| 14 | 3.1 | 0.6 | 3.3 |

TABLE 6

Glucose Concentration in the Presence and Absence of Oleyl Alcohol

| Time (h) | Example 2 Glucose (g/L) | Example 3 (Comparative) Glucose (g/L) | Control Glucose (g/L) |
|---|---|---|---|
| 0 (isobutanol addition) | 18.9 | 18.9 | 19.7 |
| 3 | 16.6 | 17.5 | 16.0 |
| 4 | 14.4 | 17.7 | 12.9 |
| 5 | 12.0 | 17.4 | 9.2 |
| 14 | 2.7 | 17.4 | 0.3 |

As can be seen from the data in Tables 5 and 6, isobutanol at a concentration of 30 g/L in the absence of oleyl alcohol (Example 3, Comparative) almost completely inhibited glucose utilization and biomass growth. However, the culture was able to grow and utilize glucose In the presence of isobutanol at a concentration of 30 g/L when oleyl alcohol was added to the culture. The growth and glucose utilization rate of the culture containing isobutanol and oleyl alcohol were comparable to those of the control containing only oleyl alcohol. These results demonstrate that oleyl alcohol mitigates the toxicity of isobutanol to the strain of *Saccharomyces cerevisiae* studied. It would be reasonable to expect that oleyl alcohol could be used to mitigate the toxicity of isobutanol, as well as other butanols, to other strains of *Saccharomyces cerevisiae*, including recombinant strains.

Example 4 And Example 5

Comparative

Growth of *Lactobacillus plantarum* in the Presence of Isobutanol and Oleyl Alcohol The purpose of these Examples was to demonstrate that oleyl alcohol mitigates the toxicity of isobutanol to *Lactobacillus plantarum*. The glucose consumption rate and the growth rate of *Lactobacillus plantarum* strain PN0512 were measured in shake flask cultures containing a high concentration of isobutanol in the presence of oleyl alcohol (Example 4) and the absence of oleyl alcohol (Example 5, Comparative).

Three seed shake flasks containing 50 mL of de Man-Rogosa-Sharpe (MRS) medium were inoculated with 200, 500, and 1000 μL, respectively, of *Lactobacillus plantarum* strain PN0512 inoculum (ATCC: PTA-7727, biological deposit made Jul. 12, 2006 for U.S. patent application Ser. No. 11/761,497). The flasks were incubated overnight at 30° C. with shaking at 250 rpm until the $OD_{600}$ was between 2 and 5. A 1-L flask containing 600 mL of MRS medium was inoculated from one of the above seed flasks having an $OD_{600}=3$ to an initial $OD_{600}=0.1$ and cultivated at 30° C. with shaking at 180 rpm. After 4 to 5 hours of cultivation, the $OD_{600}$ was between 0.5 and 1.0. Samples were withdrawn from each culture and the $OD_{600}$ and glucose concentration were measured as described above.

To a 125 mL flask was added 100 mL of the culture from the above mentioned 1-L flask (Example 3, Comparative). To another 125 mL flask was added 75 mL of the culture and 25 mL of oleyl alcohol (i.e., 25 vol %) (Example 2). The flasks were incubated at 30° C. with shaking at 100 rpm. Samples were withdrawn for $OD_{600}$ and glucose measurement. When the $OD_{600}$ reached about 1.5, isobutanol was added to both flasks to a final concentration of 30 g/L of the aqueous phase. A third flask containing 75 mL of the culture and 25 vol % of oleyl alcohol, but no added isobutanol, served as a positive control. Samples were withdrawn from all flasks at various times for the determination of $OD_{600}$ and glucose concentration. The optical density results and the glucose results are given in Tables 7 and 8, respectively.

TABLE 7

Optical Density Results in the Presence and Absence of Oleyl Alcohol

| Time (h) | Example 4 $OD_{600}$ | Example 5 (Comparative) $OD_{600}$ | Control $OD_{600}$ |
| --- | --- | --- | --- |
| 0 (isobutanol addition) | 6.2 | 5.7 | 5.6 |
| 3 | 8.8 | 6.8 | 8.9 |
| 4 | 10.4 | 6.9 | 10.4 |
| 5 | 12.6 | 7.2 | 14.1 |
| 14 | 7.4 | 5.3 | 8.8 |

TABLE 8

Glucose Concentration in the Presence and Absence of Oleyl Alcohol

| Time (h) | Example 4 Glucose (g/L) | Example 5 (Comparative) Glucose (g/L) | Control Glucose (g/L) |
| --- | --- | --- | --- |
| 0 (isobutanol addition) | 12.9 | 12.7 | 12.9 |
| 3 | 7.8 | 11.7 | 7.4 |
| 4 | 5.2 | 11.7 | 4.5 |
| 5 | 2.8 | 11.7 | 1.9 |
| 14 | 0 | 11.6 | 0 |

As can be seen from the data in Tables 7 and 8, isobutanol at a concentration of 30 g/L in the absence of oleyl alcohol (Example 3, Comparative) almost completely inhibited glucose utilization and biomass growth of the *Lactobacillus* strain. However, the culture was able to grow and utilize glucose in the presence of isobutanol at a concentration of 30 g/L when oleyl alcohol was added to the culture. The growth and glucose utilization rate of the culture containing isobutanol and oleyl alcohol were comparable to those of the control containing only oleyl alcohol. These results demonstrate that oleyl alcohol mitigates the toxicity of isobutanol to the strain of *Lactobacillus plantarum* studied. It would be reasonable to expect that oleyl alcohol could be used to mitigate the toxicity of isobutanol, as well as other butanols, to other strains of *Lactobacillus plantarum*, including recombinant strains.

Example 6

Production of Isobutanol By Recombinant *Escherichia coli* Using Extractive Fermentation The purpose of this Example was to demonstrate the production of isobutanol by a recombinant strain of *Escherichia coli* that contains an isobutanol biosynthetic pathway using extractive fermentation with oleyl alcohol as the water immiscible, organic extractant.

The strain used was *Escherichia coli* Strain NGCI-031, constructed as described in the General Methods Section herein above. All seed cultures for inoculum preparation were grown in Luria-Bertani (LB) medium with ampicillin (100 mg/L) as the selection antibiotic. The fermentation medium was a semi-synthetic medium, the composition of which is given in Table 9.

TABLE 9

Fermentation Medium Composition

| Ingredient | Amount/L |
| --- | --- |
| Phosphoric Acid 85% | 0.75 mL |
| Sulfuric Acid (18 M) | 0.30 mL |
| Balch's w/ Cobalt - 1000X (composition given in Table 10) | 1.00 mL |
| Potassium Phosphate Monobasic | 1.40 g |
| Citric Acid Monohydrate | 200 g |
| Magnesium Sulfate, heptahydrate | 200 g |
| Ferric Ammonium Citrate | 0.33 g |
| Calcium chloride, dihydrate | 0.20 g |
| Yeast Extract[a] | 5.00 g |
| Antifoam 204[b] | 0.20 mL |
| Thiamine•HCl, 5 g/L stock | 1.00 mL |
| Ampicillin, 25 mg/mL stock | 4.00 mL |
| Glucose 50 wt % stock | 33.3 mL |

[a]Obtained from BD Diagnostic Systems, Sparks, MD
[b]Obtained from Sigma-Aldrich

TABLE 10

Balch's Modified Trace Metals - 1000X

| Ingredient | Concentration (g/L) |
| --- | --- |
| Citric Acid Monohydrate | 40.0 |
| $MnSO_4 \cdot H_2O$ | 30.0 |
| NaCl | 10.0 |
| $FeSO_4 \cdot 7H_2O$ | 1.0 |
| $CoCl_2 \cdot 6H_2O$ | 1.0 |
| $ZnSO_4 \cdot 7H_2O$ | 1.5 |
| $CuSO_4 \cdot 5H_2O$ | 0.1 |
| Boric Acid ($H_3BO_3$) | 0.1 |
| Sodium Molybnate ($NaMoO_4 \cdot 2H_2O$) | 0.1 |

Ingredients 1-10 from Table 9 were added to water at the prescribed concentration to make a final volume of 1.5 L in the fermentor. The contents of the fermentor were sterilized by autoclaving. Components 11-13 were mixed, filter sterilized and added to the fermentor after the autoclaved medium had cooled. The total final volume of the fermentation medium (the aqueous phase) was about 1.6 L.

The fermentation was done using a Biostat-B DCU-3 fermentor (Braun Biotech International, Melesungen, Germany) with a working volume of 2.0 L. The temperature was maintained at 30° C. during the entire fermentation and the pH was maintained at 6.8 using ammonium hydroxide. Following inoculation of the sterile fermentation medium with seed culture (2-10 vol %), the fermentor was operated aerobically at a 30% dissolved oxygen (DO) set point with 0.5 vvm of air flow by automatic control of the agitation rate (rpm). Once the desired optical density ($OD_{600}$) was reached (i.e., $OD_{600}$=10), the culture was induced with the addition of 0.4-0.5 mM IPTG to overexpress the isobutanol biosynthetic pathway. Four hours post induction, fermentation conditions were switched to microaerobic conditions by decreasing the stirrer speed to 200 rpm. The shift to microaerobic conditions initiated isobutanol production while minimizing the amount of carbon going to biomass production, thereby uncoupling biomass formation from isobutanol production. Oleyl alcohol (about 780 mL) was added during the isobutanol production phase to alleviate the problem of inhibition due to build up of isobutanol in the aqueous phase. Glucose was added as a bolus (50 wt % stock solution) to the fermentor to keep levels of glucose between 30 g/L and 2 g/L.

Because efficient production of isobutanol requires microaerobic conditions to enable redox balance in the biosynthetic pathway, air was continuously supplied to the fermentor at 0.5 vvm. Continuous aeration led to significant stripping of isobutanol from the aqueous phase of the fermentor. To quantify the loss of isobutanol due to stripping, the off-gas from the fermentor was sparged through a chilled (6.5° C.) water trap to condense the isobutanol, which was then quantified using the GC Method described in the General Methods Section herein above. Alternatively, the air stream exiting the fermentor was directly sent to a mass spectrometer (Prima dB mass spectrometer, Thermo Electron Corp., Madison, Wis.) to quantify the amount of isobutanol in the gas stream. The isobutanol peaks at mass to charge ratios of 74 or 42 were monitored continuously to quantify the amount of isobutanol in the gas stream.

For isobutanol production, the effective titer, the effective rate, and the effective yield, all corrected for the isobutanol lost due to stripping, were 37 g/L, 0.40 g/L/h, and 0.33 g/g, respectively. As can be seen by comparing these results to those obtained without oleyl alcohol as extractant (as shown in Example 7, Comparative below), the use of oleyl alcohol in an extractive fermentation for isobutanol production results in significantly higher effective titer, effective rate, and effective yield. The isobutanol product, which is toxic to the bacterial host, is continuously extracted into the oleyl alcohol phase, decreasing its concentration in the aqueous phase, thereby reducing the toxicity to the microorganism. Additionally, oleyl alcohol appears to have another, unexpected beneficial effect on isobutanol production. This can also be seen by comparison with Example 7 (Comparative). In that Example, gas stripping alone continuously removed isobutanol from the fermentation medium and limited the isobutanol concentration in the fermentation medium to a maximum of about 8-10 g/L, a level that is comparable to the level observed using a combination of extraction with oleyl alcohol and gas stripping (see FIG. 1). In both Examples, the isobutanol concentration was below inhibitory levels for most of the fermentation. However, significantly higher isobutanol effective titer, effective rate, and effective yield were obtained with a combination of oleyl alcohol extractive fermentation and gas stripping (Example 6) than with gas stripping alone (Example 7), suggesting the oleyl alcohol has another, unexpected beneficial effect on isobutanol production.

Example 7

Comparative

Production of Isobutanol By Recombinant *Escherichia coli* Using Fermentation Without Addition of an Extractant The purpose of this Comparative Example was to demonstrate that without the addition of oleyl alcohol the production of isobutanol is inhibited due to the toxicity of the product.

The fermentation was done as described in Example 6, except that oleyl alcohol was not added to the fermentation medium during the isobutanol production phase. The following changes were also made. The culture was induced by addition of IPTG when the $OD_{600}$ reached 6, and the switch to microaerobic conditions was made 3 hours post induction. To quantify the amount of isobutanol lost due to stripping, the off-gas from the fermentor was sent directly to a mass spectrometer (Prima dB, Thermo Electron Corp., Madison, Wis.). The isobutanol peaks at mass to charge ratios of 74 or 42 were continuously monitored to quantify isobutanol loss due to stripping.

For isobutanol production, the effective titer, the effective rate, and the effective yield, all corrected for the isobutanol lost due to stripping, were 13 g/L, 0.21 g/L/h, and 0.22 g/g, respectively. Because isobutanol was continuously removed from the fermentation medium by gas stripping, the isobutanol concentration in the aqueous phase during fermentation was limited to a maximum of 8-10 g/L, and was actually below inhibitory levels for most of the fermentation (see FIG. 1).

Example 8

Production of Isobutanol By Recombinant *Saccharomyces cerevisiae* Using Extractive Fermentation The purpose of this Example was to demonstrate the production of isobutanol by a recombinant strain of *Saccharomyces cerevisiae* that contains an isobutanol biosynthetic pathway using extractive fermentation with oleyl alcohol as the water immiscible, organic extractant.

The strain used was *Saccharomyces cerevisiae* Strain NGCI-049, constructed as described in the General Methods Section herein above. All seed cultures for inoculum preparation were grown in Yeast Nitrogen Base (YNB) without amino acids medium (6.7 g/L), supplemented with amino acid dropout mix (1.4 g/L), leucine (100 mg/L) and tryptophan (20 mg/L). Ethanol at 1% (v/v) was used as the sole carbon source for all seed cultures. The fermentation medium was a semi-synthetic medium, the composition of which is given in Table 11.

TABLE 11

| Fermentation Medium Composition | |
|---|---|
| Ingredient | Amount/L |
| 1. YNB w/o amino acids[a] | 6.7 g |
| 2. Sigma Dropout Mix (Y2001)[b] | 2.8 g |
| 3. Leucine (10 g/L) | 20 mL |
| 4. Tryptophan (10 g/L) | 4 mL |

TABLE 11-continued

Fermentation Medium Composition

| Ingredient | Amount/L |
|---|---|
| 5. Ethanol | 10 mL |
| 6. Glucose 50 wt % stock | 4 g |

[a]Obtained from BD Diagnostic Systems, Sparks, MD
[b]Obtained from Sigma-Aldrich, St. Louis, MO Ingredients 1-4 from Table 11 were added to water at the prescribed concentration to make a final volume of 0.54 L in the fermentor. The contents of the fermentor were sterilized by autoclaving. Components 5 and 6 were mixed, filter sterilized and added to the fermentor after the autoclaved medium had cooled. The total final volume of the fermentation medium (the aqueous phase) was about 0.54 L.

The fermentation was done using a 1 L autoclavable bioreactor, Bio Console ADI 1025 (Applikon, Inc, Holland) with a working volume of 900 mL. The temperature was maintained at 30° C. during the entire fermentation and the pH was maintained at 5.5 using sodium hydroxide. Following inoculation of the sterile fermentation medium with seed culture (10 vol %), the fermentor was operated aerobically at a 30% dissolved oxygen (DO) set point with 0.3 vvm of air flow by automatic control of the agitation rate (rpm). Once the initial batched glucose of 2 g/L was consumed, glucose was fed using a pump at an exponential rate such that glucose never accumulated above 0.2 g/L in the fermentor. Once the desired optical density ($OD_{600}$) was reached (i.e., $OD_{600}$=6), the culture was induced to isobutanol production phase by feeding glucose such that excess glucose (>2 g/L) was maintained at all times during fermentation. Two hours post glucose excess, 60 mL of filter sterilized 10× Yeast Extract Peptone stock solution (10×YEP=100 g/L of yeast extract and 200 g/L of peptone) was added. Two hours post addition of YEP, Oleyl alcohol (about 300 mL) was added during the isobutanol production phase to alleviate the problem of inhibition due to build up of isobutanol and other byproducts in the aqueous phase. Glucose was fed (50 wt % stock solution) to the fermentor to keep levels of glucose greater than 2 g/L.

Because efficient production of isobutanol requires microaerobic conditions to enable redox balance in the biosynthetic pathway, air was continuously supplied to the fermentor at 0.3 vvm. Continuous aeration led to significant stripping of isobutanol from the aqueous phase of the fermentor. To quantify the loss of isobutanol due to stripping, the off-gas from the fermentor was directly sent to a mass spectrometer (Prima dB mass spectrometer, Thermo Electron Corp., Madison, Wis.) to quantify the amount of isobutanol in the gas stream. The isobutanol peaks at mass to charge ratios of 74 or 42 were monitored continuously to quantify the amount of isobutanol in the gas stream.

Glucose and organic acids in the aqueous phase were monitored during the fermentation using HPLC. Glucose was also monitored quickly using a glucose analyzer (YSI, Inc., Yellow Springs, Ohio). Isobutanol in the aqueous phase was quantified by HPLC and isobutanol in the oleyl alcohol phase were monitored using the GC method described in the General Method Section herein above after the two phases were removed periodically from the fermentor and separated by centrifugation. The concentration of isobutanol in the aqueous phase during the fermentation is shown in FIG. 2, where the closed squares (■) refer to the concentrations of Example 8, fermentation using oleyl alcohol as the organic extractant with gas stripping, and the closed circles (●) refer to the concentrations of Example 9 (Comparative), fermentation with gas stripping alone.

For isobutanol production, the effective titer, the effective rate, and the effective yield, all corrected for the isobutanol lost due to stripping, were 5 g/L, 0.06 g/L/h, and 0.16 g/g, respectively. As can be seen by comparing these results to those obtained without oleyl alcohol as extractant (as shown in Example 9, Comparative below), the use of oleyl alcohol in an extractive fermentation for isobutanol production results in significantly higher effective titer, effective rate, and effective yield. The isobutanol product, which is toxic to the host, is continuously extracted into the oleyl alcohol phase, decreasing its concentration in the aqueous phase, thereby reducing the toxicity to the microorganism. Additionally, oleyl alcohol appears to have another, unexpected beneficial effect on isobutanol production. This can also be seen by comparison with Example 9 (Comparative). In that Example, gas stripping alone continuously removed isobutanol from the fermentation medium and limited the isobutanol concentration in the fermentation medium to a maximum of about 4 g/L, a level that is comparable to the level observed using a combination of extraction with oleyl alcohol and gas stripping (see FIG. 2). In both Examples, the isobutanol concentration was below inhibitory levels for most of the fermentation. However, significantly higher isobutanol effective titer, effective rate, and effective yield were obtained with a combination of oleyl alcohol extractive fermentation and gas stripping (Example 8) than with gas stripping alone (Example 9), suggesting the oleyl alcohol has another, unexpected beneficial effect on isobutanol production.

Example 9

Comparative

Production of Isobutanol By Recombinant Saccharomyces cerevisiae Using Fermentation Without Addition of an Extractant The purpose of this Comparative Example was to demonstrate that without the addition of oleyl alcohol the production of isobutanol is inhibited due to the toxicity of the product.

The fermentation was done as described in Example 8, except that oleyl alcohol was not added to the fermentation medium during the isobutanol production phase. To quantify the amount of isobutanol lost due to stripping, the off-gas from the fermentor was sent directly to a mass spectrometer (Prima dB, Thermo Electron Corp., Madison, Wis.). The isobutanol peaks at mass to charge ratios of 74 or 42 were continuously monitored to quantify isobutanol loss due to stripping.

For isobutanol production, the effective titer, the effective rate, and the effective yield, all corrected for the isobutanol lost due to stripping, were 3 g/L, 0.04 g/L/h, and 0.16 g/g, respectively. Because isobutanol was continuously removed from the fermentation medium by gas stripping, the isobutanol concentration in the aqueous phase during fermentation was limited to a maximum of 2-3 g/L, and was actually below inhibitory levels for most of the fermentation (see FIG. 2).

Example 10

A 2 L fermentor can be used to run a fermentation with recombinant yeast producing isobutanol as in Example 8 except that a portion of the initial batched oleyl alcohol is removed and replaced with fresh oleyl alcohol. This process can be run in a continuous mode where fresh oleyl alcohol is slowly trickled in and spent oleyl alcohol is pumped out such that the amount of oleyl alcohol in the fermentor remains constant during the entire fermentation process. Such continuous extraction of products and byproducts from the fermentation can increase effective rate, titer and yield.

What is claimed is:

1. A method for recovering butanol from a fermentation medium, the method comprising:
   a) providing a fermentation medium comprising butanol, water, and a genetically modified yeast that produces butanol from a fermentation medium comprising at least one fermentable carbon source;
   b) providing oleic acid and adding steric acid to form an extractant;
   c) contacting the fermentation medium with the extractant comprising oleic acid and stearic acid to form a two-phase mixture comprising an aqueous phase and a butanol-containing organic phase;
   d) separating the butanol-containing organic phase from the aqueous phase; and
   e) recovering the butanol from the butanol-containing organic phase to produce recovered butanol;
   wherein the extractant is recycled.

2. The method according to claim 1, wherein the butanol is isobutanol.

3. The method of claim 1, wherein the fermentation medium further comprises ethanol, and the butanol-containing organic phase contains ethanol.

4. The method of claim 1, wherein the yeast is *Saccharomyces cerevisiae*.

5. A method for the production butanol, comprising:
   a) providing a genetically modified yeast that produces butanol from a fermentation medium comprising at least one fermentable carbon source;
   b) providing oleic acid and adding steric acid to form an extractant;
   c) growing the yeast in a biphasic fermentation medium comprising an aqueous phase and the extractant comprising oleic acid and stearic acid, wherein said biphasic fermentation medium comprises from about 3% to about 60% by volume of the extractant, for a time sufficient to allow extraction of the butanol into the extractant to form a butanol-containing organic phase;
   d) separating the butanol-containing organic phase from the aqueous phase; and
   e) recovering the butanol from the butanol-containing organic phase to produce recovered butanol;
   wherein the extractant is recycled.

6. The method according to claim 5, wherein the butanol is isobutanol.

7. The method of claim 5, wherein the fermentation medium further comprises ethanol, and the butanol-containing organic phase comprises ethanol.

8. The method of claim 5, wherein the yeast is *Saccharomyces cerevisiae*.

9. A method for the production of butanol comprising the steps of:
   a) providing a genetically modified yeast that produces butanol from a fermentation medium comprising at least one fermentable carbon source;
   b) growing the microorganism in a fermentation medium wherein the yeast produces said butanol into the fermentation medium to produce a butanol-containing fermentation medium;
   c) providing oleic acid and adding steric acid to form an extractant;
   d) contacting the butanol-containing fermentation medium with the extractant comprising oleic acid and stearic to form a two-phase mixture comprising an aqueous phase and a butanol-containing organic phase;
   e) separating the butanol-containing organic phase from the aqueous phase; and
   f) recovering the butanol from the butanol-containing organic phase;
   wherein the extractant is recycled.

10. The method according to claim 9, wherein the butanol is isobutanol.

11. The method of claim 9, wherein the yeast is *Saccharomyces cerevisiae*.

12. A method for the production of butanol comprising the steps of:
   a) providing a genetically modified yeast that produces butanol from a fermentation medium comprising at least one fermentable carbon source;
   b) growing the yeast in a fermentation medium under aerobic conditions for a time sufficient to reach a preselected growth level;
   c) switching to microaerobic or anaerobic conditions to stimulate butanol production into the fermentation medium to form a butanol-containing fermentation medium;
   d) providing oleic acid and adding steric acid to form an extractant;
   e) contacting the butanol-containing fermentation medium with the extractant comprising oleic acid and stearic acid to form a two-phase mixture comprising an aqueous phase and a butanol-containing organic phase;
   f) separating the butanol-containing organic phase from the aqueous phase; and
   g) recovering the butanol from the butanol-containing organic phase;
   wherein the extractant is recycled.

13. The method according to claim 12 wherein the butanol is isobutanol.

14. The method of claim 12, wherein the yeast is *Saccharomyces cerevisiae*.

15. A method for the production of butanol comprising the steps of:
   a) providing a fermentation medium comprising butanol, water, and a genetically modified yeast that produces butanol from a fermentation medium comprising at least one fermentable carbon source;
   b) providing oleic acid and adding steric acid to form an extractant;
   c) contacting the fermentation medium via a co-current or counter-current extractant stream with the extractant comprising oleic acid and stearic acid to form a two-phase mixture comprising an aqueous phase and a butanol-containing organic phase;
   d) separating the butanol-containing organic phase from the aqueous phase; and e) recovering the butanol from the butanol-containing organic phase to produce recovered butanol;

wherein the extractant is recycled.

16. The method according to claim 15, wherein the butanol is isobutanol.

17. The method of claim 15, wherein the yeast is *Saccharomyces cerevisiae*.

18. The method according to any of claims 1, 5, 9, 12, and 15, wherein a portion of the butanol is concurrently removed from the fermentation medium by a process comprising the steps of:

a) stripping butanol from the fermentation medium with a gas, forming a butanol-containing gas phase; and b) recovering butanol from the butanol-containing gas phase.

* * * * *